(12) United States Patent
Carling et al.

(10) Patent No.: US 9,567,328 B2
(45) Date of Patent: Feb. 14, 2017

(54) COMPOUNDS ACTING AT MULTIPLE PROSTAGLANDIN RECEPTORS GIVING A GENERAL ANTI-INFLAMMATORY RESPONSE

(71) Applicant: ALLERGAN, INC., Irvine, CA (US)

(72) Inventors: William R. Carling, Bishop's Stortford (GB); Jose L. Martos, Basildon Essex (GB); Jussi J. Kangasmetsa, Essex (GB); Jenny W. Wang, Irvine, CA (US); David F. Woodward, Lake Forest, CA (US)

(73) Assignee: ALLERGAN, INC., Irvine, CA (US)

( * ) Notice: Subject to any disclaimer, the term of this patent is extended or adjusted under 35 U.S.C. 154(b) by 76 days.

(21) Appl. No.: 13/720,520

(22) Filed: Dec. 19, 2012

(65) Prior Publication Data
US 2013/0184463 A1 Jul. 18, 2013

Related U.S. Application Data

(60) Provisional application No. 61/578,640, filed on Dec. 21, 2011.

(51) Int. Cl.
| | | |
|---|---|---|
| C07D 471/04 | (2006.01) | |
| C07D 231/56 | (2006.01) | |
| C07D 235/08 | (2006.01) | |
| C07D 401/06 | (2006.01) | |
| C07D 209/08 | (2006.01) | |

(52) U.S. Cl.
CPC ........... *C07D 471/04* (2013.01); *C07D 209/08* (2013.01); *C07D 231/56* (2013.01); *C07D 235/08* (2013.01); *C07D 401/06* (2013.01)

(58) Field of Classification Search
CPC .................................................. C07D 471/04
See application file for complete search history.

(56) References Cited

U.S. PATENT DOCUMENTS

| | | | |
|---|---|---|---|
| 4,166,452 A | 9/1979 | Generales | |
| 4,256,108 A | 3/1981 | Theeuwes | |
| 4,265,874 A | 5/1981 | Bonsen | |
| 5,334,765 A | 8/1994 | Jacobs | |
| 6,069,156 A | 5/2000 | Oku | |
| 6,348,032 B1* | 2/2002 | Sperl et al. | 514/338 |
| 6,358,992 B1* | 3/2002 | Pamukcu et al. | 514/414 |
| 6,511,999 B2 | 1/2003 | Burk | |
| 2002/0082280 A1 | 6/2002 | Sperl et al. | |
| 2004/0162323 A1 | 8/2004 | Krauss | |
| 2005/0065200 A1 | 3/2005 | Woodward | |
| 2006/0089367 A1* | 4/2006 | Bleicher et al. | 514/254.06 |
| 2006/0160884 A1 | 7/2006 | Park | |
| 2007/0060596 A1 | 3/2007 | Giblin | |
| 2010/0197708 A1 | 8/2010 | Talley | |
| 2011/0028463 A1* | 2/2011 | Nozawa | C07D 409/06 514/230.5 |

FOREIGN PATENT DOCUMENTS

| | | | |
|---|---|---|---|
| EP | 2570125 | 3/2013 | |
| EP | 2669270 | 12/2013 | |
| JP | 2000-501105 | 2/2000 | |
| JP | 2008-509138 | 3/2008 | |
| JP | 2008-517959 | 5/2008 | |
| JP | WO 2009005076 A1 * | 1/2009 | .......... C07D 409/06 |
| WO | 9723480 | 7/1997 | |
| WO | 01-12187 | 2/2001 | |
| WO | WO 0112187 A2 * | 2/2001 | |
| WO | 03053938 | 7/2003 | |
| WO | 2006-015124 | 2/2006 | |
| WO | 2006017384 | 2/2006 | |
| WO | 2006045478 | 5/2006 | |
| WO | 2009083526 | 7/2009 | |
| WO | 2012-102405 | 8/2012 | |

(Continued)

OTHER PUBLICATIONS

Breyer "Prostanoid Receptors: Subtypes and Signaling" Annu. Rev. Pharmacol. Toxicol. 2001. 41:661-90.*
Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Barry "Pharmacotherapy for uveitis: current management and emerging therapy" Clinical Ophthalmology 2014:8 1891-1911.*
STN Chemical database Registry No. RN 1279850-40-6, 4-[[[3-amino-1-[(2-methoxyphenyl)methyl]-1H-indazol-5-yl]carbonyl]amino]—Butanoic acid, Entered STN: Apr. 14, 2011.*
Hulme "The synthesis and biological evaluation of a novel series of indole PDE4 inhibitors" Bioorganic & Medicinal Chemistry Letters, 1998, 8(14), 1867-1872.*
Beaulieu, Pierre et al, N-Acetamideindolecarboxylic Acid Allosteric 'finger-loop' Inhibitors of the Hepatitis C Virus NS5B Polymerase: Discovery and Initial Optimization Studies, Bioorganic & Medicinal Chemistry, 2010, 857-861, 20.

(Continued)

*Primary Examiner* — David K O Dell
(74) *Attorney, Agent, or Firm* — Jonathan Bass

(57) ABSTRACT

The present invention provides a compound, that is a 1-({halo-2-[(2-hydrocarbyl or substituted hydrocarbyl)oxy]phenyl}methyl)-(fused bicyclic nitrogen heteroaryl) carboxylic acid or an ester or sulfonamide thereof. The compound may be represented by the following formula

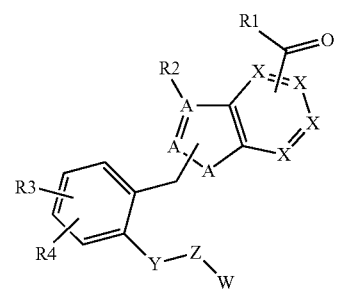

Wherein $R_1$, $R_2$, $R_3$, $R_4$ A, X, W, Z and Y are as defined in the specification. The compounds may be administered to treat DP, FP, EP1, TP and/or EP4 receptor-mediated diseases or conditions.

1 Claim, 2 Drawing Sheets

(56) References Cited

FOREIGN PATENT DOCUMENTS

WO    2013037960    3/2013

OTHER PUBLICATIONS

Figure 1:
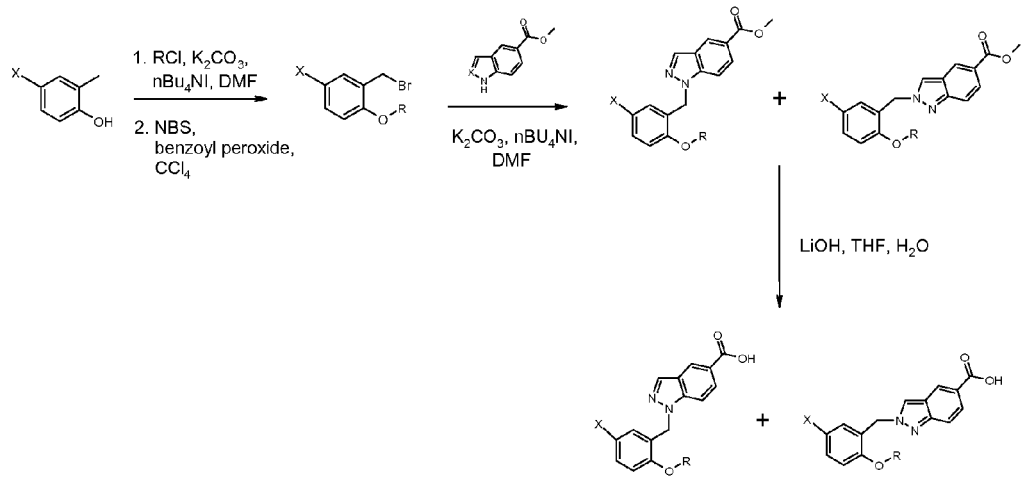

Castellani, ML et al, Anti-Chemokine Therapy for Inflammatory Diseases, International Journal of Immunopathology and Pharmacology, 2007, 447-453, 20(3), US.

Conti, P. et al, MCP-1 and RANTES Are Mediators of Acute and Chronic Inflammation, Allergy and Asthma Proc, 2001, 133-137, 22, US.

Garcia, Gilles et al, New Chemokine Targets for Asthma Therapy, Current Allergy and Asthma Reports, 2005, 155-160, 5, US.

Gleissner, Christian A. et al, Platelet Chemokines in Vascular Disease, ATVB in Focus Chemokines in Atherosclerosis, Thrombosis, and Vascular Biology, 2008, 1920-1927, 28, US.

Ho, CY et al, Suppressive effect of combination treatment of leflunomide and methotrexate on chemokine expression in patients with rheumatoid arthritis, Clin Exp Immunol, 2003, 132-138, 133, US.

Iwamoto, Takuji et al, Molecular aspects of rheumatoid arthritis: chemokines in the joints of patients, The FEBS Journal, 2008, 4448-4455, 275, US.

Jacobs, Robert et al, Substituted 3-(Phenylmethyl)-1H-indole-5-Carboxamides and 1-(Phenylmethyl)Indole-6-Carboxamides as Potent, Selective, Orally Active Antagonists of the Peptidoleukotrienes, J. Med. Chem., 1993, 394-409, 36.

Jacobs, Robert et al, Synthesis, Structure-Activity Relationships, and Pharmacological Evaluation of a Seri . . . , J. Med. Chem., 1994, 1282-1297, 37.

Matias, I., Prostaglandin Ethanolamides (Prostamides): In Vitro Pharmacology and Metabolism, The Journal of Pharmacology and Experimental Therapeutics, Jan. 29, 2004, 745-757, 209(2), US.

Pivarcsi, Andor et al, Chemokine Networks in Atopic Dermatitis: Traffic Signals of Disease, Current Allergy and Asthma Reports, 2005, 284-290, 5, US.

Qi, Xu-Feng et al, The adenylyl cyclase-cAMP system suppresses TARC/CCL17 and MDC/CCL22 production through p38 MAPK and NF-KB in HaCaT keratinocytes, Molecular Immunology, 2009, 1925-1934, 46, US.

Remingtons, Remingtons_16th, Pharmaceutical Sciences, 1980, 1-10, 16, Remingtons_16th.

Woodward, David et al, Characterization of Receptor Subtypes Involved in Prostanoid-Induced Conjunctival Pruritus and Their Role in Mediating Allergic Conjunctival Itching, The Journal of Pharmacology and Experimental Therapeutics, 1996, 137-142, 279.

Zernecke, Alma, Chemokines in Atherosclerosis an Update, Arterioscler Thromb Vasc Biol, 2008, 1897-1908, 28, US.

\* cited by examiner

COMPOUNDS ACTING AT MULTIPLE PROSTAGLANDIN RECEPTORS GIVING A GENERAL ANTI-INFLAMMATORY RESPONSE

CROSS-REFERENCE TO RELATED APPLICATION

This application claims the benefit of U.S. Provisional Application Ser. No. 61/578,640, filed Dec. 21, 2011, which is incorporated herein by reference in its entirety.

BACKGROUND OF THE INVENTION

1. Field of the Invention

This invention relates to compounds, to processes for their preparation, to pharmaceutical compositions containing them and to their use in medicine, in particular their use in the treatment of conditions mediated by the action of ligands for the $DP_1$, FP, TP, $EP_1$ and $EP_4$ prostaglandin (PG) receptors. The present compounds have the general structure shown below and act at different prostaglandin receptors to thereby provide a general anti-inflammatory response.

2. Summary of the Related Art

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

Prostaglandin $E_2$ ($PGE_2$) exerts allodynia through the $EP_1$ receptor subtype and hyperalgesia through $EP_2$ and $EP_3$ receptors in the mouse spinal cord. Furthermore, it has been shown that in the $EP_1$ knock-out mouse pain-sensitivity responses are reduced by approximately 50%. $EP_1$ receptor antagonist (ONO-8711) reduces hyperalgesia and allodynia in a rat model of chronic constriction injury and inhibits mechanical hyperalgesia in a rodent model of post-operative pain. The efficacy of $EP_1$ receptor antagonists in the treatment of visceral pain in a human model of hypersensitivity has been demonstrated. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects. Moreover, as a result of sparing potentially beneficial prostaglandin pathways, these agents may have enhanced efficacy and safety over NSAIDS and/or COX-2 inhibitors. $EP_4$ receptors have also been implicated in pain, hyperalgesia, allodynia, and inflammation. (See Pub. No. US 2005/0065200 which is hereby incorporated by reference for other diseases that may be treated by EP4 receptor antagonists.)

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys in the glomerulus and extraglomerular vascular tissue. Activation of TP receptors constricts glomerular capillaries and suppresses glomerular filtration rates indicating that TP receptor antagonists could be useful for renal dysfunction in glomerulonephritis, diabetes mellitus and sepsis.

Activation of TP receptors induces bronchoconstriction, an increase in microvascular permeability, formation of mucosal edema and mucus secretion, which are typical characteristic features of bronchial asthma. TP antagonists have been investigated as potential asthma treatments resulting in, for example, orally active Seratrodast (AA-2414). Ramatroban is another TP receptor antagonist currently undergoing phase III clinical trials as an anti-asthmatic compound.

Since $DP_1$ receptor stimulation may trigger an asthmatic response in certain individuals, compounds that have $DP_1$ antagonist properties may be useful as anti-asthmatic drugs. (See Pub. No. 2004/0162323 which is hereby incorporated by reference in its entirety for the disclosure of other diseases and conditions that may be treated with DP antagonists.)

Finally, the FP receptor modulates intraocular pressure and mediates smooth muscle contraction of the sphincter muscles in the gastrointestinal tract and the uterus. Thus, antagonists of the FP receptor are useful for treating reproductive disorders. (See U.S. Pat. No. 6,511,999 which is hereby incorporated by reference in its entirety for other diseases and conditions that may be treated with FP receptor antagonists.)

As further background for the present invention, see US Published Patent Application 2007/0060596 which is hereby incorporated by reference in its entirety.

BRIEF SUMMARY OF THE INVENTION

This invention provides compounds, that are 1-({halo-2-[(2-hydrocarbyl or substituted hydrocarbyl)oxy]phenyl}methyl)-(fused bicyclic nitrogen heteroaryl)carboxylic acids, or esters and sulfonamides thereof, such as 1-({halo-2-[(2-hydrocarbyl or substituted hydrocarbyl)oxy]phenyl}methyl)-(2,3 benzopyrrole or 2,3 benzo-1,2-diazole) carboxylic acids, or esters and sulfonamides thereof e.g. 1-({5-halo-2-[(2-alkyl)oxy]phenyl}methyl)-(2,3 benzopyrrole or 2,3 benzo-1,2-diazole)-5-carboxylic acids or esters or sulfonamides thereof. Said fused bicyclic nitrogen heteroaryl may be indole, isoindole, indolizine, benzotriazole, or purine. Preferably the ester or sulfonamide is an alkyl ester or sulfonamide. Preferably said halo is chloro or bromo and said alkyl is a branched chain alkyl having from 4 to 7 carbons, e.g. 3-ethylbutyl or 2-methylpropyl.

The invention further relates to pharmaceutical compositions containing the above compounds in combination with a pharmaceutically-acceptable excipient and to their use in medicine, in particular their use in the treatment of conditions mediated by the action of ligands for the $DP_1$, FP, $EP_1$ and $EP_4$ prostaglandin (PG) receptors. The compounds of this invention are also useful for treating conditions mediated by the action of ligands for the thromboxane (TP) receptor.

Some embodiments of the present invention include:

1. A compound, that is a 1-({halo-2-[(2-hydrocarbyl or substituted hydrocarbyl)oxy]phenyl}methyl)-(fused bicyclic nitrogen heteroaryl)carboxylic acid, or ester or sulfonamide thereof, and said hydrocarbyl may be a branched chain alkyl having from 4 to 7 carbons, e.g. 3-ethylbutyl or 2-methylpropyl.

2. A compound according to paragraph 1 wherein said compound is a 1-({5-halo-2-[(2-alkyl)oxy]phenyl}methyl)-(2,3 benzopyrrole or 2,3 benzo-1,2-diazole)-5-carboxylic acid or ester or sulfonamide thereof.

3. A compound according to paragraph 2 wherein said ester or sulfonamide is an alkyl ester or sulfonamide.

4. A compound according to paragraph 3, wherein said halo is selected from the group consisting of chloro and bromo.

5. A compound according to paragraph 3 wherein said alkyl is a branched chain alkyl having from 4 to 7 carbons.

6. A compound according to paragraph 3 wherein said alkyl is selected from the group consisting of 2-ethylbutyl and 2-methylpropyl.

7. A compound represented by the following formula

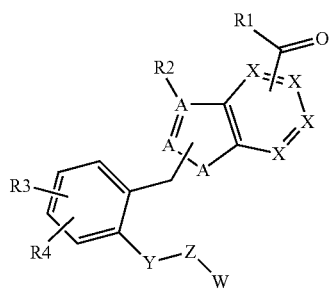

wherein X is N or $CR_7$;

A is N or $CR_7$ with the proviso that at least one A is N and when each A is N, $R_2$ is absent;

Y is $(CH_2)_m$ wherein m is 0 or an integer of from 1 to 3;

Z is selected from the group consisting of O, S, SO, $SO_2$ and $(CH_2)_p$, wherein p is 0 or an integer of from 1 to 3;

W is hydrocarbyl or substituted hydrocarbyl;

$R_1$ is selected from the group consisting of $OR_7$, $NH_2$, $N(R_7)_2$, and $N(R_7)SO_2R_7$;

$R_2$ is selected from the group consisting of H, hydroxyl, alkyl, aryl, alkoxy, aryloxy, halogen, nitro, amino, cyano and hydroxyl halogen, nitro, amino and cyano-substituted alkyl, aryl, alkoxy or aryloxy;

$R_3$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy; and, $R_7$ is selected from the group consisting of H, hydrocarbyl and substituted hydrocarbyl.

8. The compound of paragraph 7 wherein $R_7$ is selected from the group consisting of carbocyclic aryl and alkyl.

9. The compound of paragraph 7 wherein said compound is represented by the formula II:

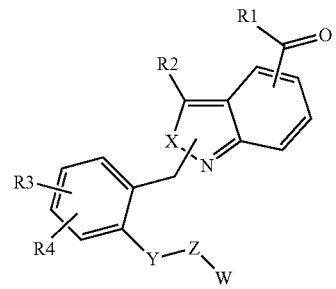

10. The compound of paragraph 9 wherein $R_1$ is OH.

11. The compound of paragraph 9 wherein $R_2$ is selected from the group consisting of H, alkyl and halogen substituted alkyl.

12. The compound of paragraph 11 wherein $R_2$ is selected from the group consisting of fluoro-substituted alkyl.

13. The compound of paragraph 10 wherein X is N or CH.

14. The compound of paragraph 7 wherein said compound is represented by formula III.

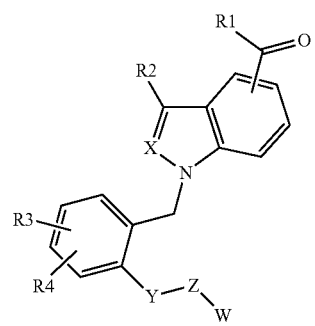

15. The compound of paragraph 10 wherein $R_3$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy.

16. The compound of paragraph 10 wherein $R_3$ is chloro or bromo.

17. The compound of paragraph 10 wherein $R_4$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy.

18. The compound of paragraph 10 wherein $R_4$ is H.

19. The compound of paragraph 10 wherein Y is absent, i.e. n is 0.

20. The compound of paragraph 10 wherein Z is O.

21. The compound of paragraph 10 wherein W is selected from the group consisting of alkyl, aryl, alkoxy, aryloxy and hydroxy, halogen, nitro, amino and cyano-substituted alkyl, aryl, alkoxy or aryloxy.

22. The compound of paragraph 10 wherein W is alkyl.

23. The compound of paragraph 10 wherein W is a branched chain alkyl.

24. The compound of paragraph 10 wherein W is 2-ethylbutyl or 2-methylpropyl.

25. The compound of paragraph 10 that is selected from the group consisting of:

1-[5-Chloro-2-(2-ethyl-butoxy)-benzyl]-1H-indole-5-carboxylic acid,

1-[5-Chloro-2-(2-ethyl-butoxy)-benzyl]-1H-indazole-5-carboxylic acid,
1-(2-Chloro-5-isobutoxy-benzyl)-1H-indazole-5-carboxylic acid,
1-(2-Bromo-5-isobutoxy-benzyl)-1H-indazole-5-carboxylic acid,
1-[2-Bromo-5-(2-ethyl-butoxy)-benzyl]-1H-indazole-5-carboxylic acid,
1-[2-Chloro-5-(2-ethyl-butoxy)-benzyl]-1H-indazole-6-carboxylic acid,
1-(5-Bromo-2-isobutoxy-benzyl)-1H-indazole-4-carboxylic acid,
1-(2-Benzyloxy-5-chloro-benzyl)-1H-indazole-5-carboxylic acid,
1-[5-Chloro-2-(4-chloro-benzyloxy)-benzyl]-1H-indazole-5-carboxylic acid,
1-(5-Chloro-2-cyclopentylmethoxy-benzyl)-1H-indazole-5-carboxylic acid,
1-(5-Chloro-2-cyclopropylmethoxy-benzyl)-1H-indazole-5-carboxylic acid,
1-(2-Benzyloxy-5-bromo-benzyl)-1H-indazole-5-carboxylic acid,
1-[5-Chloro-2-(4-chloro-benzyloxy)-benzyl]-1H-indazole-5-carboxylic acid,
1-(5-Chloro-2-cyclopentylmethoxy-benzyl)-1H-indazole-5-carboxylic acid,
1-(5-Bromo-2-cyclopropylmethoxy-benzyl)-1H-indazole-5-carboxylic acid,
2-(5-Chloro-2-isobutoxy-benzyl)-2H-indazole-5-carboxylic acid and
2-(5-Bromo-2-isobutoxy-benzyl)-2H-indazole-5-carboxylic acid.
1-(2-(Trifluoromethyl)-5-isobutoxy-benzyl)-1H-indazole-5-carboxylic acid,
1-(5-Bromo-2-cyclopropyl-2-methylmethoxy-benzyl)-1H-indazole-5-carboxylic acid,
1-(2-Isobutoxy-5-trifluoromethoxy-benzyl)-1H-indazole-5-carboxylic acid,
1-(5-Bromo-2-isobutoxy-benzyl)-3-methyl-1H-indazole-5-carboxylic acid,
1-(5-Bromo-2-isobutoxy-benzyl)-1H-pyrrolo[2,3-b]pyridine-5-carboxylic acid, and,
1-[5-Bromo-2-(2-ethyl-butoxy)-benzyl]-1H-pyrrolo[2,3-b]pyridine-5-carboxylic acid.

26. A method comprising administering a compound having the following formula

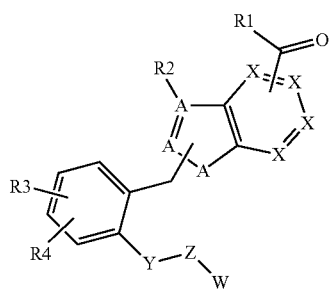

X is N or CR$_7$;
A is N or CR$_7$ with the proviso that at least one A is N and when each A is N, R$_2$ is absent;
Y is (CH$_2$)$_m$ wherein m is 0 or an integer of from 1 to 3;
Z is selected from the group consisting of O, S, SO, SO$_2$ and (CH$_2$)$_p$, wherein p is 0 or an integer of from 1 to 3;
W is hydrocarbyl or substituted hydrocarbyl;

R$_1$ is selected from the group consisting of OR$_7$, N(R$_7$)$_2$, and N(R$_7$)SO$_2$R$_7$;
R$_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
R$_3$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
R$_4$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and,
R$_7$ is selected from the group consisting of H, hydrocarbyl and substituted hydrocarbyl, e.g. carbocyclic aryl and alkyl.

27. The method of paragraph 26 wherein said compound is administered to treat DP1, FP, EP1, TP and/or EP4 receptor mediated diseases or conditions.

28. The method of paragraph 27 wherein said condition or disease is related to inflammation.

29. The method of paragraph 27 wherein said DP1, FP, EP1, TP and/or EP4 receptor mediated condition or disease is selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, endometriosis, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pre-term labor rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

30. The method of paragraph 27 wherein said compound is administered as a surgical adjunct in ophthalmology for cataract removal and artificial lens insertion, ocular implant procedures, photorefractive radial keratotomy and other ophthamological laser procedures.

31. The method of paragraph 27 wherein said compound is administered as a surgical adjunct in a procedure involving skin incisions, relief of pain and inflammation and scar formation/keloids post-surgery, for treating sports injuries and general aches and pains in muscles and joints.

32. The method of paragraph 27 wherein said DP$_1$, FP, EP$_1$, TP, and/or EP$_4$ receptor mediated condition or disease is an EP$_1$ and/or EP$_4$ receptor mediated condition or disease.

33. The method of paragraph 27 wherein said DP$_1$, FP, EP$_1$, TP and/or EP$_4$ receptor mediated condition or disease is an allergic condition.

34. The method of paragraph 33 wherein said condition is dermatological allergy.

35. The method of paragraph 27 wherein said condition is an ocular allergy.

36. The method of paragraph 27 wherein said condition is a respiratory allergy.

37. The method of paragraph 27 wherein said condition or disease is selected from the group consisting of nasal congestion, rhinitis, and asthma.
38. The method of paragraph 27 wherein said condition or disease is related to pain.
39. The method of paragraph 27 wherein said condition or disease is selected from the group consisting of arthritis, migraine, and headache.
40. The method of paragraph 27 wherein said condition or disease is associated with the gastrointestinal tract.
41. The method of paragraph 27 wherein said condition or disease is selected from the group consisting of peptic ulcer, heartburn, reflux esophagitis, erosive esophagitis, non-ulcer dyspepsia, infection by *Helicobacter pylori*, alrynitis, and irritable bowel syndrome.
42. The method of paragraph 27 wherein said condition or disease is selected from the group consisting of hyperalgesia and allodynia.
43. The method of paragraph 27 wherein said condition or disease is related to mucus secretion.
44. The method of paragraph 27 wherein said mucus secretion is gastrointestinal.
45. The method of paragraph 27 wherein said mucus secretion occurs in the nose, sinuses, throat, or lungs.
46. The method of paragraph 27 wherein said condition or disease is related to abdominal cramping.
47. The method of paragraph 27 wherein said condition or disease is irritable bowel syndrome.
48. The method of paragraph 27 wherein said condition or disease is a bleeding disorder.
49. The method of paragraph 27 wherein said condition or disease is a sleep disorder.
50. The method of paragraph 27 wherein said condition or disease is mastocytosis.
51. The method of paragraph 27 wherein said condition or disease is associated with elevated body temperature.
52. The method of paragraph 27 wherein said condition or disease is associated with ocular hypertension and glaucoma.
53. The method of paragraph 27 wherein said condition or disease is associated with ocular hypotension.
54. The method of paragraph 27 wherein said condition relates to surgical procedures to treat pain, inflammation and other unwanted sequelae wherein said surgical procedure includes incision, laser surgery or implantation.
55. The method of paragraph 27 where said condition is related to pain and inflammation and post-surgical scar and keloid formation.
56. The method of paragraph where said condition is related to diseases of female reproduction, associated with menstrual cramping, endometriosis, and pre-term labor
57 A pharmaceutical product comprising a compound having the following formula

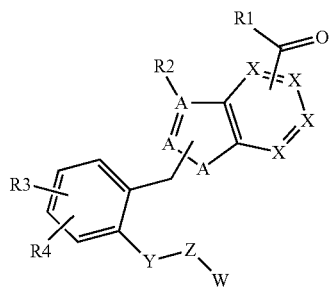

wherein X is N or $CR_7$;

A is N or $CR_7$ with the proviso that at least one A is N and when each A is N, $R_2$ is absent;

Y is $(CH_2)_m$ wherein m is 0 or an integer of from 1 to 3;

Z is selected from the group consisting of O, S, SO, $SO_2$ and $(CH_2)_p$, wherein p is 0 or an integer of from 1 to 3;

W is hydrocarbyl or substituted hydrocarbyl:

$R_1$ is selected from the group consisting of $OR_7$, $N(R_7)_2$, and $N(R_7)SO_2R_7$;

$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_3$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and, $R_7$ is selected from the group consisting of H, hydrocarbyl and substituted hydrocarbyl, e.g. carbocyclic aryl and alkyl or a pharmaceutically acceptable salt or a prodrug thereof 59. The compound of paragraphs 1-58 wherein the compounds are PG antagonists.
60. The compounds of paragraphs 1-58 wherein the compounds are useful for treating or reducing the symptoms of a $DP_1$, FP, $EP_1$, TP EP1 or $EP_4$ receptor mediated condition or disease and wherein said compound is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, endometriosis fertility disorders, hyperpyrexia, gangrene, glaucoma, hypothermia, immune and autoimmune diseases, inflammatory conditions, menstrual cramping, metastic tumor growth, migraine, mucus secretion disorders, nasal congestion, nasal inflammation, occlusive vascular diseases, ocular hypertension, ocular hypotension, osteoporosis, pain, perennial rhinitis, pre-term labor pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

58. A pharmaceutical composition comprising a compound having the following formula

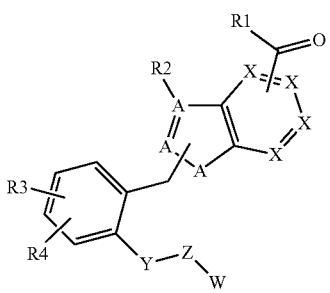

Wherein X is N or CR$_7$;
A is N or CR$_7$ with the proviso that at least one A is N and when each A is N, R$_2$ is absent;
Y is (CH$_2$)$_m$ wherein m is 0 or an integer of from 1 to 3;
Z is selected from the group consisting of O, S, SO, SO$_2$ and (CH$_2$)$_p$, wherein p is 0 or an integer of from 1 to 3;
W is hydrocarbyl or substituted hydrocarbyl:
R$_1$ is selected from the group consisting of OR$_7$, N(R$_7$)$_2$, and N(R$_7$)SO$_2$R$_7$;
R$_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
R$_3$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
R$_4$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and,
R$_7$ is selected from the group consisting of H, hydrocarbyl and substituted hydrocarbyl, e.g. carbocyclic aryl and alkyl or a pharmaceutically acceptable salt or a prodrug thereof, and a pharmaceutically acceptable excipient.

BRIEF DESCRIPTION OF THE DRAWING FIGURES

Figure 2:
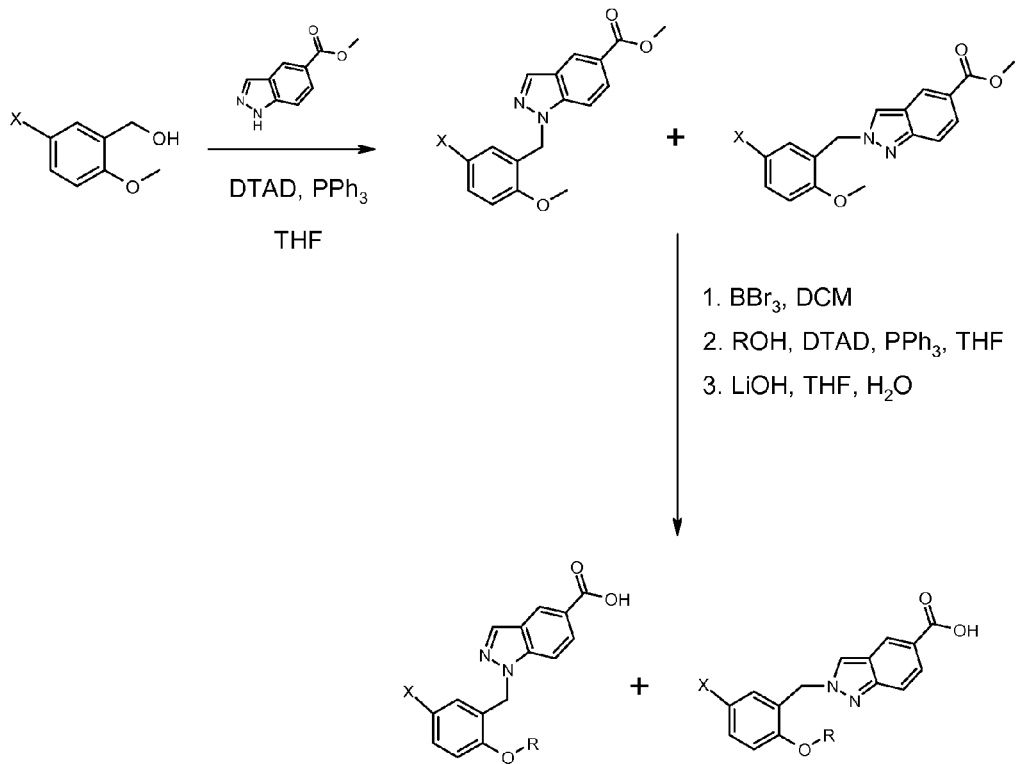
Figure 3:
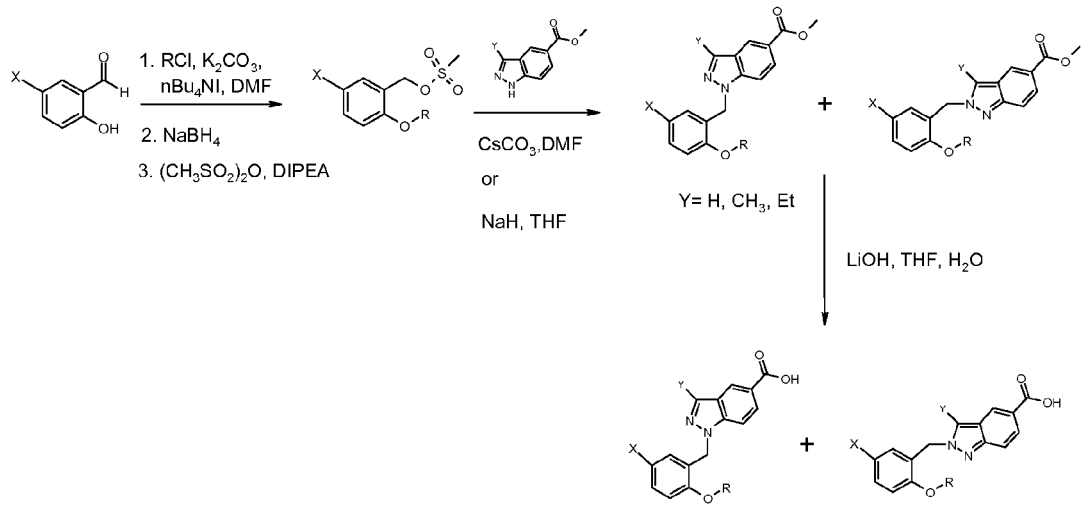
Figure 4:
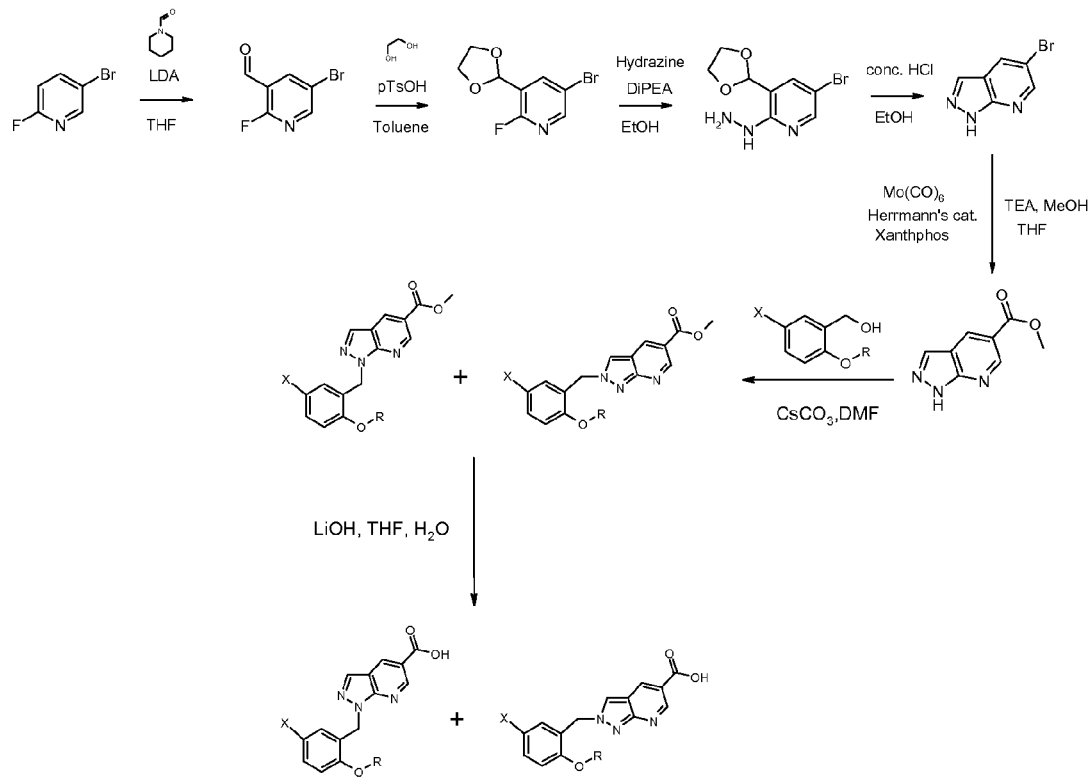

FIGS. 1, 2, 3 and 4 show reaction schemes for the preparation of the compounds of this invention.

DETAILED DESCRIPTION OF THE INVENTION

The following terms are used to define the disclosed invention.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Alkyl" refers to a straight-chain, branched or cyclic saturated aliphatic hydrocarbon. Preferably, the alkyl group has 1 to 12 carbons. More preferably, it is an alkyl of from 4 to 10 carbons, most preferably 4 to 8 carbons. Typical alkyl groups include methyl, ethyl, propyl, isopropyl, butyl, isobutyl, tertiary butyl, pentyl, hexyl and the like. The alkyl group may be optionally substituted with one or more substituents selected from the group consisting of hydroxyl, cyano, alkoxy, =O, =S, NO$_2$, halogen, dimethyl amino, and SH.

"Cycloalkyl" refers to a cyclic saturated aliphatic hydrocarbon group. Preferably, the cycloalkyl group has 3 to 12 carbons. More preferably, it has from 4 to 7 carbons, most preferably 5 or 6 carbons.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of alkyl, hydroxyl, halogen, COOR$^6$, NO$_2$, CF$_3$, N(R$^6$)$_2$, CON(R$^6$)$_2$, SR$^6$, sulfoxy, sulfone, CN and OR$^6$, wherein R$^6$ is alkyl.

"Carbocyclic aryl" refers to an aryl group wherein the ring atoms are carbon.

"Heteroaryl or heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like. Preferably, the heteroaryl group has from 2 to 10 carbons. More preferably, it has from 3 to 10 carbons, most preferably 3 carbons.

Pharmaceutical compositions contemplated herein include compositions wherein the active ingredient is contained in an effective amount, i.e., in an amount effective to achieve its intended purpose. An "effective amount" is an amount sufficient to accomplish a stated purpose (e.g., achieve the effect for which it is administered, treat a disease, reduce one or more symptoms of a disease or condition). An example of an "effective amount" is an amount sufficient to contribute to the treatment, prevention, or reduction of a symptom or symptoms of a disease, which can be referred to as a "therapeutically effective amount." A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated.

"Treatment", "treat" or "treating" can refer to curing any disease or condition or reducing or alleviating the symptoms of the disease or condition.

The present invention provides compounds having the general formula I:

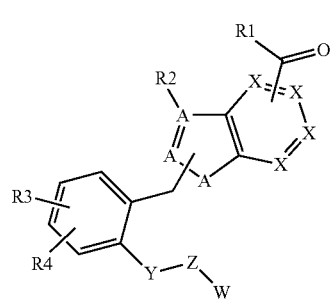

wherein X is N or CR$_7$ independently;
A is N or CR$_7$ with the proviso that at least one A is N and when each A is N, R$_2$ is absent;
Y is (CH$_2$)$_m$ wherein m is 0 or an integer of from 1 to 3;

Z is selected from the group consisting of O, S, SO, SO$_2$ and (CH$_2$)$_p$, wherein p is 0 or an integer of from 1 to 3;

W is hydrocarbyl or substituted hydrocarbyl:

R$_1$ is selected from the group consisting of OR$_7$, N(R$_7$)$_2$, and N(R$_7$)SO$_2$R$_7$;

R$_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

R$_3$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

R$_4$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and R$_7$ is selected from the group consisting of H, hydrocarbyl and substituted hydrocarbyl, e.g. carbocyclic aryl and alkyl.

More preferably, the compound of the invention is represented by the formula II:

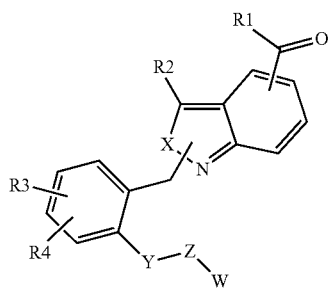

Most preferably, the compound of the invention is represented by the formula III:

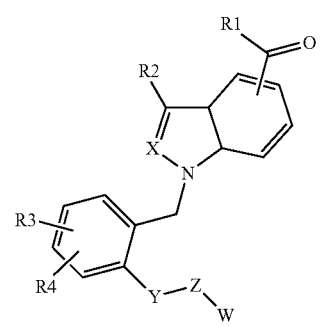

Preferably, R$_1$ is OH;

Preferably, R$_2$ is selected from the group consisting of H, alkyl and halogen substituted alkyl, e.g. fluoro-substituted alkyl;

Preferably, X is N or CH;

Preferably, R$_3$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy. More preferably R$_3$ is chloro or bromo;

Preferably, R$_4$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy. More preferably R$_4$ is H;

Preferably, Y is absent, i.e. n is 0;

Preferably, Z is O;

Preferably, W is selected from the group consisting of alkyl, aryl, alkoxy, aryloxy and hydroxyl, halogen, nitro, amino and cyano-substituted alkyl, aryl, alkoxy or aryloxy;

More preferably W is selected from the group consisting of alkyl, e.g. branched chain alkyl such as 2-ethylbutyl, 2-methylpropyl, etc.

The most preferred compounds of the present invention are selected from the group consisting of:

1-[5-Chloro-2-(2-ethyl-butoxy)-benzyl]-1H-indole-5-carboxylic acid;
1-[5-Chloro-2-(2-ethyl-butoxy)-benzyl]-1H-indazole-5-carboxylic acid;
1-(2-Chloro-5-isobutoxy-benzyl)-1H-indazole-5-carboxylic acid;
1-(2-Bromo-5-isobutoxy-benzyl)-1H-indazole-5-carboxylic acid;
1-[2-Bromo-5-(2-ethyl-butoxy)-benzyl]-1H-indazole-5-carboxylic acid;
1-[2-Chloro-5-(2-ethyl-butoxy)-benzyl]-1H-indazole-6-carboxylic acid;
1-(5-Bromo-2-isobutoxy-benzyl)-1H-indazole-4-carboxylic acid;
1-(2-Benzyloxy-5-chloro-benzyl)-1H-indazole-5-carboxylic acid;
1-[5-Chloro-2-(4-chloro-benzyloxy)-benzyl]-1H-indazole-5-carboxylic acid;
1-(5-Chloro-2-cyclopentylmethoxy-benzyl)-1H-indazole-5-carboxylic acid;
1-(5-Chloro-2-cyclopropylmethoxy-benzyl)-1H-indazole-5-carboxylic acid;
1-(2-Benzyloxy-5-bromo-benzyl)-1H-indazole-5-carboxylic acid;
1-[5-Bromo-2-(4-chloro-benzyloxy)-benzyl]-1H-indazole-5-carboxylic acid;
1-(5-Bromo-2-cyclopentylmethoxy-benzyl)-1H-indazole-5-carboxylic acid;
1-(5-Bromo-2-cyclopropylmethoxy-benzyl)-1H-indazole-5-carboxylic acid;
2-(5-Chloro-2-isobutoxy-benzyl)-2H-indazole-5-carboxylic acid;
2-(5-Bromo-2-isobutoxy-benzyl)-2H-indazole-5-carboxylic acid;
1-(2-(Trifluoromethyl)-5-isobutoxy-benzyl)-1H-indazole-5-carboxylic acid;
1-(5-Bromo-2-cyclopropyl-2-methylmethoxy-benzyl)-1H-indazole-5-carboxylic acid;
1-(2-Isobutoxy-5-trifluoromethoxy-benzyl)-1H-indazole-5-carboxylic acid;
1-(5-Bromo-2-isobutoxy-benzyl)-3-methyl-1H-indazole-5-carboxylic acid;
1-(2-isobutoxy-5-trifluoromethoxy-benzyl)-3-methyl-1 h-indazole-5-carboxylic acid;
1-[5-chloro-2-(2-ethyl-butoxy)-benzyl]-3-methyl-1 h-indazole-5-carboxylic acid;
1-(5-chloro-2-isobutoxy-benzyl)-3-methyl-1 h-indazole-5-carboxylic acid;
1-(2-isobutoxy-5-trifluoromethyl-benzyl)-3-methyl-1 h-indazole-5-carboxylic acid;
1-[2-(2-ethyl-butoxy)-5-trifluoromethyl-benzyl]-3-methyl-1 h-indazole-5-carboxylic acid;
1-[5-bromo-2-(2-ethyl-butoxy)-benzyl]-3-methyl-1 h-indazole-5-carboxylic acid;

1-[5-bromo-2-(1-methyl-cyclopropylmethoxy)-benzyl]-3-methyl-1h-indazole-5-carboxylic acid;
1-[5-chloro-2-(1-methyl-cyclopropylmethoxy)-benzyl]-3-methyl-1h-indazole-5-carboxylic acid;
1-(5-Bromo-2-isobutoxy-benzyl)-1H-pyrrolo[2,3-b]pyridine-5-carboxylic acid;
1-[5-Bromo-2-(2-ethyl-butoxy)-benzyl]-1H-pyrrolo[2,3-b]pyridine-5-carboxylic acid;
1-[2-(4-Chloro-benzyloxy)-5-trifluoromethyl-benzyl]-1H-indazole-5-carboxylic acid;
1-(2-Cyclopentylmethoxy-5-trifluoromethyl-benzyl)-1H-indazole-5-carboxylic acid;
1-(5-Chloro-2-cyclopropylmethoxy-benzyl)-1H-indazole-4-carboxylic acid;
2-(5-Chloro-2-cyclopropylmethoxy-benzyl)-2H-indazole-4-carboxylic acid;
1-(5-Chloro-2-isobutoxy-benzyl)-1H-indazole-4-carboxylic acid;
2-(5-Chloro-2-isobutoxy-benzyl)-2H-indazole-4-carboxylic acid;
1-[5-Chloro-2-(2-ethyl-butoxy)-benzyl]-1H-indazole-4-carboxylic acid;
2-[5-Chloro-2-(2-ethyl-butoxy)-benzyl]-2H-indazole-4-carboxylic acid;
1-[5-Chloro-2-(4-chloro-benzyloxy)-benzyl]-1H-indazole-4-carboxylic acid;
2-[5-Chloro-2-(4-chloro-benzyloxy)-benzyl]-2H-indazole-4-carboxylic acid;
1-(5-Bromo-2-isobutoxy-benzyl)-1H-indazole-6-carboxylic acid;
2-(5-Bromo-2-isobutoxy-benzyl)-2H-indazole-6-carboxylic acid;
1-(5-Bromo-2-cyclopentylmethoxy-benzyl)-1H-indazole-6-carboxylic acid;
2-(5-Bromo-2-cyclopentylmethoxy-benzyl)-2H-indazole-6-carboxylic acid;
1-[5-Chloro-2-(2-ethyl-butoxy)-benzyl]-1H-indazole-6-carboxylic acid;
1-(5-Chloro-3-fluoro-2-isobutoxy-benzyl)-1H-indazole-5-carboxylic acid;
1-(2-Isobutoxy-5-methanesulfonyl-benzyl)-1H-indazole-5-carboxylic acid;
1-(4,5-Dichloro-2-isobutoxy-benzyl)-1H-indazole-5-carboxylic acid;
1-(3-Isobutoxy-6-methyl-pyridin-2-ylmethyl)-1H-indazole-5-carboxylic acid;
1-[5-Bromo-2-(1-ethyl-propoxy)-benzyl]-1H-indazole-5-carboxylic acid;
1-[5-Bromo-2-(2,2-dimethyl-propoxy)-benzyl]-1H-indazole-5-carboxylic acid;
1-[5-Bromo-2-(2-hydroxy-2-methyl-propoxy)-benzyl]-1H-indazole-5-carboxylic acid;
1-(5-Hydroxy-2-isobutoxy-benzyl)-1H-indazole-5-carboxylic acid;
1-[5-(2,2-Difluoro-ethoxy)-2-isobutoxy-benzyl]-1H-indazole-5-carboxylic acid;
1-(5-Difluoromethoxy-2-isobutoxy-benzyl)-1H-indazole-5-carboxylic acid;
1-(5-Chloro-2-isobutoxy-benzyl)-1H-pyrazolo[3,4-b]pyridine-5-carboxylic acid;
1-(2-Isobutoxy-5-trifluoromethoxy-benzyl)-1H-pyrazolo[3,4-b]pyridine-5-carboxylic acid;
1-[5-Bromo-2-(2-ethyl-butoxy)-benzyl]-3-methyl-1H-pyrazolo[3,4-b]pyridine-5-carboxylic acid;
1-[5-CHLORO-2-(2-ethyl-butoxy)-benzyl]-3-methyl-1H-pyrazolo[3,4-b]pyridine-5-carboxylic acid;
1-(5-Chloro-2-isobutoxy-benzyl)-3-methyl-1H-pyrazolo[3,4-b]pyridine-5-carboxylic acid;
1-[5-chloro-2-(2-ethyl-butoxy)-benzyl]-1h-pyrazolo[3,4-c]pyridine-5-carboxylic acid amide;
1-[5-chloro-2-(2-ethyl-butoxy)-benzyl]-1h-pyrazolo[3,4-c]pyridine-5-carboxylic acid;
1-(5-bromo-2-isobutoxy-benzyl)-3-ethyl-1h-indazole-5-carboxylic acid;
1-[5-bromo-2-(2-ethyl-butoxy)-benzyl]-3-ethyl-1h-indazole-5-carboxylic acid;
1-(5-bromo-2-isobutoxy-benzyl)-2-methyl-1h-indole-5-carboxylic acid;
1-(5-bromo-2-isobutoxy-benzyl)-1h-indole-5-carboxylic acid;
1-[5-bromo-2-(2-ethyl-butoxy)-benzyl]-2-methyl-1h-indole-5-carboxylic acid;
1-[5-bromo-2-(2-ethyl-butoxy)-benzyl]-1h-indole-5-carboxylic acid;
1-[5-bromo-2-(2-ethyl-butoxy)-benzyl]-1h-indole-6-carboxylic acid;
1-(2-isobutoxy-5-trifluoromethoxy-benzyl)-1h-indole-5-carboxylic acid;
1-(5-bromo-2-isobutoxy-benzyl)-1h-pyrrolo[2,3-b]pyridine-5-carboxylic acid;
1-(5-bromo-2-isobutoxy-benzyl)-1h-pyrrolo[3,2-b]pyridine-5-carboxylic acid;
1-(2-isobutoxy-5-trifluoromethoxy-benzyl)-1h-pyrrolo[2,3-b]pyridine-5-carboxylic acid;
1-(2-isobutoxy-5-trifluoromethoxy-benzyl)-3-methyl-1h-indole-5-carboxylic acid;
1-[2-(2-ethyl-butoxy)-5-trifluoromethoxy-benzyl]-1h-pyrrolo[2,3-b]pyridine-5-carboxylic acid;
1-[2-(2-ethyl-butoxy)-5-trifluoromethoxy-benzyl]-3-methyl-1h-indole-5-carboxylic acid;
1-[5-bromo-2-(2-ethyl-butoxy)-benzyl]-1h-benzoimidazole-5-carboxylic acid;
1-(5-bromo-2-isobutoxy-benzyl)-1h-benzoimidazole-5-carboxylic acid;
1-[5-Chloro-2-(2-ethyl-butoxy)-benzyl]-1H-indazole-5-carboxylic acid;
1-(2-Chloro-5-isobutoxy-benzyl)-1H-indazole-5-carboxylic acid;
1-(2-Bromo-5-isobutoxy-benzyl)-1H-indazole-5-carboxylic acid;
1-[2-Bromo-5-(2-ethyl-butoxy)-benzyl]-1H-indazole-5-carboxylic acid;
1-[2-Chloro-5-(2-ethyl-butoxy)-benzyl]-1H-indazole-6-carboxylic acid;
1-(5-Bromo-2-isobutoxy-benzyl)-1H-indazole-4-carboxylic acid;
1-(2-Benzyloxy-5-chloro-benzyl)-1H-indazole-5-carboxylic acid;
1-[5-Chloro-2-(4-chloro-benzyloxy)-benzyl]-1H-indazole-5-carboxylic acid;
1-(5-Chloro-2-cyclopentylmethoxy-benzyl)-1H-indazole-5-carboxylic acid;
1-(5-Chloro-2-cyclopropylmethoxy-benzyl)-1H-indazole-5-carboxylic acid;
1-(2-Benzyloxy-5-bromo-benzyl)-1H-indazole-5-carboxylic acid;
1-[5-Chloro-2-(4-chloro-benzyloxy)-benzyl]-1H-indazole-5-carboxylic acid;
1-(5-Chloro-2-cyclopentylmethoxy-benzyl)-1H-indazole-5-carboxylic acid;
1-(5-Bromo-2-cyclopropylmethoxy-benzyl)-1H-indazole-5-carboxylic acid;

2-(5-Chloro-2-isobutoxy-benzyl)-2H-indazole-5-carboxylic acid;

2-(5-Bromo-2-isobutoxy-benzyl)-2H-indazole-5-carboxylic acid;

1-(2-(Trifluoromethyl)-5-isobutoxy-benzyl)-1H-indazole-5-carboxylic acid;

1-(5-Bromo-2-cyclopropyl-2-methylmethoxy-benzyl)-1H-indazole-5-carboxylic acid;

1-(2-Isobutoxy-5-trifluoromethoxy-benzyl)-1H-indazole-5-carboxylic acid;

1-(5-Bromo-2-isobutoxy-benzyl)-3-methyl-1H-indazole-5-carboxylic acid;

1-(5-Bromo-2-isobutoxy-benzyl)-1H-pyrrolo[2,3-b]pyridine-5-carboxylic acid; and, 1-[5-Bromo-2-(2-ethyl-butoxy)-benzyl]-1H-pyrrolo[2,3-b]pyridine-5-carboxylic acid.

As shown in FIGS. 1, 2, 3 and 4, the compounds of the present invention may be prepared by the methods disclosed in the Examples.

The following examples are intended to illustrate the present invention.

The reagents and conditions used in FIGS. 1, 2, 3 and 4 and the examples may be abbreviated as follows:

Ac is acetyl;
DCM is dichloromethane;
DTAD is Di-tert-butyl azodicarboxylate;
TFA is trifluoroacetic acid;
RT is room temperature;
Ph is phenyl;
DiBAL-H is diisobutylaluminumhydride;
DMF is dimethylformamide;
Et is ethyl;
THF is tetrahydrofuran;
DMAP is 4-dimethylaminopyridine;
HEPES is 4-(2-hydroxyethyl)-1-piperazineethanesulfonic acid).

EXAMPLE 1

1-[5-Chloro-2-(2-Ethyl-Butoxy)-Benzyl]-1H-Indole-5-Carboxylic Acid

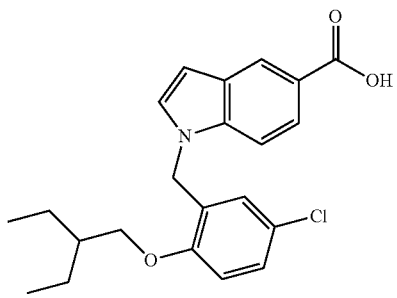 [SMILES: CCC(CC)COc1ccc(Cl)cc1Cn1ccc2cc(C(=O)O)ccc21]

Step 1

2-Bromomethyl-1-chloro-4-(2-ethyl-butoxy)-benzene 1

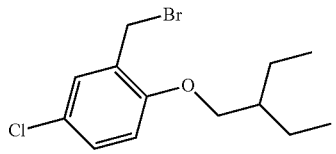 [SMILES: CCC(CC)COc1ccc(Cl)cc1CBr]

To a solution of 4-chloro-2-methylphenol 5 g (35 mmol) in DMF (75 mL) were added potassium carbonate 10 g (70 mmol), tetrabutylammonium iodide 0.5 g (1.4 mmol) and 3-chloromethylpentane 7.7 ml (52.6 mmol). The resulting mixture was refluxed for 20 hours. The mixture was poured into 2M NaOH solution and extracted with EtOAC. The organic layers were combined, washed with aqueous HCl and with brine, dried (MgSO$_4$) and the volatiles were removed in vacuo. The crude product (5.1 g) was used without further purification. LC-MS: m/z 227 M+H$^+$.

A solution of 1-chloro-4-(2-ethyl-butoxy)-2-methyl-benzene (5.1 g, 22.5 mmol), N-bromosuccinimide (4.8 g, 27 mmol) and benzoylperoxide (0.27 g, 1.1 mmol) in CCl$_4$ (50 mL) was refluxed under illumination from a high energy lamp for 3 hours. The reaction mixture was cooled to room temperature and partitioned between water (50 mL) and CH$_2$Cl$_2$ (25 mL). The aqueous layer was extracted with CH$_2$Cl$_2$ (25 mL). The combined organic layers were washed with water (2×75 mL), dried (Na$_2$SO$_4$) and evaporated to dryness to give bromide 1 as a light brown oil, 3.9 g (57%).
$^1$H-NMR (CDCl$_3$, 300 MHz) δ7.25 (m, 2H, ArH), 6.80 (dd, 1H, ArH), 4.50 (s, 2H, ArCH), 3.93 (dd, 2H, CH$_2$), 1.73 (m, 1H, —CH), 1.54 (m, 4H, —CH$_2$), 0.94 (m, 6H —CH$_3$).
LC-MS: m/z 306 M+H$^+$ Step 2

1-[5-Chloro-2-(2-ethyl-butoxy)-benzyl]-1h-indole-5-carboxylic acid methyl ester 2

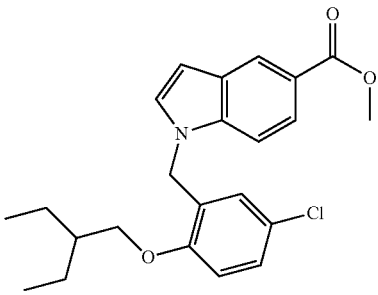 [SMILES: CCC(CC)COc1ccc(Cl)cc1Cn1ccc2cc(C(=O)OC)ccc21]

To a solution of 2-bromomethyl-1-chloro-4-(2-ethyl-butoxy)-benzene 1 0.11 g (0.63 mmol) in DMF (2.5 mL) were added potassium carbonate 0.24 g (1.74 mmol), tetrabutylammonium iodide 0.02 g and methyl indole-5-carboxylate 0.22 g (1.26 mmol). The resulting mixture was heated at 150° C. in an Emrys microwave reactor for 20 minutes. The mixture was poured into water and extracted with EtOAc. The organic layers were combined, washed with aqueous HCl (20 ml, 2M) and with brine (20 mL), dried (MgSO₄) and the volatiles were removed in vacuo. The crude product was purified on silica to yield 1-[5-Chloro-2-(2-ethyl-butoxy)-benzyl]-1H-indole-5-carboxylic acid methyl ester 2 0.04 g as a white solid (16%).

¹H-NMR (CDCl₃, 300 MHz) δ 8.43 (d, 1H, ArH), 7.91 (dd, 1H, ArH), 7.32 (d, 1H, ArH), 7.19 (dd, 2H, ArH), 6.85 (d, 1H, ArH), 6.70 (dd, 1H, ArH), 6.66 (dd, 1H, ArH), 5.31 (s, 2H, ArCH₂), 3.95 (s, 2H, CH₃), 3.94 (dd, 2H, CH₂) 1.70 (m, 1H, CH), 1.47 (m, 4H, CH₂), 0.95 (m, 6H, CH₃). LC-MS: m/z 400 M+H⁺.

Step 3

1-[5-Chloro-2-(2-ethyl-butoxy)-benzyl]-1H-indole-5-carboxylic acid 3

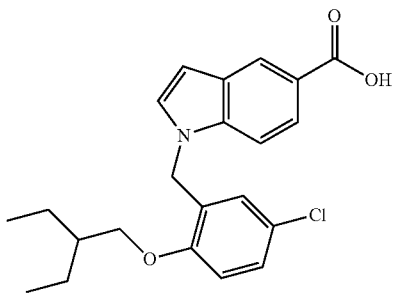 [SMILES: CCC(CC)COc1ccc(Cl)cc1Cn1ccc2cc(C(=O)O)ccc21]

To a solution of 1-[5-chloro-2-(2-ethyl-butoxy)-benzyl]-1H-indole-5-carboxylic acid methyl ester 2 0.04 g (0.1 mmol) in a mixture of THF (2 mL) and methanol (1 ml) was added a solution of LiOH (0.12 g in 0.7 ml H₂O). The resulting mixture was heated at 100° C. in an Emrys microwave reactor for 10 minutes. The mixture was poured into water (20 mL) and extracted with EtOAc (3×15 mL). The organic layers were combined, washed with brine (30 mL), dried (MgSO₄) and the volatiles were removed in vacuo. The crude product was purified on silica to yield 21.9 mg (57%) of 1-[5-Chloro-2-(2-ethyl-butoxy)-benzyl]-1H-indole-5-carboxylic acid 3 as a white solid.

¹H-NMR (CDCl₃, 8.54 (s, 1H, ArH), 7.99 (dd, 1H, ArH), 7.37 (dd, 1H, ArH), 7.20 (dd, 2H, ArH), 6.86 (d, 1H, ArH), 6.74 (dd, 1H, ArH), 6.70 (dd, 1H, ArH), 5.33 (s, 2H, ArCH₂), 3.92 (dd, 2H, CH₂) 1.70 (m, 1H, CH), 1.47 (m, 4H, CH₂), 0.95 (m, 6H, CH₃). LC-MS: m/z 386 M+H⁺.

EXAMPLE 2

1-[5-Chloro-2-(2-Ethyl-Butoxy)-Benzyl]-1H-Indazole-5-Carboxylic Acid 6

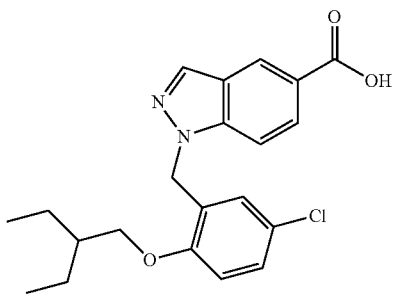

Step 1

1H-Indazole-5-carboxylic acid methyl ester 4

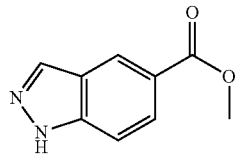

A solution of 1H-indazole-5-carboxylic acid 0.25 g (1.54 mmol) in methanol (2.5 mL) and conc. H₂SO₄ (0.1 ml) was heated at 100° C. in an Emrys microwave reactor for 5 minutes. The mixture was poured into water (20 mL) and extracted with EtOAc (3×15 mL). The organic layers were combined, washed with saturated NaHCO₃ and brine (30 mL), dried (MgSO₄) and the volatiles were removed in vacuo to yield of 1H-indazole-5-carboxylic acid methyl ester 0.086 g (32%) 4 as a pale yellow solid.

¹H-NMR (CDCl₃, δ 8.58 (dd, 1H, ArH), 8.21 (d, 1H, ArH), 8.11 (dd, 1H, ArH), 7.54 (d, 2H, ArH), 3.98 (s, 3H, CH₃).

LC-MS: m/z 177 M+H⁺.

Step 2

1-[5-Chloro-2-(2-ethyl-butoxy)-benzyl]-1H-indazole-5-carboxylic acid methyl ester, 5

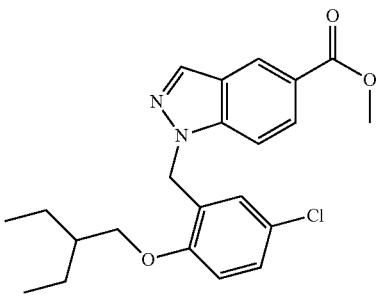 [SMILES: CCC(CC)COc1ccc(Cl)cc1Cn1ncc2cc(C(=O)OC)ccc21]

The title compound was prepared following the method in Example 1, Step 2.

¹H-NMR (CDCl₃, 300 MHz) δ 8.55 (dd, 1H, ArH), 8.18 (d, 1H, ArH), 8.05 (dd, 1H, ArH), 7.40 (d, 1H, ArH), 7.20 (dd, 1H, ArH), 6.84 (d, 1H, ArH), 6.80 (dd, 1H, ArH), 5.60 (s, 2H, ArCH₂), 3.97 (s, 3H, CH₃), 3.91 (dd, 2H, CH₂) 1.70 (m, 1H, CH), 1.47 (m, 4H, CH₂), 0.94 (m, 6H, CH₃). LC-MS: m/z 401 M+H⁺.

Step 3

1-[5-Chloro-2-(2-ethyl-butoxy)-benzyl]-1H-indazole-5-carboxylic acid, 6

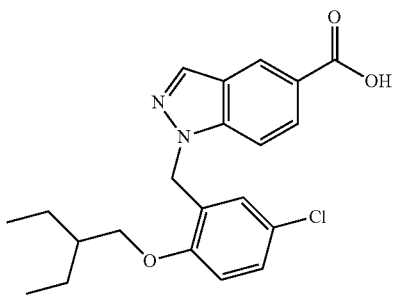 [SMILES: CCC(CC)COc1ccc(Cl)cc1Cn1ncc2cc(C(=O)O)ccc21]

The title compound was prepared following the method in Example 1, Step 3.

$^1$H-NMR (CDCl$_3$, 300 MHz) δ 8.66 (dd, 1H, ArH), 8.22 (d, 1H, ArH), 8.11 (dd, 1H, ArH), 7.45 (d, 1H, ArH), 7.21 (dd, 1H, ArH), 6.85 (dd, 1H, ArH), 6.83 (d, 1H, ArH), 5.62 (s, 2H, ArCH$_2$), 3.91 (d, 2H, CH$_2$) 1.70 (m, 1H, CH), 1.47 (m, 4H, CH$_2$), 0.95 (m, 6H, CH$_3$).

LC-MS: m/z 387 M+H$^+$.

EXAMPLE 3

1-(2-Chloro-5-Isobutoxy-Benzyl)-1H-Indazole-5-Carboxylic Acid, 10

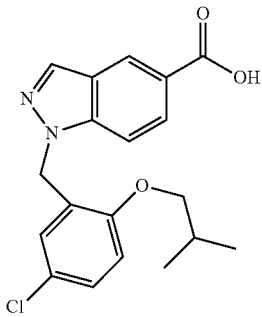 [SMILES: CC(C)COc1ccc(Cl)cc1Cn1ncc2cc(C(=O)O)ccc21]

Step 1

1-(5-Chloro-2-methoxy-benzyl)-1H-indazole-5-carboxylic acid methyl ester, 7

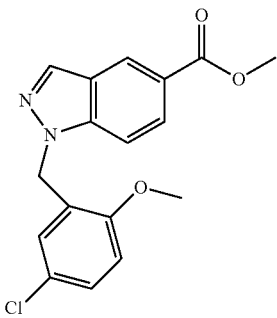 [SMILES: COC(=O)c1ccc2c(cnn2Cc2cc(Cl)ccc2OC)c1]

A solution of 1H-indazole-5-carboxylic acid methyl ester, 4, (0.05 g 0.28 mmol), triphenylphosphine (0.11 g, 0.43 mmol), di-tert-butylazodicarboxylate (0.1 g, 0.43 mmol) and (5-chloro-2-methoxy-phenyl)-methanol, (0.075 g, 0.43 mmol) in a mixture of THF (1 mL) and toluene (1 ml) was heated at 120° C. in an Emrys microwave reactor for 20 min. The volatiles were removed in vacuo. The crude product was purified on silica to yield 1-(5-chloro-2-methoxy-benzyl)-1H-indazole-5-carboxylic acid methyl ester, 7. 0.035 g (38%).

$^1$H-NMR (CDCl$_3$, 300 MHz) δ 8.54 (s, 1H, ArH), 8.17 (s, 1H, ArH), 8.07 (dd, 1H, ArH), 7.47 (dd, 1H, ArH), 7.22 (dd, 1H, ArH), 6.90 (d, 1H, ArH), 6.83 (dd, 1H, ArH), 5.59 (s, 2H, ArCH$_2$), 3.97 (s, 3H, CH$_3$), 3.86 (s, 3H, CH$_3$).

Step 2

1-(2-Chloro-5-hydroxy-benzyl)-1H-indazole-5-carboxylic acid methyl ester, 8

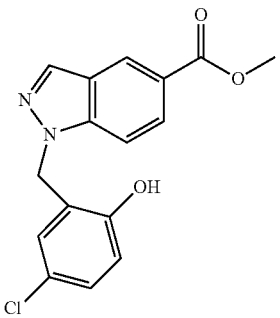 [SMILES: COC(=O)c1ccc2c(cnn2Cc2cc(Cl)ccc2O)c1]

To a solution of 1-(5-chloro-2-methoxy-benzyl)-1H-indazole-5-carboxylic acid methyl ester, 8, 0.09 g (0.27 mmol) in dry DCM (10 ml) under N$_2$ atm at 0° C., 2.0 ml of boron tribromide (1M in DCM) was added. and the solution was allowed to warm to room temperature. The mixture was stirred for 24 hours, quenched with MeOH and refluxed for 3 hours. After cooling to room temperature, water was added and the mixture was extracted with EtOAc and washed with brine. After drying over MgSO$_4$, the solvents were removed in vacuo to yield 0.05 g of 1-(2-chloro-5-hydroxy-benzyl)-1H-indazole-5-carboxylic acid methyl ester, 8.

$^1$H-NMR (CDCl$_3$, 300 MHz) δ 8.36 (s, 1H, ArH), 8.13 (s, 1H, ArH), 7.84 (m, 2H, ArH), 7.28 (d, 1H, ArH), 7.19 (dd, 1H, ArH), 6.93 (d, 1H, ArH), 5.52 (s, 2H, ArCH$_2$), 4.03 (s, 3H, CH$_3$).

LC-MS: m/z 317 M+H$^+$.

Step 3

1-(2-Chloro-5-isobutoxy-benzyl)-1H-indazole-5-carboxylic acid methyl ester, 9

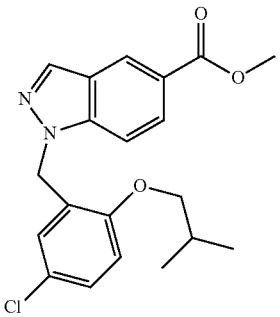 [SMILES: COC(=O)c1ccc2c(cnn2Cc2cc(Cl)ccc2OCC(C)C)c1]

A solution of 1-(2-Chloro-5-hydroxy-benzyl)-1H-indazole-5-carboxylic acid methyl ester 8 (0.1 g g 0.33 mmol), triphenylphosphine (0.173 g, 0.66 mmol), di-tert-butylazodicarboxylate (0.15 g, 0.66 mmol) and 2-methyl-1-propanol (0.061 mL, 0.66 mmol) in THF (3 mL) was at 120° C. on microwave for 20 min. The volatiles were removed in vacuo. The crude product was purified on silica to yield 1-(2-chloro-5-isobutoxy-benzyl)-1H-indazole-5-carboxylic acid methyl ester, 9.

0.09 g (73%).

$^1$H-NMR (CDCl$_3$, 300 MHz) δ8.55 (s, 1H, ArH), 8.18 (s, 1H, ArH), 8.05 (dd, 1H, ArH), 7.43 (d, 1H, ArH), 7.20 (dd, 1H, ArH), 6.83 (s, 1H, ArH), 6.81 (d, 1H, ArH), 5.62 (s, 2H, ArCH$_2$), 3.97 (s, 3H, CH$_3$), 3.77 (d, 2H, CH$_2$). 2.11 (m, 1H, CH), 1.04 (d, 6H, CH$_3$).

LC-MS: m/z 373 M+H$^+$.

Step 4

1-(2-Chloro-5-isobutoxy-benzyl)-1H-indazole-5-carboxylic acid, 10

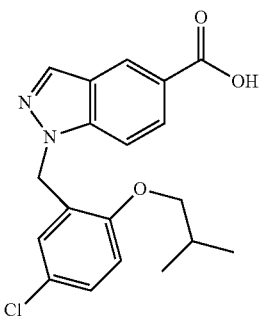 [SMILES: CC(C)COc1ccc(Cl)cc1Cn1ncc2cc(C(=O)O)ccc21]

The title compound was prepared following the method in Example 1, Step 3.

$^1$H-NMR (CDCl$_3$, 300 MHz) δ 8.64 (s, 1H, ArH), 8.22 (s, 1H, ArH), 8.11 (dd, 1H, ArH), 7.47 (d, 1H, ArH), 7.21 (dd, 1H, ArH), 6.86 (d, 1H, ArH), 6.82 (d, 1H, ArH), 5.63 (s, 2H, ArCH$_2$), 3.78 (d, 2H, CH$_2$). 2.10 (m, 1H, CH), 1.04 (d, 6H, CH$_3$).

LC-MS: m/z 359 M+H$^+$.

EXAMPLE 4

1-(2-Bromo-5-Isobutoxy-Benzyl)-1H-Indazole-5-Carboxylic Acid, 14

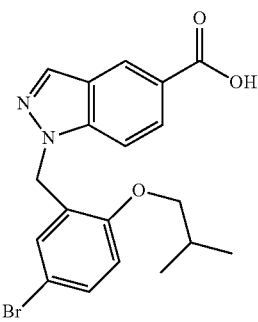

Step 1

1-(5-Bromo-2-methoxy-benzyl)-1H-indazole-5-carboxylic acid methyl ester, 11

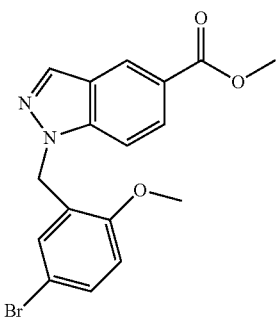

The title compound was prepared following the method in Example 3, Step 1. But using (5-bromo-2-methoxy-phenyl)-methanol, instead of (5-chloro-2-methoxy-phenyl)-methanol, $^1$H-NMR (CDCl$_3$, 300 MHz) δ 8.54 (s, 1H, ArH), 8.17 (s, 1H, ArH), 8.07 (dd, 1H, ArH), 7.47 (dd, 1H, ArH), 7.22 (dd, 1H, ArH), 6.90 (d, 1H, ArH), 6.83 (dd, 1H, ArH), 5.59 (s, 2H, ArCH$_2$), 3.97 (s, 3H, CH$_3$), 3.86 (s, 3H, CH$_3$).

LC-MS: m/z 376 M+H$^+$.

Step 2

1-(2-Bromo-5-hydroxy-benzyl)-1H-indazole-5-carboxylic acid methyl ester, 12

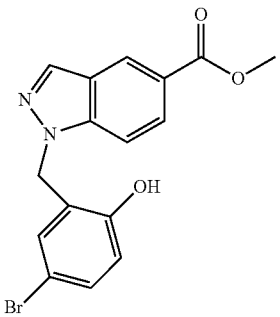

The title compound was prepared following the method in Example 3, Step 2.

$^1$H-NMR (CDCl$_3$, 300 MHz) δ 8.56 (s, 1H, ArH), 8.18 (dd, 1H, ArH), 8.16 (dd, 1H, ArH), 7.58 (d, 1H, ArH), 7.42 (d, 1H, ArH), 7.35 (dd, 1H, ArH), 6.90 (d, 1H, ArH), 5.47 (s, 2H, ArCH$_2$), 3.97 (s, 3H, CH$_3$).

LC-MS: m/z 362 M+H$^+$.

Step 3

1-(2-Bromo-5-isobutoxy-benzyl)-1H-indazole-5-carboxylic acid methyl ester, 13

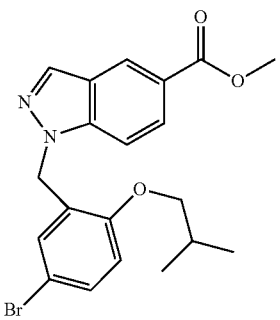

The title compound was prepared following the method in Example 3, Step 3.

$^1$H-NMR (CDCl$_3$, 300 MHz) δ 8.55 (s, 1H, ArH), 8.17 (s, 1H, ArH), 8.06 (dd, 1H, ArH), 7.43 (d, 1H, ArH), 7.35 (dd, 1H, ArH), 6.99 (d, 1H, ArH), 6.76 (d, 1H, ArH), 5.61 (s, 2H, ArCH$_2$), 3.97 (s, 3H, CH$_3$), 3.76 (d, 2H, CH$_2$). 2.11 (m, 1H, CH), 1.03 (d, 6H, CH$_3$).

LC-MS: m/z 418 M+H$^+$.

Step 4

1-(2-Bromo-5-isobutoxy-benzyl)-1H-indazole-5-carboxylic acid, 14

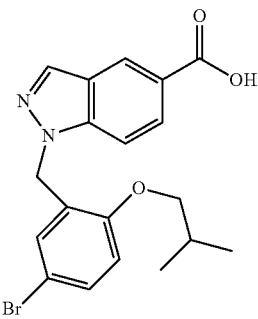

The title compound was prepared following the method in Example 1, Step 3.

$^1$H-NMR (CDCl$_3$, 300 MHz) δ 8.65 (s, 1H, ArH), 8.21 (s, 1H, ArH), 8.11 (dd, 1H, ArH), 7.48 (d, 1H, ArH), 7.36 (dd, 1H, ArH), 7.02 (d, 1H, ArH), 6.77 (d, 1H, ArH), 5.63 (s, 2H, ArCH$_2$), 3.77 (d, 2H, CH$_2$). 2.11 (m, 1H, CH), 1.03 (d, 6H, CH$_3$), LC-MS: m/z 404 M+H$^+$.

EXAMPLE 5

1-[2-Bromo-5-(2-Ethyl-Butoxy)-Benzyl]-1H-Indazole-5-Carboxylic Acid, 16

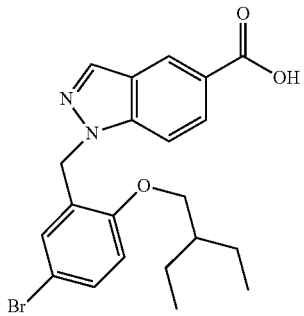 [SMILES: CCC(CC)COc1ccc(Br)cc1Cn1ncc2cc(C(=O)O)ccc21]

Step 1

1-[2-Bromo-5-(2-ethyl-butoxy)-benzyl]-1H-indazole-5-carboxylic acid methyl ester, 15

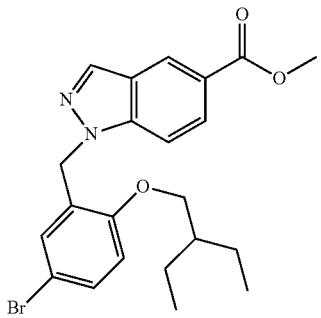 [SMILES: CCC(CC)COc1ccc(Br)cc1Cn1ncc2cc(C(=O)OC)ccc21]

The title compound was prepared following the method in Example 3, Step 3.

$^1$H-NMR (CDCl$_3$, 300 MHz) δ 8.55 (s, 1H, ArH), 8.18 (s, 1H, ArH), 8.05 (dd, 1H, ArH), 7.41 (d, 1H, ArH), 7.35 (dd, 1H, ArH), 6.95 (d, 1H, ArH), 6.80 (d, 1H, ArH), 5.60 (s, 2H, ArCH$_2$), 3.97 (s, 3H, CH$_3$), 3.90 (d, 2H, CH$_2$). 1.69 (m, 1H, CH), 1.46 (m, 4H, CH$_2$), 0.94 (t, 6H, CH$_3$).

LC-MS: m/z 446 M+H$^+$.

Step 2

1-[2-Bromo-5-(2-ethyl-butoxy)-benzyl]-1H-indazole-5-carboxylic acid, 16

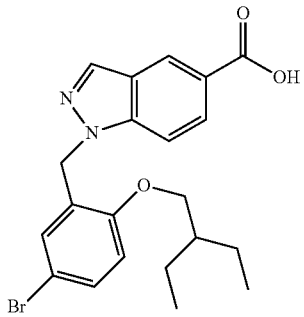 [SMILES: CCC(CC)COc1ccc(Br)cc1Cn1ncc2cc(C(=O)O)ccc21]

The title compound was prepared following the method in Example 1, Step 3.

$^1$H-NMR (CDCl$_3$, 300 MHz) δ 8.65 (s, 1H, ArH), 8.22 (s, 1H, ArH), 8.11 (dd, 1H, ArH), 7.45 (d, 1H, ArH), 7.36 (dd,

1H, ArH), 6.99 (d, 1H, ArH), 6.80 (d, 1H, ArH), 5.62 (s, 2H, ArCH$_2$), 3.92 (s, 3H, CH$_3$), 3.90 (d, 2H, CH$_2$). 1.69 (m, 1H, CH), 1.46 (m, 4H, CH$_2$), 0.94 (t, 6H, CH$_3$).

LC-MS: m/z 446 M+H$^+$.

EXAMPLE 6

1-[2-Chloro-5-(2-Ethyl-Butoxy)-Benzyl]-1H-Indazole-6-Carboxylic Acid, 21

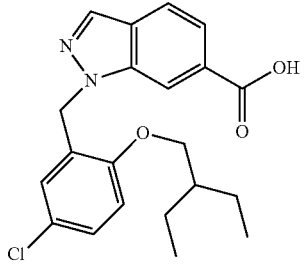 [SMILES: CCC(CC)COc1ccc(Cl)cc1Cn1ncc2ccc(C(=O)O)cc21]

Step 1

1H-Indazole-6-carboxylic acid methyl ester 17

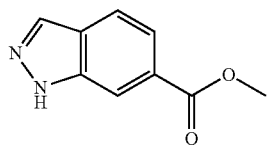

The title compound was prepared following the method in Example 2, Step 1.

$^1$H-NMR (CDCl$_3$, δ 10.37 (broad s, 1H, —NH), 8.29 (s, 1H, ArH), 8.17 (s, 1H, ArH), 8.11 (dd, 1H, ArH), 7.85 (dd, 2H, ArH), 3.99 (s, 3H, CH$_3$).

LC-MS: m/z 177 M+H$^+$.

Step 2

1-(2-Chloro-5-methoxy-benzyl)-1H-indazole-6-carboxylic acid methyl ester, 18

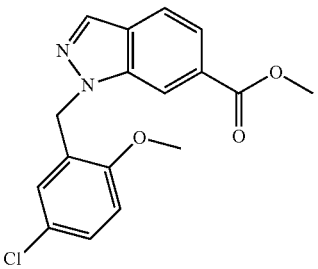 [SMILES: COC(=O)c1ccc2cnn(Cc3cc(Cl)ccc3OC)c2c1]

The title compound was prepared following the method in Example 3, Step 1.

$^1$H-NMR (CDCl$_3$, 300 MHz) δ 8.27 (s, 1H, ArH), 8.11 (s, 1H, ArH), 7.80 (m, 2H, ArH), 7.20 (dd, 1H, ArH), 6.89 (dd, 1H, ArH), 6.82 (d, 1H, ArH), 5.63 (s, 2H, ArCH$_2$), 3.96 (s, 3H, CH$_3$), 3.89 (s, 3H, CH$_3$).

LC-MS: m/z 331 M+H$^+$.

Step 3

1-(2-Chloro-5-hydroxy-benzyl)-1H-indazole-6-carboxylic methyl ester, 19

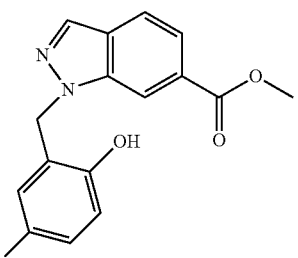

The title compound was prepared following the method in Example 3, Step 2.

$^1$H-NMR (CDCl$_3$, 300 MHz) δ 8.33 (s, 1H, ArH), 8.13 (s, 1H, ArH), 7.84 (m, 2H, ArH), 7.29 (d, 1H, ArH), 7.19 (dd, 1H, ArH), 6.94 (d, 1H, ArH), 5.52 (s, 2H, ArCH$_2$), 4.03 (s, 3H, CH$_3$).

LC-MS: m/z 331 M+H$^+$.

Step 4

1-[2-Chloro-5-(2-ethyl-butoxy)-benzyl]-1H-indazole-6-carboxylic acid methyl ester 20

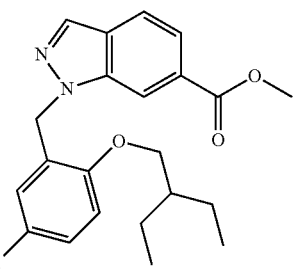

The title compound was prepared following the method in Example 3, Step 3.

$^1$H-NMR (CDCl$_3$, 300 MHz) δ 8.18 (s, 1H, ArH), 8.13 (s, 1H, ArH), 7.83 (m, 2H, ArH), 7.20 (dd, 1H, ArH), 6.84 (d, 1H, ArH), 6.72 (d, 1H, ArH), 5.65 (s, 2H, ArCH$_2$), 3.97 (s, 3H, CH$_3$), 3.92 (d, 2H, CH$_2$). 1.73 (m, 1H, CH), 1.48 (m, 4H, CH$_2$), 0.95 (t, 6H, CH$_3$).

LC-MS: m/z 401 M+H$^+$.

Step 5

1-[2-Chloro-5-(2-ethyl-butoxy)-benzyl]-1H-indazole-6-carboxylic acid, 21

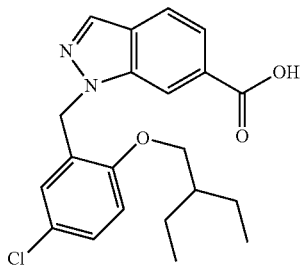 [SMILES: CCC(CC)COc1ccc(Cl)cc1Cn1ncc2ccc(C(=O)O)cc21]

The title compound was prepared following the method in Example 1, Step 3.

$^1$H-NMR (CDCl$_3$, 300 MHz) δ 8.29 (s, 1H, ArH), 8.16 (s, 1H, ArH), 7.88 (m, 2H, ArH), 7.21 (dd, 1H, ArH), 6.85 (d, 1H, ArH), 6.82 (d, 1H, ArH), 5.68 (s, 2H, ArCH$_2$), 3.93 (d, 2H, CH$_2$). 1.76 (m, 1H, CH), 1.48 (m, 4H, CH$_2$), 0.95 (t, 6H, CH$_3$).

LC-MS: m/z 387 M+H$^+$.

EXAMPLE 7

1-(5-Bromo-2-Isobutoxy-Benzyl)-1H-Indazole-4-Carboxylic Acid, 25

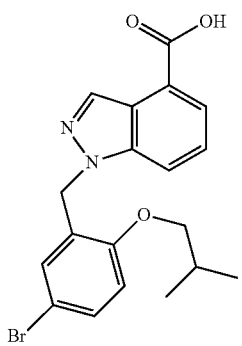 [SMILES: CC(C)COc1ccc(Br)cc1Cn1ncc2c(C(=O)O)cccc21]

Step 1

1-(5-Bromo-2-methoxy-benzyl)-1H-indazole-4-carboxylic acid methyl ester, 22

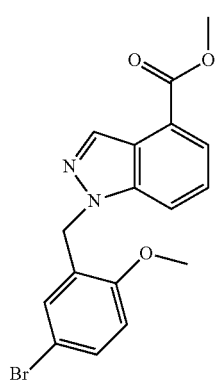 [SMILES: COC(=O)c1cccc2c1cnn2Cc1cc(Br)ccc1OC]

The title compound was prepared following the method in Example 3, Step 1.

$^1$H-NMR (CDCl$_3$, 300 MHz) δ 8.56 (s, 1H, ArH), 7.94 (d, 1H, ArH), 7.65 (d, 1H, ArH), 7.44 (dd, 1H, ArH), 6.98 (d, 1H, ArH), 6.76 (m, 2H, ArH), 5.61 (s, 2H, ArCH$_2$), 4.04 (s, 3H, CH$_3$), 3.85 (s, 3H, CH$_3$).

LC-MS: m/z 376 M+H$^+$.

Step 2

1-(5-Bromo-2-hydroxy-benzyl)-1H-indazole-4-carboxylic acid methyl ester, 23

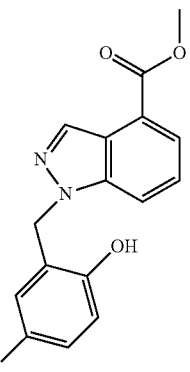

The title compound was prepared following the method in Example 3, Step 2.

$^1$H-NMR (CDCl$_3$, 300 MHz) δ 9.48 (s, 1H, ArOH), 8.59 (s, 1H, ArH), 7.98 (d, 1H, ArH), 7.78 (d, 1H, ArH), 7.56 (dd, 1H, ArH), 7.39 (d, 1H, ArH), 7.33 (dd, 1H, ArH), 6.89 (d, 1H, ArH), 5.49 (s, 2H, ArCH$_2$), 4.03 (s, 3H, CH$_3$).

LC-MS: m/z 362 M+H$^+$.

Step 3

1-(5-Bromo-2-isobutoxy-benzyl)-1H-indazole-4-carboxylic acid methyl ester, 24

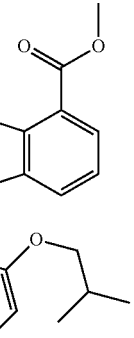

The title compound was prepared following the method in Example 3, Step 3.

$^1$H-NMR (CDCl$_3$, 300 MHz) δ 8.58 (s, 1H, ArH), 7.96 (d, 1H, ArH), 7.63 (d, 1H, ArH), 7.43 (dd, 1H, ArH), 7.33 (dd, 1H, ArH), 6.91 (d, 1H, ArH), 6.76 (d, 1H, ArH), 5.65 (s, 2H, ArCH$_2$), 4.05 (s, 3H, CH$_3$), 3.76 (d, 2H, CH$_2$). 2.12 (m, 1H, CH), 1.05 (d, 6H, CH$_3$).

LC-MS: m/z 418 M+H$^+$.

Step 4

1-(5-Bromo-2-isobutoxy-benzyl)-1H-indazole-4-carboxylic acid, 25

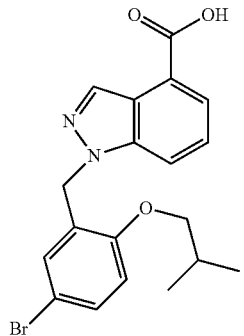 [SMILES: CC(C)COc1ccc(Br)cc1Cn1ncc2c(C(=O)O)cccc21]

The title compound was prepared following the method in Example 1, Step 3.

$^1$H-NMR (CDCl$_3$, 300 MHz) δ 8.67 (s, 1H, ArH), 8.07 (d, 1H, ArH), 7.71 (d, 1H, ArH), 7.48 (dd, 1H, ArH), 7.34 (dd, 1H, ArH), 6.97 (d, 1H, ArH), 6.77 (d, 1H, ArH), 5.68 (s, 2H, ArCH$_2$), 3.78 (d, 2H, CH$_2$). 2.12 (m, 1H, CH), 1.05 (d, 6H, CH$_3$).

LC-MS: m/z 404 M+H$^+$.

EXAMPLE 8

1-(2-Benzyloxy-5-Chloro-Benzyl)-1H-Indazole-5-Carboxylic Acid, 27

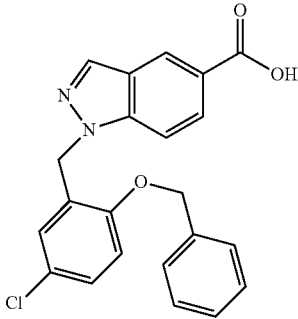 [SMILES: O=C(O)c1ccc2c(cnn2Cc2cc(Cl)ccc2OCc2ccccc2)c1]

Step 1

1-(2-Benzyloxy-5-chloro-benzyl)-1H-indazole-5-carboxylic acid methyl ester, 26

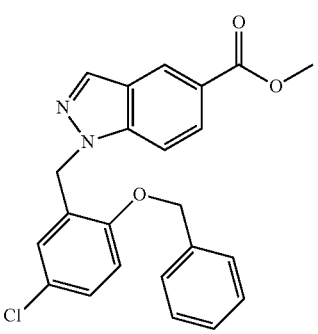 [SMILES: COC(=O)c1ccc2c(cnn2Cc2cc(Cl)ccc2OCc2ccccc2)c1]

To a solution of 1-(5-Chloro-2-hydroxy-benzyl)-1H-indazole-5-carboxylic acid methyl ester, 8, 0.04 g (0.13 mmol) in acetonitrile (10 ml), benzyl bromide (0.026 g, 0.15 mmol) and K$_2$CO$_3$ (0.026 g, 0.19 mmol) was added. The mixture was stirred under reflux for 2 hours, then the solids were filtered off and the solvents were removed in vacuo. The crude product was purified on silica to yield 0.05 g of 1-(2-benzyloxy-5-chloro-benzyl)-1H-indazole-5-carboxylic acid methyl ester, 28 as a white solid.

H-NMR (CDCl$_3$, 300 MHz) δ 8.52 (s, 1H, ArH), 8.16 (s, 1H, ArH), 7.92 (dd, 1H, ArH), 7.44-7.25 (m, 6H, ArH), 7.21 (dd, 1H, ArH), 6.96 (d, 1H, ArH), 6.89 (d, 1H, ArH), 5.61 (s, 2H, ArCH$_2$), 5.09 (s, 2H, ArCH$_2$), 3.97 (s, 3H, CH$_3$).

LC-MS: m/z 407 M+H$^+$.

Step 2

1-(2-Benzyloxy-5-chloro-benzyl)-1H-indazole-5-carboxylic acid, 27

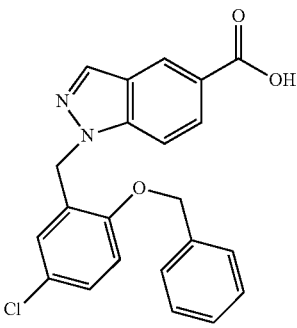 [SMILES: O=C(O)c1ccc2c(cnn2Cc2cc(Cl)ccc2OCc2ccccc2)c1]

The title compound was prepared following the method in Example 1, Step 3.

H-NMR (CDCl$_3$, 300 MHz) δ 8.62 (s, 1H, ArH), 8.20 (s, 1H, ArH), 7.96 (dd, 1H, ArH), 7.45-7.30 (m, 6H, ArH), 7.22 (dd, 1H, ArH), 7.01 (d, 1H, ArH), 6.91 (d, 1H, ArH), 5.62 (s, 2H, ArCH$_2$), 5.08 (s, 2H, ArCH$_2$), 3.97 (s, 3H, CH$_3$).

LC-MS: m/z 407 M+H$^+$.

EXAMPLE 9

1-[5-Chloro-2-(4-Chloro-Benzyloxy)-Benzyl]-1H-Indazole-5-Carboxylic Acid, 29

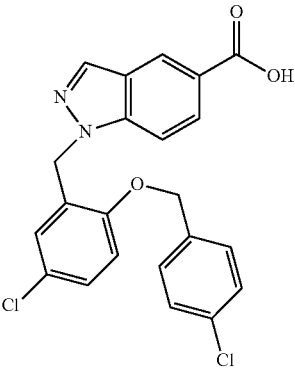 [SMILES: O=C(O)c1ccc2c(cnn2Cc2cc(Cl)ccc2OCc2ccc(Cl)cc2)c1]

Step 1

1-[5-Chloro-2-(4-chloro-benzyloxy)-benzyl]-1H-indazole-5-carboxylic acid methyl ester, 28

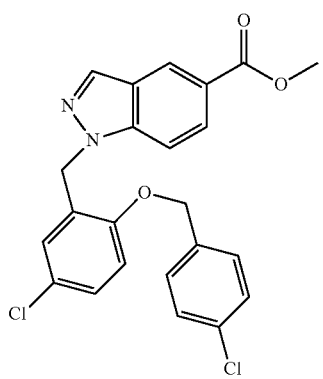 [SMILES: COC(=O)c1ccc2c(cnn2Cc2cc(Cl)ccc2OCc2ccc(Cl)cc2)c1]

The title compound was prepared following the method in Example 8, Step 1.

H-NMR (CDCl₃, 300 MHz) δ 8.52 (s, 1H, ArH), 8.15 (s, 1H, ArH), 7.93 (dd, 1H, ArH), 7.38-7.17 (m, 6H, ArH), 6.98 (d, 1H, ArH), 6.85 (d, 1H, ArH), 5.58 (s, 2H, ArCH₂), 5.01 (s, 2H, ArCH₂), 3.97 (s, 3H, CH₃).

LC-MS: m/z 442 M+H⁺.

Step 2

1-[5-Chloro-2-(4-chloro-benzyloxy)-benzyl]-1H-indazole-5-carboxylic acid, 29

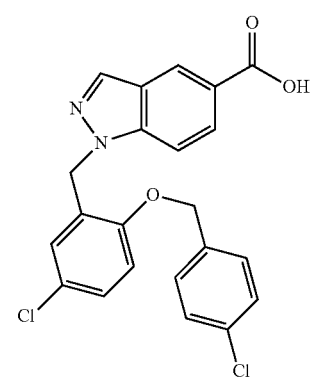 [SMILES: O=C(O)c1ccc2c(cnn2Cc2cc(Cl)ccc2OCc2ccc(Cl)cc2)c1]

The title compound was prepared following the method in Example 1, Step 3.

H-NMR (CDCl₃, 300 MHz) δ 8.63 (s, 1H, ArH), 8.20 (s, 1H, ArH), 8.00 (dd, 1H, ArH), 7.40-7.31 (m, 3H, ArH), 7.30-7.18 (m, 3H, ArH), 7.01 (d, 1H, ArH), 6.87 (d, 1H, ArH), 5.61 (s, 2H, ArCH₂), 5.04 (s, 2H, ArCH₂).

LC-MS: m/z 428 M+H⁺.

EXAMPLE 10

1-(5-Chloro-2-Cyclopentylmethoxy-Benzyl)-1H-Indazole-5-Carboxylic Acid, 31

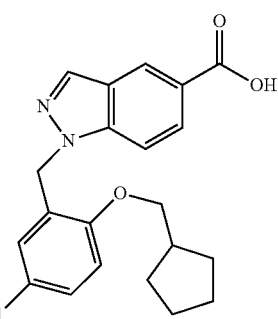

Step 1

1-(5-Chloro-2-cyclopentylmethoxy-benzyl)-1H-indazole-5-carboxylic acid methyl ester, 30

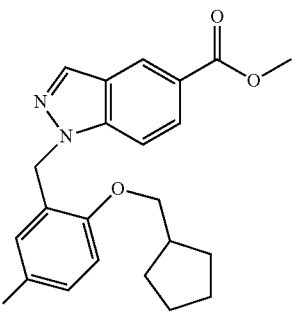

The title compound was prepared following the method in Example 3, Step 3.

H-NMR (CDCl₃, 300 MHz) δ 8.55 (s, 1H, ArH), 8.17 (s, 1H, ArH), 8.06 (dd, 1H, ArH), 7.45 (dd, 1H, ArH), 7.19 (dd, 1H, ArH), 6.86 (d, 1H, ArH), 6.81 (d, 1H, ArH), 5.30 (s, 2H, ArCH₂), 3.97 (s, 3H, CH₃), 3.87 (d, 2H, CH₂), 2.37 (m, 1H, CH), 1.92-0.81 (m, 8H, CH₂).

LC-MS: m/z 399 M+H⁺.

Step 2

1-(5-Chloro-2-cyclopentylmethoxy-benzyl)-1H-indazole-5-carboxylic acid, 31

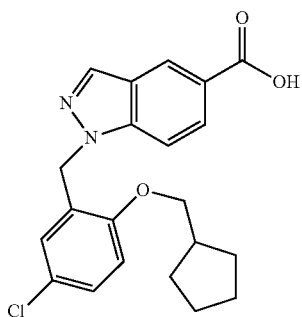 [SMILES: O=C(O)c1ccc2c(cnn2Cc2cc(Cl)ccc2OCC2CCCC2)c1]

The title compound was prepared following the method in Example 1, Step 3.

H-NMR (CDCl$_3$, 300 MHz) δ 8.66 (s, 1H, ArH), 8.22 (s, 1H, ArH), 8.12 (dd, 1H, ArH), 7.50 (d, 1H, ArH), 7.21 (d, 1H, ArH), 6.91 (d, 1H, ArH), 6.82 (d, 1H, ArH), 5.62 (s, 2H, ArCH$_2$), 3.88 (d, 2H, CH$_2$), 2.37 (m, 1H, CH), 1.83 (m, 2H, CH$_2$), 1.64 (m, 4H, CH$_2$), 1.45-1.21 (m, 2H, CH$_2$).

LC-MS: m/z 385 M+H$^+$.

EXAMPLE 11

1-(5-Chloro-2-Cyclopropylmethoxy-Benzyl)-1H-Indazole-5-Carboxylic Acid, 33

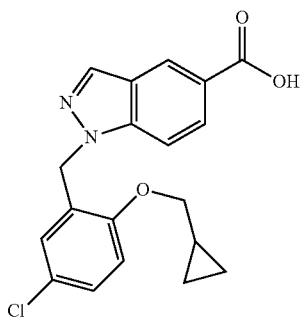

Step 1

1-(5-Chloro-2-cyclopropylmethoxy-benzyl)-1H-indazole-5-carboxylic acid methyl ester, 32

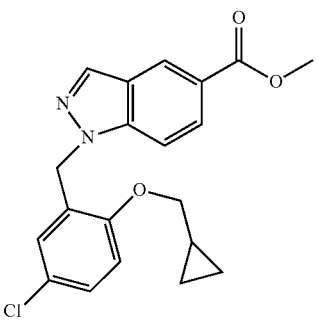

The title compound was prepared following the method in Example 3, Step 3 and was used without purification in subsequent step.

LC-MS: m/z 371 M+H$^+$.

Step 2

1-(5-Chloro-2-cyclopropylmethoxy-benzyl)-1H-indazole-5-carboxylic acid, 33

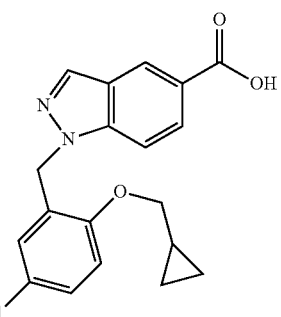

The title compound was prepared following the method in Example 1, Step 3.

H-NMR (CDCl$_3$, 300 MHz) δ 8.63 (s, 1H, ArH), 8.20 (s, 1H, ArH), 8.11 (dd, 1H, ArH), 7.63 (d, 1H, ArH), 7.20 (d, 1H, ArH), 7.06 (d, 1H, ArH), 6.77 (d, 1H, ArH), 5.64 (s, 2H, ArCH$_2$), 3.82 (d, 2H, CH$_2$), 1.24 (m, 1H, CH), 0.65 (m, 2H, CH$_2$), 0.33 (m, 2H, CH$_2$).

LC-MS: m/z 357 M+H$^+$.

EXAMPLE 12

1-(2-Benzyloxy-5-Bromo-Benzyl)-1H-Indazole-5-Carboxylic Acid, 35

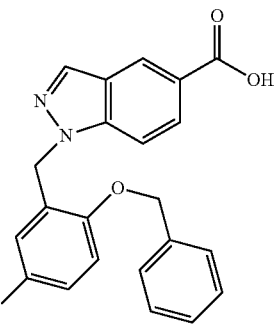

Step 1

1-(2-Benzyloxy-5-bromo-benzyl)-1H-indazole-5-carboxylic acid methyl ester, 34

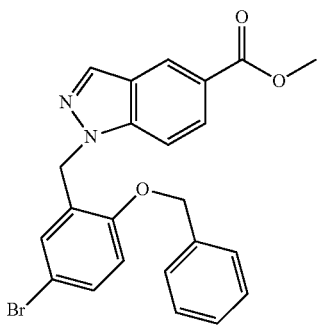

The title compound was prepared following the method in Example 8, Step 1.

H-NMR (CDCl$_3$, 300 MHz) δ 8.52 (s, 1H, ArH), 8.16 (s, 1H, ArH), 7.91 (dd, 1H, ArH), 7.44-7.25 (m, 7H, ArH), 7.12 (dd, 1H, ArH), 6.84 (d, 1H, ArH), 5.60 (s, 2H, ArCH$_2$), 5.08 (s, 2H, ArCH$_2$), 3.97 (s, 3H, CH$_3$).

LC-MS: m/z 452 M+H$^+$.

Step 2

1-(2-Benzyloxy-5-bromo-benzyl)-1H-indazole-5-carboxylic acid, 35

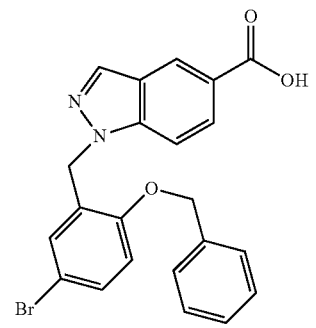

The title compound was prepared following the method in Example 1, Step 3.

H-NMR (CDCl$_3$, 300 MHz) δ 8.60 (s, 1H, ArH), 8.19 (s, 1H, ArH), 7.95 (dd, 1H, ArH), 7.43-7.29 (m, 7H, ArH), 7.17 (dd, 1H, ArH), 6.85 (d, 1H, ArH), 5.61 (s, 2H, ArCH$_2$), 5.08 (s, 2H, ArCH$_2$).

LC-MS: m/z 438 M+H$^+$.

EXAMPLE 13

1-[5-Bromo-2-(4-Chloro-Benzyloxy)-Benzyl]-1H-Indazole-5-Carboxylic Acid, 37

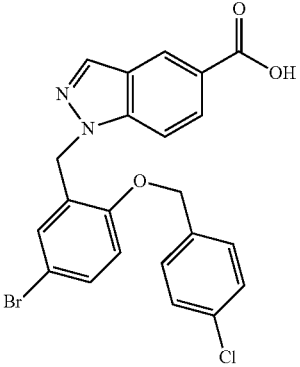

Step 1

1-[5-Bromo-2-(4-chloro-benzyloxy)-benzyl]-1H-indazole-5-carboxylic acid methyl ester, 36

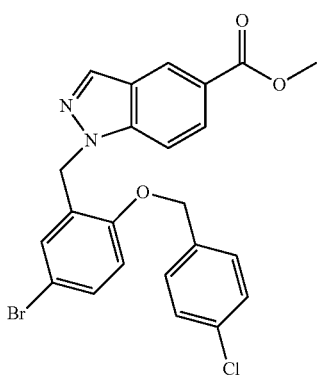

The title compound was prepared following the method in Example 8, Step 1.

H-NMR (CDCl$_3$, 300 MHz) 8.52 (s, 1H, ArH), 8.15 (s, 1H, ArH), 7.93 (dd, 1H, ArH), 7.42-7.17 (m, 6H, ArH), 7.14 (d, 1H, ArH), 6.80 (d, 1H, ArH), 5.58 (s, 2H, ArCH$_2$), 5.02 (s, 2H, ArCH$_2$), 3.97 (s, 3H, CH$_3$).

LC-MS: m/z 486 M+H$^+$.

Step 2

1-[5-Chloro-2-(4-chloro-benzyloxy)-benzyl]-1H-indazole-5-carboxylic acid, 37

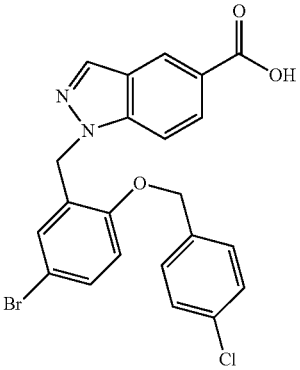

The title compound was prepared following the method in Example 1, Step 3.

H-NMR (CDCl₃, 300 MHz) δ 8.63 (s, 1H, ArH), 8.20 (s, 1H, ArH), 8.00 (dd, 1H, ArH), 7.43-7.17 (m, 6H, ArH), 7.17 (d, 1H, ArH), 6.82 (d, 1H, ArH), 5.60 (s, 2H, ArCH₂), 5.03 (s, 2H, ArCH₂).

LC-MS: m/z 428 M+H⁺.

EXAMPLE 14

1-(5-Bromo-2-Cyclopentylmethoxy-Benzyl)-1H-Indazole-5-Carboxylic Acid, 39

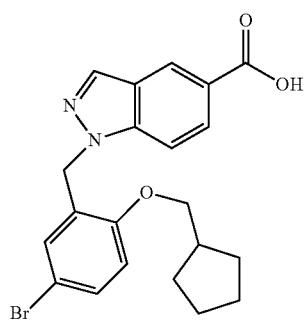

Step 1

1-(5-Bromo-2-cyclopentylmethoxy-benzyl)-1H-indazole-5-carboxylic acid methyl ester, 38

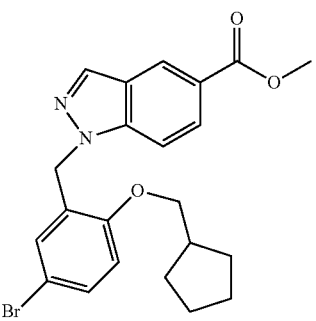 [SMILES: COC(=O)c1ccc2c(cnn2Cc2cc(Cl)ccc2OCC2CCCC2)c1]

The title compound was prepared following the method in Example 3, Step 3.

H-NMR (CDCl₃, 300 MHz) δ 8.55 (s, 1H, ArH), 8.17 (s, 1H, ArH), 8.05 (dd, 1H, ArH), 7.46 (dd, 1H, ArH), 7.34 (dd, 1H, ArH), 7.02 (d, 1H, ArH), 6.77 (d, 1H, ArH), 5.59 (s, 2H, ArCH₂), 3.97 (s, 3H, CH₃), 3.87 (d, 2H, CH₂), 2.36 (m, 1H, CH), 1.91-0.81 (m, 8H, CH₂).

LC-MS: m/z 444 M+H⁺.

Step 2

1-(5-Chloro-2-cyclopentylmethoxy-benzyl)-1H-indazole-5-carboxylic acid, 39

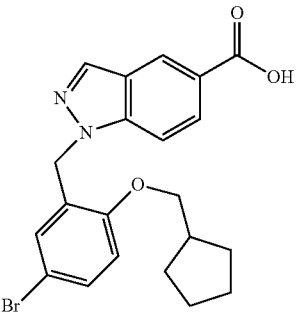 [SMILES: O=C(O)c1ccc2c(cnn2Cc2cc(Cl)ccc2OCC2CCCC2)c1]

The title compound was prepared following the method in Example 1, Step 3.

H-NMR (CDCl₃, 300 MHz) δ 8.65 (s, 1H, ArH), 8.21 (s, 1H, ArH), 8.11 (dd, 1H, ArH), 7.50 (d, 1H, ArH), 7.35 (d, 1H, ArH), 7.06 (d, 1H, ArH), 6.78 (d, 1H, ArH), 5.61 (s, 2H, ArCH₂), 3.87 (d, 2H, CH₂), 2.36 (m, 1H, CH), 1.83 (m, 2H, CH₂), 1.91-1.17 (m, 8H, CH₂).

LC-MS: m/z 430 M+H⁺.

EXAMPLE 15

1-(5-Bromo-2-Cyclopropylmethoxy-Benzyl)-1H-Indazole-5-Carboxylic Acid, 41

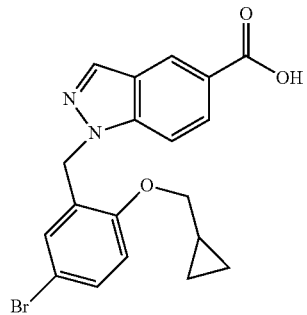 [SMILES: O=C(O)c1ccc2c(cnn2Cc2cc(Cl)ccc2OCC2CC2)c1]

Step 1

1-(5-Bromo-2-cyclopropylmethoxy-benzyl)-1H-indazole-5-carboxylic acid methyl ester, 40

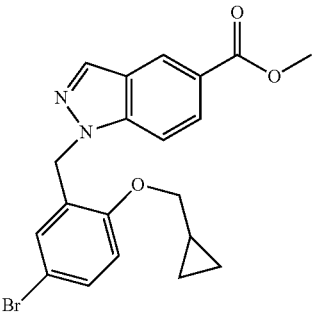 [SMILES: COC(=O)c1ccc2c(cnn2Cc2cc(Cl)ccc2OCC2CC2)c1]

The title compound was prepared following the method in Example 3, Step 3.

H-NMR (CDCl₃, 300 MHz) δ 8.53 (s, 1H, ArH), 8.16 (s, 1H, ArH), 8.05 (dd, 1H, ArH), 7.59 (d, 1H, ArH), 7.34 (dd,

1H, ArH), 7.18 (d, 1H, ArH), 6.71 (d, 1H, ArH), 5.61 (s, 2H, ArCH$_2$), 3.97 (s, 3H, CH$_3$), 3.81 (d, 2H, CH$_2$), 1.23 (m, 1H, CH), 0.92 (m, 2H, CH$_2$), 0.63 (m, 2H, CH$_2$).
LC-MS: m/z 416 M+H$^+$.

Step 2

1-(5-Bromo-2-cyclopropylmethoxy-benzyl)-1H-indazole-5-carboxylic acid, 41

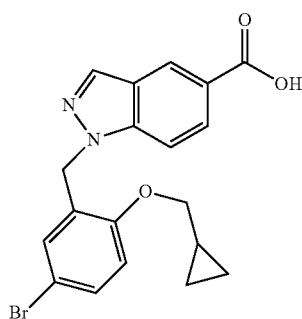 [SMILES: O=C(O)c1ccc2c(cnn2Cc2cc(Cl)ccc2OCC2CC2)c1]

The title compound was prepared following the method in Example 1, Step 3.
H-NMR (CDCl$_3$, 300 MHz) δ 8.61 (s, 1H, ArH), 8.19 (s, 1H, ArH), 8.09 (dd, 1H, ArH), 7.63 (d, 1H, ArH), 7.35 (dd, 1H, ArH), 7.21 (d, 1H, ArH), 6.72 (d, 1H, ArH), 5.63 (s, 2H, ArCH$_2$), 3.81 (d, 2H, CH$_2$), 1.26 (m, 1H, CH), 0.64 (m, 2H, CH$_2$), 0.32 (m, 2H, CH$_2$).
LC-MS: m/z 402 M+H$^+$.

EXAMPLE 16

2-(5-Chloro-2-Isobutoxy-Benzyl)-2H-Indazole-5-Carboxylic Acid, 45

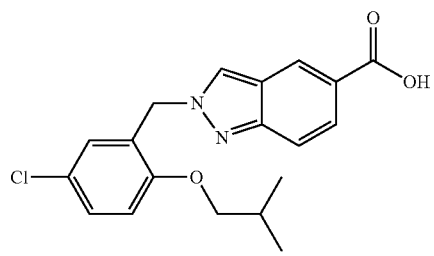 [SMILES: CC(C)COc1ccc(Cl)cc1Cn1cc2cc(C(=O)O)ccc2n1]

Step 1

2-(5-Chloro-2-methoxy-benzyl)-2H-indazole-5-carboxylic acid methyl ester 42

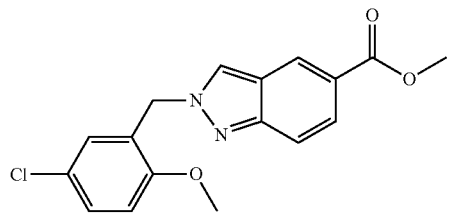 [SMILES: COC(=O)c1ccc2nn(Cc3cc(Cl)ccc3OC)cc2c1]

The title compound was prepared following the method in Example 3, Step 1.
$^1$H-NMR (CDCl$_3$, 300 MHz) δ 8.51 (s, 1H, ArH), 8.11 (s, 1H, ArH), 7.91 (dd, 1H, ArH), 7.73 (d, 1H, ArH), 7.30 (dd, 1H, ArH), 7.16 (d, 1H, ArH), 6.87 (d, 1H, ArH), 5.60 (s, 2H, ArCH$_2$), 3.95 (s, 3H, CH$_3$), 3.88 (s, 3H, CH$_3$).
LC-MS: m/z 331 M+H$^+$.

Step 2

2-(5-Chloro-2-hydroxy-benzyl)-2H-indazole-5-carboxylic acid methyl ester 43

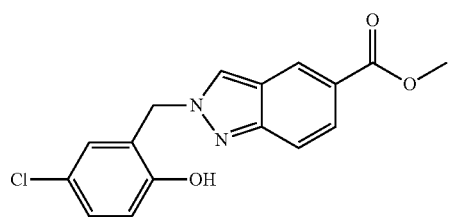 [SMILES: COC(=O)c1ccc2nn(Cc3cc(Cl)ccc3O)cc2c1]

The title compound was prepared following the method in Example 3, Step 2.
$^1$H-NMR (CDCl$_3$, 300 MHz) δ 10.53 (s, 1H, ArOH), 8.52 (s, 1H, ArH), 8.21 (s, 1H, ArH), 7.99 (dd, 1H, ArH), 7.70 (d, 1H, ArH), 7.33-7.21 (m, 2H, ArH), 6.99 (d, 1H, ArH), 5.50 (s, 2H, ArCH$_2$), 3.96 (s, 3H, CH$_3$.
LC-MS: m/z 317 M+H$^+$.

Step 3

2-(5-Chloro-2-isobutoxy-benzyl)-2H-indazole-5-carboxylic acid methyl ester, 44

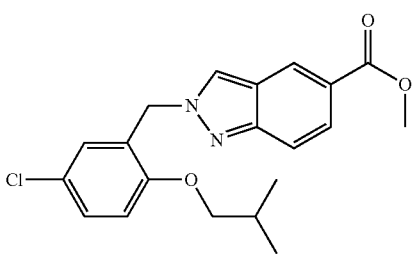 [SMILES: COC(=O)c1ccc2nn(Cc3cc(Cl)ccc3OCC(C)C)cc2c1]

The title compound was prepared following the method in Example 3, Step 3.
$^1$H-NMR (CDCl$_3$, 300 MHz) δ 8.49 (s, 1H, ArH), 8.09 (s, 1H, ArH), 7.91 (dd, 1H, ArH), 7.73 (d, 1H, ArH), 7.27 (dd, 1H, ArH), 7.14 (d, 1H, ArH), 6.83 (d, 1H, ArH), 5.62 (s, 2H, ArCH$_2$), 3.94 (s, 3H, CH$_3$), 3.76 (d, 2H, CH$_2$). 2.10 (m, 1H, CH), 1.00 (d, 6H, CH$_3$).
LC-MS: m/z 373 M+H$^+$.

Step 4

2-(5-Chloro-2-isobutoxy-benzyl)-2H-indazole-5-carboxylic acid, 45

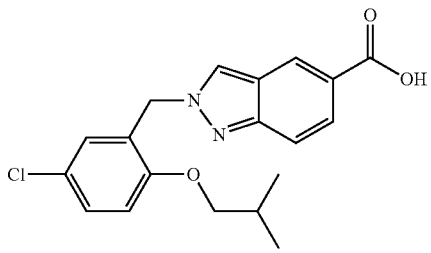 [SMILES: CC(C)COc1ccc(Cl)cc1Cn1cc2cc(C(=O)O)ccc2n1]

The title compound was prepared following the method in Example 1, Step 3.

$^1$H-NMR (CDCl$_3$, 300 MHz) δ 8.57 (s, 1H, ArH), 8.12 (s, 1H, ArH), 7.95 (dd, 1H, ArH), 7.76 (d, 1H, ArH), 7.28 (dd, 1H, ArH), 7.16 (d, 1H, ArH), 6.85 (d, 1H, ArH), 5.63 (s, 2H, ArCH$_2$), 3.77 (d, 2H, CH$_2$). 2.11 (m, 1H, CH), 1.01 (d, 6H, CH$_3$).

LC-MS: m/z 359 M+H$^+$.

EXAMPLE 17

2-(5-Bromo-2-Isobutoxy-Benzyl)-2H-Indazole-5-Carboxylic Acid, 49

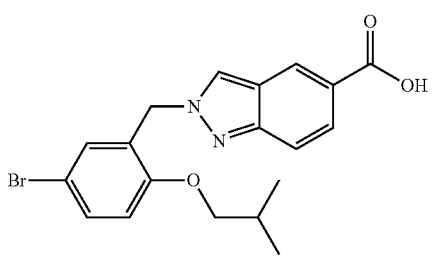

Step 1

2-(5-Bromo-2-methoxy-benzyl)-2H-indazole-5-carboxylic acid methyl ester 46

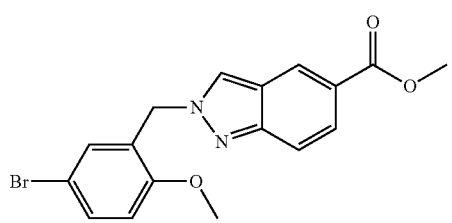

The title compound was prepared following the method in Example 3, Step 1.

$^1$H-NMR (CDCl$_3$, 300 MHz) δ 8.50 (s, 1H, ArH), 8.11 (s, 1H, ArH), 7.92 (dd, 1H, ArH), 7.73 (d, 1H, ArH), 7.45 (dd, 1H, ArH), 7.30 (d, 1H, ArH), 6.82 (d, 1H, ArH), 5.60 (s, 2H, ArCH$_2$), 3.95 (s, 3H, CH$_3$), 3.87 (s, 3H, CH$_3$).

LC-MS: m/z 376 M+H$^+$.

Step 2

2-(5-Bromo-2-hydroxy-benzyl)-2H-indazole-5-carboxylic acid methyl ester 47

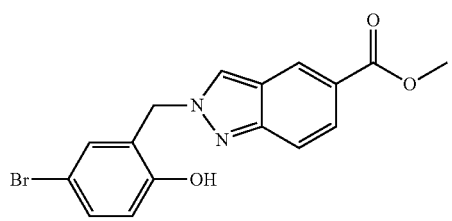

The title compound was prepared following the method in Example 3, Step 2.

$^1$H-NMR (CDCl$_3$, 300 MHz) 10.59 (broad s, 1H, ArOH), 8.52 (s, 1H, ArH), 8.21 (s, 1H, ArH), 7.99 (dd, 1H, ArH), 7.70 (d, 1H, ArH), 7.45-7.36 (m, 2H, ArH), 6.94 (d, 1H, ArH), 5.49 (s, 2H, ArCH$_2$), 3.96 (s, 3H, CH$_3$.

LC-MS: m/z 362 M+H$^+$.

Step 3

2-(5-Chloro-2-isobutoxy-benzyl)-2H-indazole-5-carboxylic acid methyl ester, 48

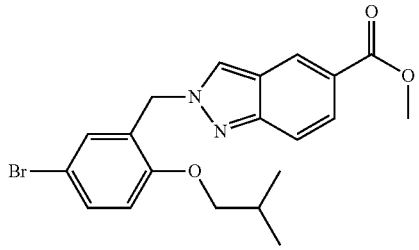 [SMILES: COC(=O)c1ccc2nn(Cc3cc(Br)ccc3OCC(C)C)cc2c1]

The title compound was prepared following the method in Example 3, Step 3.

$^1$H-NMR (CDCl$_3$, 300 MHz) δ 8.50 (s, 1H, ArH), 8.09 (s, 1H, ArH), 7.92 (dd, 1H, ArH), 7.73 (d, 1H, ArH), 7.43 (dd, 1H, ArH), 7.29 (d, 1H, ArH), 6.80 (d, 1H, ArH), 5.62 (s, 2H, ArCH$_2$), 3.95 (s, 3H, CH$_3$), 3.76 (d, 2H, CH$_2$). 2.10 (m, 1H, CH), 1.00 (d, 6H, CH$_3$).

LC-MS: m/z 417 M+H$^+$.

Step 4

2-(5-Bromo-2-isobutoxy-benzyl)-2H-indazole-5-carboxylic acid, 49

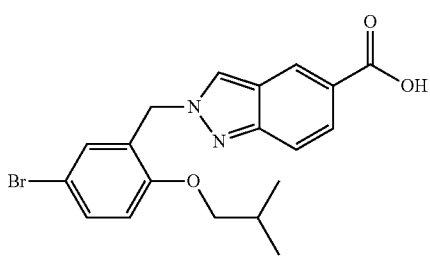

The title compound was prepared following the method in Example 1, Step 3.

$^1$H-NMR (CDCl$_3$, 300 MHz) δ 8.60 (s, 1H, ArH), 8.12 (s, 1H, ArH), 7.96 (dd, 1H, ArH), 7.77 (d, 1H, ArH), 7.43 (dd, 1H, ArH), 7.32 (d, 1H, ArH), 6.80 (d, 1H, ArH), 5.64 (s, 2H, ArCH$_2$), 3.77 (d, 2H, CH$_2$). 2.11 (m, 1H, CH), 1.01 (d, 6H, CH$_3$).

EXAMPLE 18

1-(2-(Trifluoromethyl)-5-Isobutoxy-Benzyl)-1H-Indazole-5-Carboxylic Acid, 53

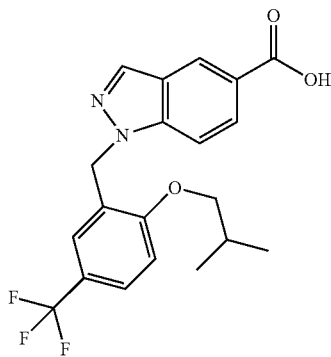 [SMILES: CC(C)COc1ccc(C(F)(F)F)cc1Cn1ncc2cc(C(=O)O)ccc21]

Step 1

1-(5-(Trifluoromethyl)-2-methoxy-benzyl)-1H-indazole-5-carboxylic acid methyl ester, 50

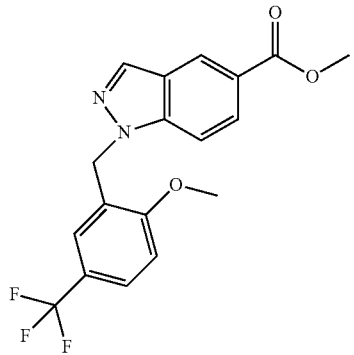 [SMILES: COC(=O)c1ccc2c(cnn2Cc2cc(C(F)(F)F)ccc2OC)c1]

The title compound was prepared following the method in Example 3, Step 1. But using (5-(trifluoromethyl)-2-methoxy-phenyl)-methanol, instead of (5-chloro-2-methoxy-phenyl)-methanol.

$^1$H-NMR (CDCl$_3$, 300 MHz) δ 8.54 (s, 1H, ArH), 8.16 (s, 1H, ArH), 8.07 (dd, 1H, ArH), 7.53 (d, 1H, ArH), 7.45 (dd, 1H, ArH), 7.23 (m, 1H, ArH), 6.94 (d, 1H, ArH), 5.62 (s, 2H, ArCH$_2$), 3.91 (s, 3H, CH$_3$), 3.90 (s, 3H, CH$_3$).

Step 2

1-(2-(trifluoromethyl)-5-hydroxy-benzyl)-1H-indazole-5-carboxylic acid methyl ester, 51

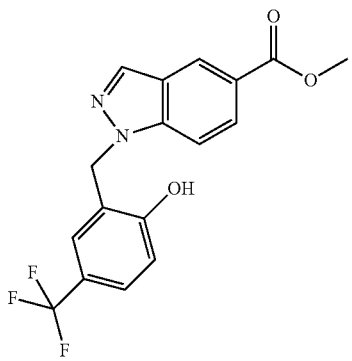 [SMILES: COC(=O)c1ccc2c(cnn2Cc2cc(C(F)(F)F)ccc2O)c1]

The title compound was prepared following the method in Example 3, Step 2

$^1$H-NMR (CDCl$_3$, 300 MHz) δ 8.54 (s, 1H, ArH), 8.16 (s, 1H, ArH), 8.07 (dd, 1H, ArH), 7.53 (d, 1H, ArH), 7.45 (dd, 1H, ArH), 7.23 (m, 1H, ArH), 6.94 (d, 1H, ArH), 5.54 (s, 2H, ArCH$_2$), 3.97 (s, 3H, CH$_3$).

LC-MS: m/z 351 M+H$^+$.

Step 3

1-(2-(trifluromethyl)-5-isobutoxy-benzyl)-1H-indazole-5-carboxylic acid methyl ester, 52

The title compound was prepared following the method in Example 3, Step 3.

$^1$H-NMR (CDCl$_3$, 300 MHz) δ 8.55 (s, 1H, ArH), 8.17 (s, 1H, ArH), 8.05 (dd, 1H, ArH), 7.52 (dd, 1H, ArH), 7.43 (d,

1H, ArH), 7.17 (m, 1H, ArH), 6.95 (d, 1H, ArH), 5.65 (s, 2H, ArCH$_2$), 3.96 (s, 3H, CH$_3$), 3.82 (d, 2H, —OCH$_2$CH(CH$_3$)$_2$), 2.11 (m, 1H, —OCH$_2$CH(CH$_3$)$_2$), 1.02 (d, 3H, —OCH$_2$CH(CH$_3$)$_2$), 0.87 (d, 3H, —OCH$_2$CH(CH$_3$)$_2$).

Step 4

1-(2-(trifluoromethyl)-5-isobutoxy-benzyl)-1H-indazole-5-carboxylic acid, 53

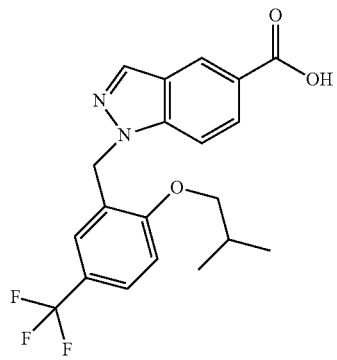 [SMILES: CC(C)COc1ccc(C(F)(F)F)cc1Cn1ncc2cc(C(=O)O)ccc21]

The title compound was prepared following the method in Example 1, Step 3.

$^1$H-NMR (CDCl$_3$, 300 MHz) δ 8.66 (s, 1H, ArH), 8.22 (s, 1H, ArH), 8.12 (dd, 1H, ArH), 7.53 (dd, 1H, ArH), 7.47 (d, 1H, ArH), 7.22 (m, 1H, ArH), 6.95 (d, 1H, ArH), 5.68 (s, 2H, ArCH$_2$), 3.83 (d, 2H, —OCH$_2$CH(CH$_3$)$_2$), 2.14 (m, 1H, —OCH$_2$CH(CH$_3$)$_2$), 1.02 (d, 6H, —OCH$_2$CH(CH$_3$)$_2$).

LC-MS: m/z 393 M+H$^+$.

EXAMPLE 19

1-(5-Bromo-2-Cyclopropyl-2-Methylmethoxy-Benzyl)-1H-Indazole-5-Carboxylic Acid, 55

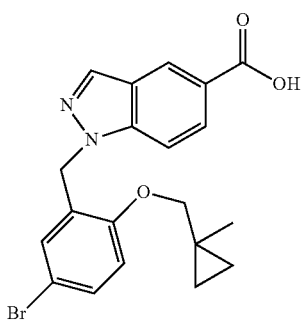 [SMILES: CC1(COc2ccc(Br)cc2Cn2ncc3cc(C(=O)O)ccc32)CC1]

Step 1

1-(5-Bromo-2-cyclopropyl-2-methylmethoxy-benzyl)-1H-indazole-5-carboxylic acid methyl ester, 54

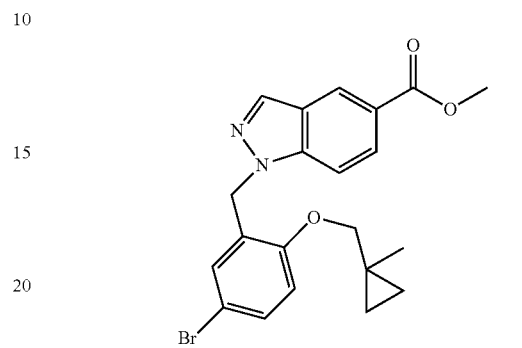

The title compound was prepared following the method in Example 3, Step 3.

H-NMR (CDCl$_3$, 300 MHz) δ 8.55 (s, 1H, ArH), 8.15 (s, 1H, ArH), 8.05 (dd, 1H, ArH), 7.55 (d, 1H, ArH), 7.34 (dd, 1H, ArH), 7.10 (d, 1H, ArH), 6.70 (d, 1H, ArH), 5.65 (s, 2H, ArCH$_2$), 3.97 (s, 3H, CH$_3$), 3.75 (s, 2H, CH$_2$), 1.20 (s, 3H, CH$_3$), 0.55 (m, 2H, CH$_2$), 0.45 (m, 2H, CH$_2$).

LC-MS: m/z 430 M+H$^+$.

Step 2

1-(5-Bromo-2-cyclopropyl-2-methylmethoxy-benzyl)-1H-indazole-5-carboxylic acid, 55

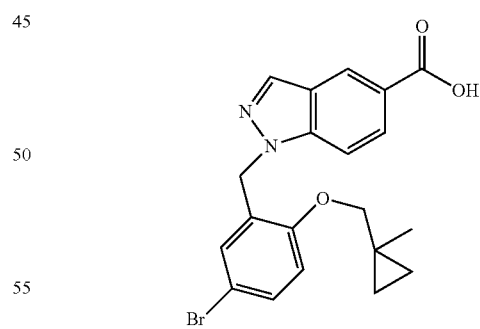

The title compound was prepared following the method in Example 1, Step 3.

H-NMR (CDCl$_3$, 300 MHz) δ 8.65 (s, 1H, ArH), 8.20 (s, 1H, ArH), 8.10 (dd, 1H, ArH), 7.60 (d, 1H, ArH), 7.34 (dd, 1H, ArH), 7.10 (d, 1H, ArH), 6.70 (d, 1H, ArH), 5.65 (s, 2H, ArCH$_2$), 3.75 (s, 2H, CH$_2$), 1.20 (s, 3H, CH$_3$), 0.55 (m, 2H, CH$_2$), 0.45 (m, 2H, CH$_2$).

LC-MS: m/z 416 M+H$^+$.

EXAMPLE 20

1-(2-Isobutoxy-5-Trifluoromethoxy-Benzyl)-1H-Indazole-5-Carboxylic Acid, 60

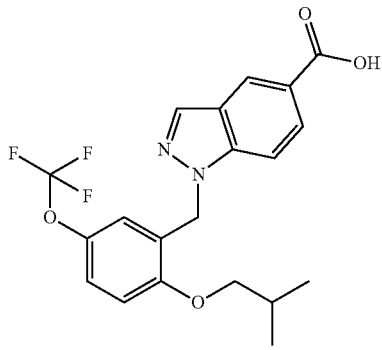 [SMILES: CC(C)COc1ccc(OC(F)(F)F)cc1Cn1ncc2cc(C(=O)O)ccc21]

Step 1

2-Isobutoxy-5-trifluoromethoxy-benzaldehyde, 56

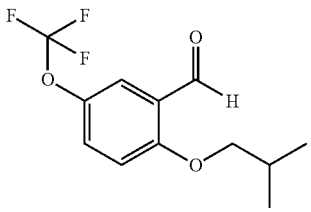 [SMILES: CC(C)COc1ccc(OC(F)(F)F)cc1C=O]

A solution of 2-Hydroxy-5-trifluoromethoxy-benzaldehyde (1.0 g, 4.9 mmole) in DMF (10 ml) was treated with potassium carbonate (1.5 g, 10.9 mmole) and tetrabutylammonium iodide (0.01 g) and 1-chloro-2-methylpropane (1.05 ml, 10 mmole). The mixture was stirred at 110° C. under a nitrogen atmosphere for 18 h. The mixture was then evaporated to dryness and the residue partitioned between ethyl acetate (50 ml) and water (50 ml). The organic extract was separated then washed with saturated brine then dried over sodium sulphate, filtered and evaporated to dryness. The residue was chromatographed on silica gel eluting with a gradient of 5-15% ethyl acetate/isohexane. This gave the title compound as a pale yellow oil (1.02 g, 80%).

H-NMR (CDCl$_3$, 300 MHz) δ10.49 (s, 1H, CHO), 7.71 (d, 1H, ArH), 7.38 (dd, 1H, ArH), 6.95 (d, 1H, ArH), 3.89 (d, 2H, CH$_2$), 2.15-2.28 (m, 1H, CH), 1.05 (d, 6H, 2×CH$_3$).

Step 2

(2-Isobutoxy-5-trifluoromethoxy-phenyl)-methanol, 57

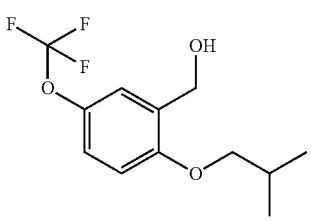 [SMILES: CC(C)COc1ccc(OC(F)(F)F)cc1CO]

A solution of 2-Isobutoxy-5-trifluoromethoxy-benzaldehyde (1.02 g, 3.9 mmole) in methanol (20 ml) was treated with sodium borohydride (0.22 g, 5.8 mmole) then stirred at ambient temperature under a nitrogen atmosphere for 2 h. The mixture was evaporated to dryness and the residue partitioned between water (50 ml) and dichloromethane (2×50 ml). The combined organic extracts were dried over sodium sulphate, filtered and evaporated to dryness. The residue was chromatographed on silica gel eluting with a gradient of 10-20% ethyl acetate/isohexane. This gave the title compound as a colorless oil (1.0 g, 97%).

H-NMR (CDCl$_3$, 300 MHz) δ7.22 s, 1H, ArH), 7.09 (dd, 1H, ArH), 6.41 (d, 1H, ArH), 4.71 (d, 2H, CH$_2$), 3.81 (d, 2H, CH$_2$), 2.23 (t, 1H, OH), 2.07-2.19 (m, 1H, CH), 1.07 (d, 6H, 2×CH$_3$).

Step 3

Methanesulfonic acid 2-isobutoxy-5-trifluoromethoxy-benzyl ester, 58

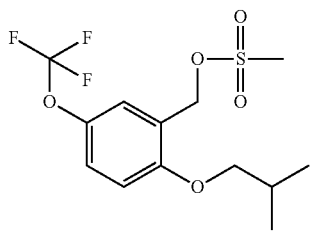 [SMILES: CC(C)COc1ccc(OC(F)(F)F)cc1COS(C)(=O)=O]

A solution of (2-Isobutoxy-5-trifluoromethoxy-phenyl)-methanol (1.0 g, 3.8 mmole) in dichloromethane (50 ml) was treated with diisopropylethylamine (0.73 ml, 4.2 mmole) and methanesulphonic anhydride (0.73 g, 4.2 mmole) then stirred at ambient temperature under a nitrogen atmosphere for 1.5 h. The mixture was then washed with water (50 ml) and saturated brine (50 ml). The organic layer was dried over sodium sulphate, filtered and evaporated to dryness to give the title compound as a colorless oil (1.2 g, 92%).

H-NMR (CDCl$_3$, 300 MHz) δ 7.27 (s, 1H, ArH), 7.19 (dd, 1H, ArH), 6.92 (d, 1H, ArH), 5.29 (s, 2H, CH$_2$), 3.79 (d, 2H, CH$_2$), 2.99 (s, 3H, CH$_3$), 2.07-2.19 (m, 1H, CH), 1.05 (d, 6H, 2×CH$_3$).

Step 4

1-(2-Isobutoxy-5-trifluoromethoxy-benzyl)-1H-indazole-5-carboxylic acid methyl ester, 59

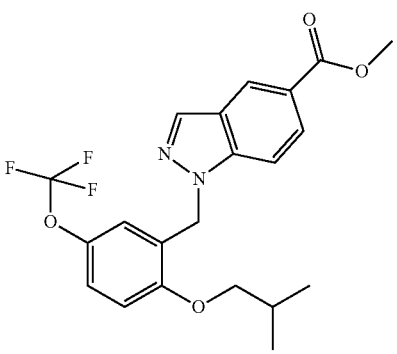 [SMILES: COC(=O)c1ccc2c(cnn2Cc2cc(OC(F)(F)F)ccc2OCC(C)C)c1]

A solution of 1H-Indazole-5-carboxylic acid methyl ester (0.154 g, 0.88 mmole) in DMF (5 ml) was treated with sodium hydride (60% dispersion in oil) (0.042 g, 1 mmole) then stirred at ambient temperature under a nitrogen atmosphere for 1 h. A solution of methanesulfonic acid 2-isobutoxy-5-trifluoromethoxy-benzyl ester (0.3 g, 0.88 mmole) in DMF (5 ml) was then added and the mixture stirred at ambient temperature for 18 h. The mixture was evaporated to dryness and the residue partitioned between water (20 ml) and dichloromethane (2×20 ml). The combined organics were dried over sodium sulphate, filtered and evaporated to dryness. The residue was chromatographed using silica gel eluting with a gradient of 5-20% ethyl acetate/isohexane to give in the early fractions the title compound (0.217 g, 59%) as a white solid. The corresponding 2-yl-indazole isomer eluted in the later column fractions.

H-NMR (CDCl$_3$, 300 MHz) δ8.55 (s, 1H, ArH), 8.15 (s, 1H, ArH), 8.01 (dd, 1H, ArH), 7.41 (d, 1H, ArH), 7.11 (dd, 1H, ArH), 6.88 (d, 1H, ArH), 6.71 (s, 1H, ArH), 5.61 (s, 2H, CH$_2$), 3.99 (s, 3H, CH$_3$), 3.78 (d, 2H, CH$_2$), 2.05-2.19 (m, 1H, CH), 1.04 (d, 6H, 2×CH$_3$).

Step 5

1-(2-Isobutoxy-5-trifluoromethoxy-benzyl)-1H-indazole-5-carboxylic acid, 60

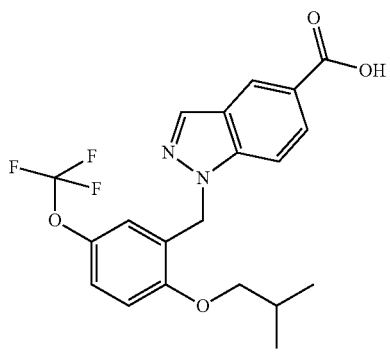 [SMILES: CC(C)COc1ccc(OC(F)(F)F)cc1Cn1ncc2cc(C(=O)O)ccc21]

A solution of 1-(2-Isobutoxy-5-trifluoromethoxy-benzyl)-1H-indazole-5-carboxylicacidmethyl ester (0.217 g, 0.51 mmole) in 1,4-dioxane (20 ml) was treated with 2M sodium hydroxide (20 ml) and the mixture stirred at 60° C. for 18 h. The mixture was evaporated to dryness and the residue dissolved in water (20 ml) then acidified to pH1 with 2M hydrochloric acid. The resulting precipitate was extracted into ethyl acetate (2×50 ml). The combined organics were dried over sodium sulphate, filtered and evaporated to dryness. The residue was chromatographed on silica gel eluting with a gradient of 0.75-2% methanol/dichloromethane to give the title compound as a white solid (0.154 g, 73%).

H-NMR (CDCl$_3$, 300 MHz) δ8.68 (s, 1H, ArH), 8.21 (s, 1H, ArH), 8.11 (dd, 1H, ArH), 7.48 (d, 1H, ArH), 7.11 (dd, 1H, ArH), 6.88 (d, 1H, ArH), 6.72 (s, 1H, ArH), 5.67 (s, 2H, CH$_2$), 3.79 (d, 2H, CH$_2$), 2.05-2.19 (m, 1H, CH), 1.03 (d, 6H, 2×CH$_3$).

LC-MS m/z 409 M+H$^+$.

EXAMPLE 21

1-(5-Bromo-2-Isobutoxy-Benzyl)-3-Methyl-1H-Indazole-5-Carboxylic Acid, 65

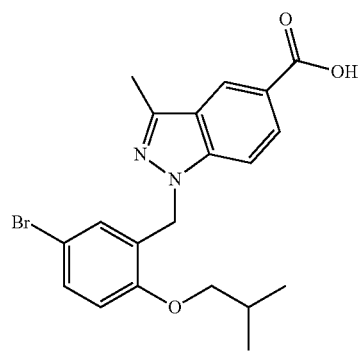

Step 1

5-Bromo-2-isobutoxy-benzaldehyde, 61

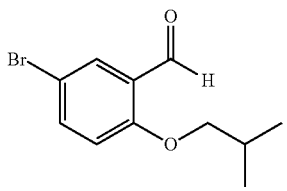

The title compound was prepared following the method in Example 20, Step 1.

H-NMR (CDCl$_3$, 300 MHz) δ10.52 (s, 1H, CHO), 7.95 (d, 1H, ArH), 7.61 (dd, 1H, ArH), 6.93 (s, 1H, ArH), 3.85 (d, 2H, CH$_2$), 2.12-2.24 (m, 1H, CH), 1.09 (d, 6H, 2×CH$_3$).

Step 2

(5-Bromo-2-isobutoxy-phenyl)-methanol, 62

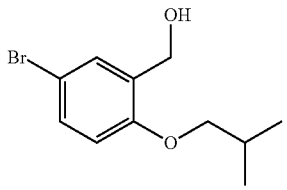

The title compound was prepared following the method in Example 20, Step 2.

H-NMR (CDCl$_3$, 300 MHz) δ 7.45 (d, 1H, ArH), 7.36 (dd, 1H, ArH), 6.77 (d, 1H, ArH), 4.69 (d, 2H, CH$_2$), 3.78 (d, 2H, CH$_2$), 2.27 (t, 1H, OH), 2.07-2.21 (m, 1H, CH), 1.07 (d, 6H, 2×CH$_3$).

Step 3

Methanesulfonic acid 5-bromo-2-isobutoxy-benzyl ester, 63

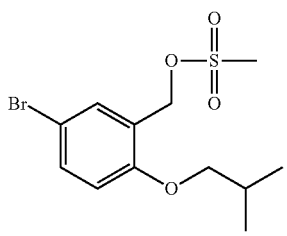 [SMILES: CC(C)COc1ccc(Br)cc1COS(C)(=O)=O]

The title compound was prepared following the method in Example 20, Step 3.

H-NMR (CDCl$_3$, 300 MHz) δ7.49 (d, 1H, ArH), 7.45 (dd, 1H, ArH), 6.79 (d, 1H, ArH), 5.27 (s, 2H, CH$_2$), 3.77 (d, 2H, CH$_2$), 3.01 (s, 3H, CH$_3$), 2.07-2.20 (m, 1H, CH), 1.06 (d, 6H, 2×CH$_3$).

Step 4

1-(5-Bromo-2-isobutoxy-benzyl)-3-methyl-1H-indazole-5-carboxylic acid methyl ester, 64

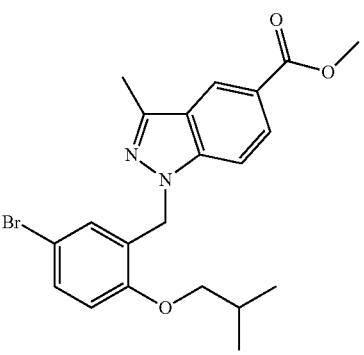 [SMILES: COC(=O)c1ccc2c(c1)c(C)nn2Cc1cc(Br)ccc1OCC(C)C]

To a mixture of methanesulfonic acid 5-bromo-2-isobutoxy-benzyl ester (0.044 g, 0.1 mmole) and 3-Methyl-1H-indazole-5-carboxylic acid methyl ester (0.02 g, 0.1 mmole) in DMF was added cesium carbonate (0.051 g, 0.15 mmole) and the mixture stirred at ambient temperature for 18 h under a nitrogen atmosphere. The mixture was evaporated to dryness and the residue partitioned between water (10 ml) and dichloromethane (2×20 ml). The combined organics were dried over sodium sulphate, filtered and evaporated to dryness. The residue was chromatographed on silica gel eluting with a gradient of 5-20% ethyl acetate/isohexane to give the title compound (0.04 g) as a colorless oil.

H-NMR (CDCl$_3$, 300 MHz) δ8.48 (s, 1H, ArH), 8.02 (d, 1H, ArH), 7.30-7.37 (m, 2H, 2×ArH), 6.96 (d, 1H, ArH), 6.76 (d, 1H, ArH), 5.52 (s, 2H, CH$_2$), 3.99 (s, 3H, CH$_3$), 3.77 (d, 2H, CH$_2$), 2.65 (s, 3H, CH$_3$), 2.05-2.19 (m, 1H, CH), 1.04 (d, 6H, 2×CH$_3$).

Step 5

1-(5-Bromo-2-isobutoxy-benzyl)-3-methyl-1H-indazole-5-carboxylic acid, 65

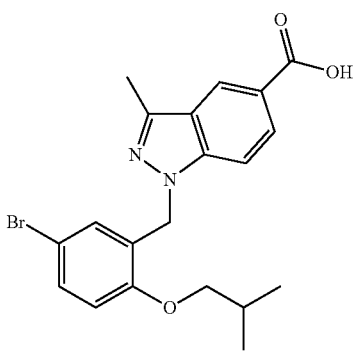 [SMILES: Cc1nn(Cc2cc(Br)ccc2OCC(C)C)c2ccc(C(=O)O)cc12]

The title compound was prepared following the method in Example 20, Step 5.

1H-NMR (CDCl$_3$, 300 MHz) δ8.59 (s, 1H, ArH), 8.09 (d, 1H, ArH), 7.33-7.41 (m, 2H, 2×ArH), 6.98 (d, 1H, ArH), 6.77 (d, 1H, ArH), 5.59 (s, 2H, CH$_2$), 3.78 (d, 2H, CH$_2$), 2.68 (s, 3H, CH$_3$), 2.07-2.20 (m, 1H, CH), 1.06 (d, 6H, 2×CH$_3$).

LC-MS m/z 417 and 419 M+H$^+$.

EXAMPLE 22

1-(2-Isobutoxy-5-Trifluoromethoxy-Benzyl)-3-Methyl-1H-Indazole-5-Carboxylic Acid, 66

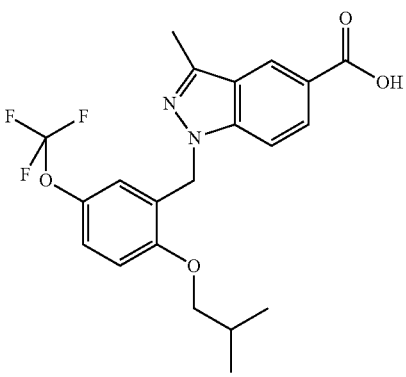 [SMILES: Cc1nn(Cc2cc(OC(F)(F)F)ccc2OCC(C)C)c2ccc(C(=O)O)cc12]

The title compound was prepared following the methods described on Example 21 but using compound 58 as the starting material.

1H-NMR (CDCl$_3$, 300 MHz) δ 8.55 (s, 1H, ArH), 8.08 (dd, 1H, ArH), 7.35 (d, 1H, ArH), 7.11 (dd, 1H, ArH), 6.95 (d, 1H, ArH), 6.71 (d, 1H, ArH), 5.58 (s, 2H, CH$_2$), 3.79 (d, 2H, CH$_2$), 2.66 (s, 3H, CH$_3$), 2.07-2.21 (m, 1H, CH), 1.05 (d, 6H, 2×CH$_3$).

EXAMPLE 23

1-[5-Chloro-2-(2-Ethyl-Butoxy)-Benzyl]-3-Methyl-1H-Indazole-5-Carboxylic Acid, 67

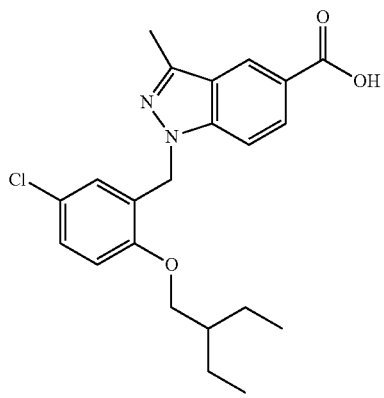 [SMILES: CCC(CC)COc1ccc(Cl)cc1Cn1nc(C)c2cc(C(=O)O)ccc21]

The title compound was prepared following the methods described on Example 21 but using 2-Hydroxy-5-chloro-benzaldehyde as starting material.

1H-NMR (CDCl$_3$, 300 MHz) δ 8.58 (s, 1H, ArH), 8.07 (dd, 1H, ArH), 7.34 (d, 1H, ArH), 7.18 (dd, 1H, ArH), 6.85 (d, 1H, ArH), 6.76 (d, 1H, ArH), 5.56 (s, 2H, CH$_2$), 3.91 (d, 2H, CH$_2$), 2.66 (s, 3H, CH$_3$), 1.63-1.78 (m, 1H, CH), 1.41-1.53 (m, 4H, 2×CH$_2$), 0.94 (t, 6H, 2×CH$_3$).

EXAMPLE 24

1-(5-Chloro-2-Isobutoxy-Benzyl)-3-Methyl-1H-Indazole-5-Carboxylic Acid, 68

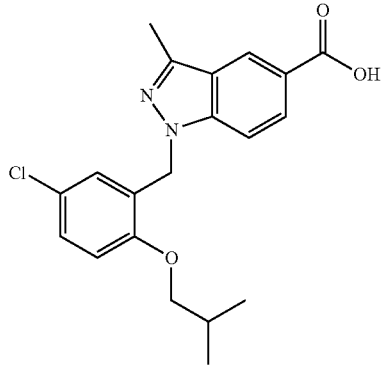 [SMILES: Cc1nn(Cc2cc(Cl)ccc2OCC(C)C)c2ccc(C(=O)O)cc12]

The title compound was prepared following the methods described on Example 21 but using 2-Hydroxy-5-chloro-benzaldehyde as starting material.

1H-NMR (CDCl$_3$, 300 MHz) δ 8.59 (s, 1H, ArH), 8.09 (dd, 1H, ArH), 7.37 (d, 1H, ArH), 7.18 (dd, 1H, ArH), 6.79 (s, 1H, ArH), 6.77 (d, 1H, ArH), 5.55 (s, 2H, CH$_2$), 3.78 (d, 2H, CH$_2$), 2.67 (s, 3H, CH$_3$), 2.04-2.29 (m, 1H, CH), 1.03 (d, 6H, 2×CH$_3$).

EXAMPLE 25

1-(2-Isobutoxy-5-Trifluoromethyl-Benzyl)-3-Methyl-1H-Indazole-5-Carboxylic Acid, 69

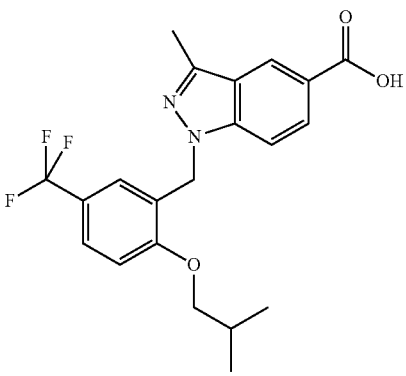 [SMILES: Cc1nn(Cc2cc(C(F)(F)F)ccc2OCC(C)C)c2ccc(C(=O)O)cc12]

The title compound was prepared following the methods described on Example 21 but using 2-Hydroxy-5-(trifluoromethyl)-benzaldehyde as starting material.

1H-NMR (CDCl$_3$, 300 MHz) δ 8.59 (s, 1H, ArH), 8.11 (dd, 1H, ArH), 7.55 (dd, 1H, ArH), 7.39 (d, 1H, ArH), 7.19 (d, 1H, ArH), 6.97 (d, 1H, ArH), 5.61 (s, 2H, CH$_2$), 3.85 (d, 2H, CH$_2$), 2.69 (s, 3H, CH$_3$), 2.05-2.21 (m, 1H, CH), 1.03 (d, 6H, 2×CH$_3$).

EXAMPLE 26

1-[2-(2-Ethyl-Butoxy)-5-Trifluoromethyl-Benzyl]-3-Methyl-1H-Indazole-5-Carboxylic Acid, 70

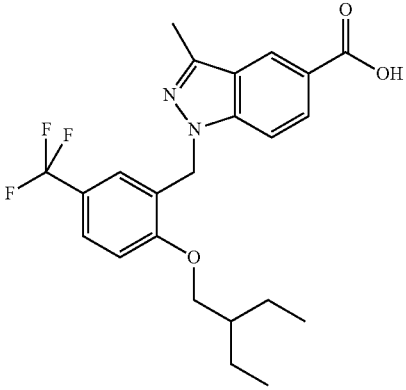 [SMILES: CCC(CC)COc1ccc(C(F)(F)F)cc1Cn1nc(C)c2cc(C(=O)O)ccc21]

The title compound was prepared following the methods described on Example 21 but using 2-Hydroxy-5-(trifluoromethyl)-benzaldehyde as starting material.

1H-NMR (CDCl$_3$, 300 MHz) δ 8.59 (s, 1H, ArH), 8.09 (dd, 1H, ArH), 7.56 (dd, 1H, ArH), 7.38 (d, 1H, ArH), 7.16 (d, 1H, ArH), 6.99 (d, 1H, ArH), 5.61 (s, 2H, CH$_2$), 3.97 (d, 2H, CH$_2$), 2.66 (s, 3H, CH$_3$), 1.68-1.79 (m, 1H, CH), 1.45-1.54 (m, 4H, 2×CH$_2$), 0.97 (t, 6H, 2×CH$_3$).

EXAMPLE 27

1-[5-Bromo-2-(2-Ethyl-Butoxy)-Benzyl]-3-Methyl-1H-Indazole-5-Carboxylic Acid, 71

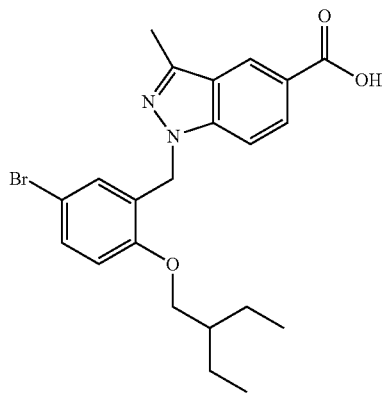

The title compound was prepared following the methods described on Example 21 but using 2-Hydroxy-5-bromo-benzaldehyde as starting material.

1H-NMR (CDCl$_3$, 300 MHz) δ 8.59 (s, 1H, ArH), 8.09 (dd, 1H, ArH), 7.31-7.39 (m, 2H, 2×ArH), 6.96 (d, 1H, ArH), 6.79 (d, 1H, ArH), 5.55 (s, 2H, CH$_2$), 3.92 (d, 2H, CH$_2$), 2.69 (s, 3H, CH$_3$), 1.66-1.76 (m, 1H, CH), 1.42-1.54 (m, 4H, 2×CH$_2$), 0.95 (t, 6H, 2×CH$_3$).

EXAMPLE 28

1-[5-Bromo-2-(1-Methyl-Cyclopropylmethoxy)-Benzyl]-3-Methyl-1H-Indazole-5-Carboxylic Acid, 72

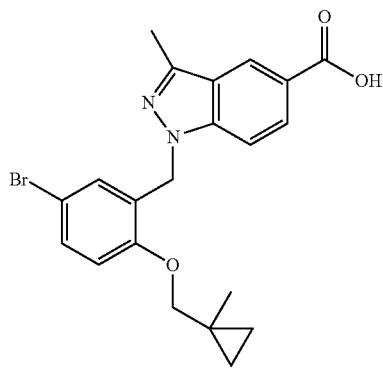

The title compound was prepared following the methods described on Example 21 but using 2-Hydroxy-5-bromo-benzaldehyde as starting material.

1H-NMR (CDCl$_3$, 300 MHz) δ 8.59 (s, 1H, ArH), 8.12 (dd, 1H, ArH), 7.48 (d, 1H, ArH), 7.34 (dd, 1H, ArH), 7.09 (d, 1H, ArH), 6.71 (d, 1H, ArH), 5.58 (s, 2H, CH$_2$), 3.77 (s, 2H, CH$_2$), 2.67 (s, 3H, CH$_3$), 1.23 (s, 3H, CH$_3$), 0.42-0.59 (m, 4H, 2×CH$_2$).

EXAMPLE 29

1-[5-Chloro-2-(1-Methyl-Cyclopropylmethoxy)-Benzyl]-3-Methyl-1H-Indazole-5-Carboxylic Acid, 73

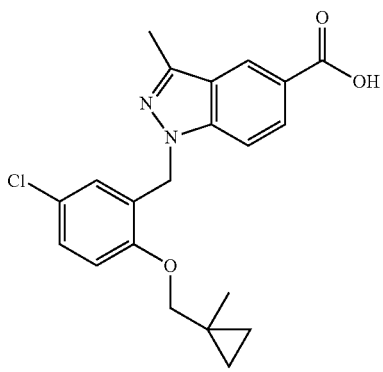 [SMILES: Cc1nn(Cc2cc(Cl)ccc2OCC2(C)CC2)c2ccc(C(=O)O)cc12]

The title compound was prepared following the methods described on Example 21 but using 2-Hydroxy-5-chloro-benzaldehyde as starting material.

1H-NMR (CDCl$_3$, 300 MHz) δ 8.58 (s, 1H, ArH), 8.08 (d, 1H, ArH), 7.47 (d, 1H, ArH), 7.19 (dd, 1H, ArH), 6.95 (d, 1H, ArH), 6.74 (d, 1H, ArH), 5.58 (s, 2H, CH$_2$), 3.78 (s, 2H, CH$_2$), 2.69 (s, 3H, CH$_3$), 1.22 (s, 3H, CH$_3$), 0.43-0.57 (m, 4H, 2×CH$_2$).

EXAMPLE 30

1-(5-Bromo-2-Isobutoxy-Benzyl)-1H-Pyrrolo[2,3-b]Pyridine-5-Carboxylic Acid, 77

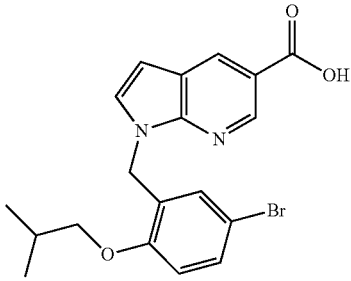 [SMILES: CC(C)COc1ccc(Br)cc1Cn1ccc2cc(C(=O)O)cnc21]

Step 1

5-bromo-1H-pyrrolo[2,3-b]pyridine, 74

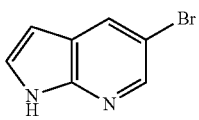

Following the preparation procedure described in WO2006015124, which is hereby incorporated by reference in its entirety, 5-bromo-1H-pyrrolo[2,3-b]pyridine was isolated after column chromatography on silica as a light brown solid (30% over 3 steps). LC-MS: m/z 198, 200 M+H+.

Step 2

1h-pyrrolo[2,3-b]pyridine-5-carboxylic acid methyl ester, 75

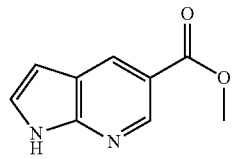

To a mixture of 5-Bromo-1H-pyrrolo[2,3-b]pyridine 0.6 g (3 mmol), molybdenum hexacarbonate 0.4 g (1.5 mmol), Herrmann's catalyst 0.28 g, 4,4-bis(diphenylphosphino)-9,9-dimethylxanthane and triethylamine 0.85 ml (6 mmol) in a 20 ml microwave reactor THF (10 ml) and methanol (2 ml) was added. The resulting suspension was heated at 150° C. on microwave for 10 minutes. The mixture was poured into sat NH4Cl (aq.) and extracted twice with EtOAC. The organic layers were combined, washed with sat NH4Cl (aq.), dried (MgSO4) and the volatiles were removed in vacuo. The crude product was purified on silica to yield 1H-Pyrrolo[2,3-b]pyridine-5-carboxylic acid methyl ester 2 0.16 g as a brown solid (30%).

$^1$H-NMR (CDCl$_3$, 300 MHz) δ 9.28 (d, 1H, ArH), 8.86 (d, 1H, ArH), 8.25 (s, 1H, ArH), 4.02 (s, 3H, CH$_3$)

LC-MS: m/z 178 M+H+.

Step 3

1-(5-Bromo-2-isobutoxy-benzyl)-1H-pyrazolo[3,4-b]pyridine-5-carboxylic acid methyl ester, 76

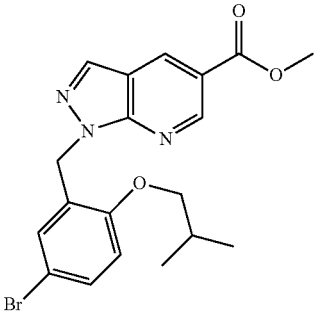 [SMILES: COC(=O)c1cnc2c(cnn2Cc2cc(Br)ccc2OCC(C)C)c1]

The title compound was prepared following the method in Example 21, Step 4.

$^1$H-NMR (CDCl$_3$, 300 MHz) δ 9.22 (d, 1H, ArH), 8.79 (d, 1H, ArH), 8.19 (s, 1H, ArH), 7.34 (dd, 1H, ArH), 6.98 (d, 1H, ArH), 6.74 (d, 1H, ArH), 5.77 (s, 2H, ArCH$_2$), 4.01 (s, 3H, CH$_3$), 3.72 (d, 2H, CH$_2$). 2.01 (m, 1H, CH), 0.97 (d, 6H, CH$_3$).

LC-MS: m/z 374, 376 M+H+

Step 4

1-(5-bromo-2-isobutoxy-benzyl)-1h-pyrazolo[3,4-b]pyridine-5-carboxylic acid, 77

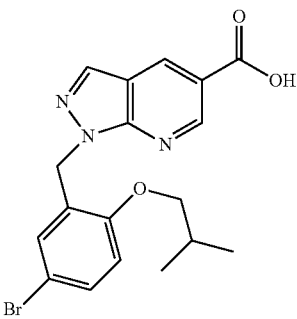 [SMILES: CC(C)COc1ccc(Br)cc1Cn1ncc2cc(C(=O)O)cnc21]

The title compound was prepared following the method in Example 20, Step 5.

$^1$H-NMR (CDCl$_3$, 300 MHz) δ 9.28 (s, 1H, ArH), 8.85 (s, 1H, ArH), 8.18 (s, 1H, ArH), 7.33 (d, 1H, ArH), 6.99 (s, 1H, ArH), 6.74 (d, 1H, ArH), 5.76 (s, 2H, ArCH$_2$), 3.71 (d, 2H, CH$_2$). 2.01 (m, 1H, CH), 0.96 (d, 6H, CH$_3$).

LC-MS: m/z 405 M+H+

EXAMPLE 31

1-[5-Bromo-2-(2-Ethyl-Butoxy)-Benzyl]-1H-Pyrrolo[2,3-b]Pyridine-5-Carboxylic Acid, 82

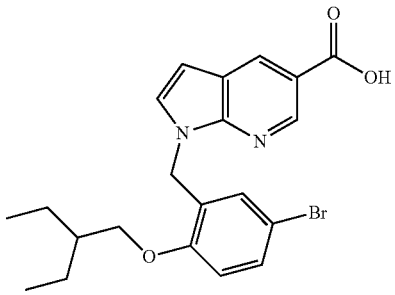 [SMILES: CCC(CC)COc1ccc(Br)cc1Cn1ccc2cc(C(=O)O)cnc21]

Step 1

5-Bromo-2-(2-ethyl-butoxy)-benzaldehyde 78

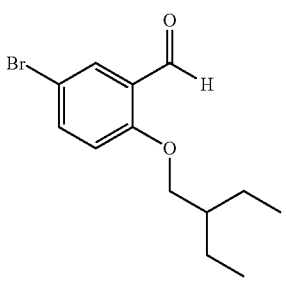

A solution of 5-bromosalicaldehyde (2.0 g, 10 mmole) in DMF (50 ml) was treated with potassium carbonate (3 g, 22 mmole) and tetrabutylammonium iodide (0.22 g) and 3-chloromethylpentane (1.65 ml, 12.2 mmole). The mixture was stirred at 110° C. under a nitrogen atmosphere for 18 h. The mixture was then evaporated to dryness and the residue partitioned between ethyl acetate (50 ml) and water (50 ml). The organic extract was separated then washed with saturated brine then dried over sodium sulphate, filtered and evaporated to dryness. The residue was chromatographed on silica gel eluting with a gradient of 5-15% ethyl acetate/isohexane. This gave the title compound as a pale yellow oil (2.24 g, 78%).

$^1$H-NMR (CDCl$_3$, 300 MHz) δ10.49 (s, 1H, CHO), 7.95 (d, 1H, ArH), 7.63 (dd, 1H, ArH), 6.90 (d, 1H, ArH), 4.00 (d, 2H, CH$_2$), 1.80 (m, 1H, CH), 1.55 (s, 4H, 2×CH$_2$—CH$_3$), 1.00 (q, 6H, 2×CH$_2$—CH$_3$)

Step 2

[5-Bromo-2-(2-ethyl-butoxy)-phenyl]methanol, 79

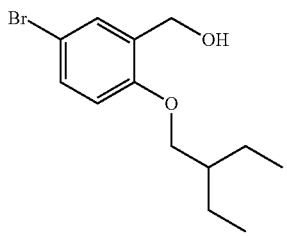

The title compound was prepared following the method in Example 20, Step 2.

$^1$H-NMR (CDCl$_3$, 300 MHz) δ7.45 (d, 1H, ArH), 7.37 (dd, 1H, ArH), 6.80 (d, 1H, ArH), 4.70 (d, 2H, —CH$_2$OH), 3.90 (d, 2H, CH$_2$), 1.80 (m, 1H, CH), 1.55 (s, 4H, 2×CH$_2$—CH$_3$), 1.00 (q, 6H, 2×CH$_2$—CH$_3$).

Step 3

Methanesulfonic acid 5-bromo-2-(2-ethyl-butoxy)-benzyl ester, 80

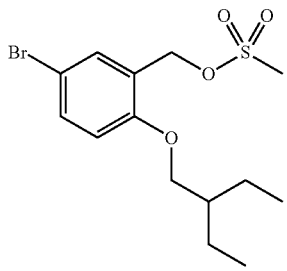

The title compound was prepared following the method in Example 20, Step 3.

$^1$H-NMR (CDCl$_3$, 300 MHz) δ7.55 (d, 1H, ArH), 7.45 (dd, 1H, ArH), 6.80 (d, 1H, ArH), 5.75 (d, 2H, —CH$_2$OSO$_2$CH$_3$), 3.90 (d, 2H, CH$_2$), 3.00 (s, 3H, CH$_2$OSO$_2$CH$_3$), 1.80 (m, 1H, CH), 1.55 (s, 4H, 2×CH$_2$—CH$_3$), 1.00 (q, 6H, 2×CH$_2$—CH$_3$)

Step 4

1-[5-Bromo-2-(2-ethyl-butoxy)-benzyl]-1H-pyrazolo[3,4-b]pyridine-5-carboxylic acid methyl ester, 81

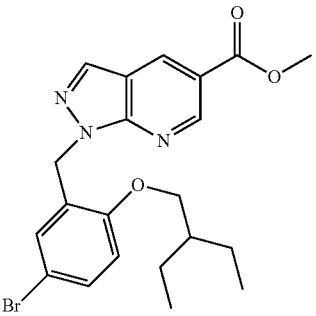

The title compound was prepared following the method in Example 21, Step 4.

$^1$H-NMR (CDCl$_3$, 300 MHz) δ 9.21 (d, 1H, ArH), 8.80 (d, 1H, ArH), 8.19 (s, 1H, ArH), 7.34 (dd, 1H, ArH), 6.95 (d, 1H, ArH), 6.77 (d, 1H, ArH), 5.76 (s, 2H, ArCH$_2$), 4.01 (s, 3H, CH$_3$), 3.85 (d, 2H, CH$_2$). 1.60 (m, 1H, CH), 1.39 (m, 4H, CH$_2$), 0.88 (m, 6H, CH$_3$).

LC-MS: m/z 446, 448 M+H$^+$

Step 5

1-[5-bromo-2-(2-ethyl-butoxy)-benzyl]-1h-pyrazolo[3,4-b]pyridine-5-carboxylic acid, 82

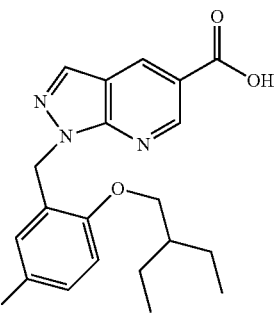

The title compound was prepared following the method in Example 20, Step 5.

$^1$H-NMR (CDCl$_3$, 300 MHz) δ 9.30 (d, 1H, ArH), 8.87 (d, 1H, ArH), 8.24 (s, 1H, ArH), 7.36 (dd, 1H, ArH), 7.00 (d, 1H, ArH), 6.78 (d, 1H, ArH), 5.78 (s, 2H, ArCH$_2$), 3.86 (d, 2H, CH$_2$). 1.60 (m, 1H, CH), 1.39 (m, 4H, CH$_2$), 0.89 (m, 6H, CH$_3$).

LC-MS: m/z 432,434 M+H$^+$.

EXAMPLE 32

1-[2-(4-Chloro-Benzyloxy)-5-Trifluoromethyl-Benzyl]-1H-Indazole-5-Carboxylic Acid, 83

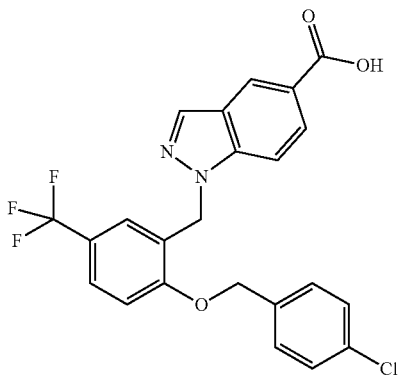 [SMILES: O=C(O)c1ccc2c(cnn2Cc2cc(C(F)(F)F)ccc2OCc2ccc(Cl)cc2)c1]

The title compound was prepared starting from compound 51 and following the methods in Example 8, Step 1 and Example 1, step 3.

$^1$H-NMR (CDCl$_3$, 300 MHz) δ 8.65 (s, 1H, ArH), 8.20 (s, 1H, ArH), 8.00 (d, 1H, ArH), 7.55 (d, 1H, ArH), 7.40-7.20 (m, 6H, ArH), 7.00 (d, 1H, ArH), 5.65 (s, 2H, ArCH$_2$O), 5.05 (s, 2H, ArCH$_2$Het).

LC-MS: m/z 461 M+H$^+$.

EXAMPLE 33

1-(2-Cyclopentylmethoxy-5-Trifluoromethyl-Benzyl)-1H-Indazole-5-Carboxylic Acid, 84

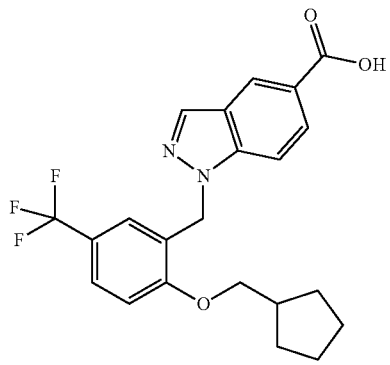 [SMILES: O=C(O)c1ccc2c(cnn2Cc2cc(C(F)(F)F)ccc2OCC2CCCC2)c1]

The title compound was prepared starting from compound 51 and following the methods in Example 3, Step 3 and Example 1, step 3.

$^1$H-NMR (CDCl$_3$, 300 MHz) δ 8.55 (s, 1H, ArH), 8.20 (s, 1H, ArH), 8.10 (d, 1H, ArH), 7.65 (d, 1H, ArH), 7.53 (d, 1H, ArH), 7.42 (s, 1H, ArH), 6.87 (d, 1H, ArH), 5.65 (s, 2H, ArCH$_2$Het), 4.85 (d, 2H, —CH$_2$O—), 1.7 (m, 1H, CH), 1.4-0.6 (m, 8H, —CH$_2$—).

LC-MS: m/z 391 M+H$^+$.

EXAMPLE 34

1-(5-Chloro-2-Cyclopropylmethoxy-Benzyl)-1H-Indazole-4-Carboxylic Acid, 85

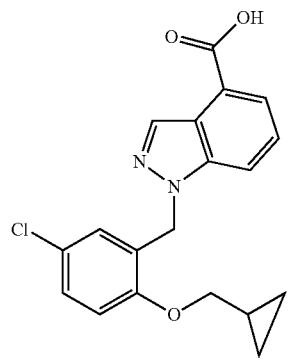 [SMILES: O=C(O)c1cccc2c1cnn2Cc1cc(Cl)ccc1OCC1CC1]

The title compound was prepared following the same method as Example 7.

$^1$H-NMR (CDCl$_3$, 300 MHz) δ 8.62 (s, 1H, ArH), 8.05 (d, 1H, ArH), 7.82 (d, 1H, ArH), 7.45 (m, 1H, ArH), 7.20 (m, 1H, ArH), 7.00 (s, 1H, ArH), 6.75 (m, 1H, ArH), 5.65 (s, 2H, ArCH$_2$Het), 3.80 (d, 2H, —CH$_2$O—), 1.55 (m, 1H, CH), 0.7 (m, 2H, —CH$_2$—), 0.4 (m, 2H, —CH$_2$—). LC-MS: m/z 357 M+H$^+$.

EXAMPLE 35

2-(5-Chloro-2-Cyclopropylmethoxy-Benzyl)-2H-Indazole-4-Carboxylic Acid, 86

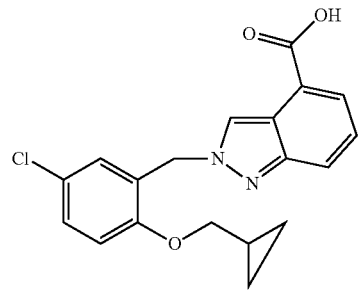 [SMILES: O=C(O)c1cccc2nn(Cc3cc(Cl)ccc3OCC3CC3)cc12]

The title compound was prepared following the same method as Example 7.

$^1$H-NMR (DMSO, 300 MHz) δ 8.70 (s, 1H, ArH), 8.05 (d, 1H, ArH), 7.85 (d, 1H, ArH), 7.75 (d, 1H, ArH), 7.32 (m, 2H, ArH), 7.20 (s, 1H, ArH), 7.00 (d, 1H, ArH), 5.65 (s, 2H, ArCH$_2$Het), 3.85 (d, 2H, —CH$_2$O—), 1.70 (m, 1H, CH), 0.55 (m, 2H, —CH$_2$—), 0.3 (m, 2H, —CH$_2$—). LC-MS: m/z 357 M+H$^+$.

Example 36

1-(5-Chloro-2-Isobutoxy-Benzyl)-1H-Indazole-4-Carboxylic Acid, 87

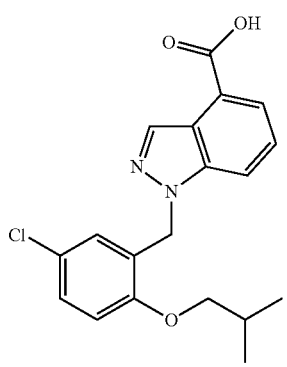 [SMILES: CC(C)COc1ccc(Cl)cc1Cn1ncc2c(C(=O)O)cccc21]

The title compound was prepared following the same method as Example 7.

$^1$H-NMR (CDCl$_3$, 300 MHz) δ 8.62 (s, 1H, ArH), 8.05 (d, 1H, ArH), 7.70 (d, 1H, ArH), 7.45 (m, 1H, ArH), 7.15 (m, 1H, ArH), 6.80 (m, 2H, ArH), 5.65 (s, 2H, ArCH$_2$Het), 3.75 (d, 2H, —CH$_2$O—), 2.10 (m, 1H, CH), 1.05 (d, 6H, —CH$_3$). LC-MS: m/z 359 M+H$^+$.

Example 37

2-(5-Chloro-2-Isobutoxy-Benzyl)-2H-Indazole-4-Carboxylic Acid, 88

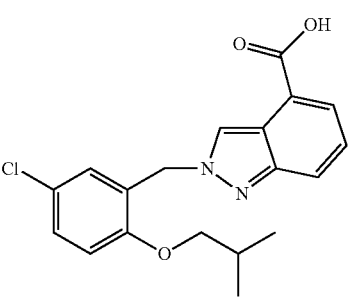 [SMILES: CC(C)COc1ccc(Cl)cc1Cn1cc2c(C(=O)O)cccc2n1]

The title compound was prepared following the same method as Example 7.

$^1$H-NMR (CDCl$_3$, 300 MHz) δ 8.55 (s, 1H, ArH), 8.15 (m, 2H, ArH), 7.40 (t, 1H, ArH), 7.25 (m, 1H, ArH), 7.10 (s, 1H, ArH), 6.80 (d, 1H, ArH), 5.65 (s, 2H, ArCH$_2$Het), 3.75 (d, 2H, —CH$_2$O—), 2.15 (m, 1H, CH), 1.05 (d, 6H, —CH$_3$).

LC-MS: m/z 359 M+H$^+$.

Example 38

1-[5-Chloro-2-(2-Ethyl-Butoxy)-Benzyl]-1H-Indazole-4-Carboxylic Acid, 89

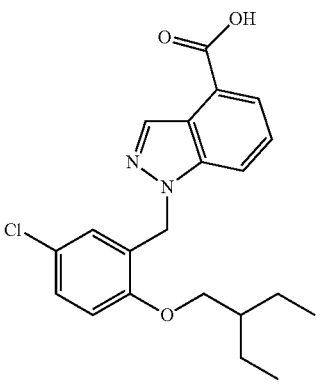 [SMILES: CCC(CC)COc1ccc(Cl)cc1Cn1ncc2c(C(=O)O)cccc21]

The title compound was prepared following the same method as Example 7.

$^1$H-NMR (CDCl$_3$, 300 MHz) δ 8.65 (s, 1H, ArH), 8.05 (d, 1H, ArH), 7.65 (d, 1H, ArH), 7.52 (t, 1H, ArH), 7.18 (m, 1H, ArH), 6.85 (d, 1H, ArH), 6.75 (m, 1H, ArH), 5.65 (s, 2H, ArCH$_2$Het), 3.90 (d, 2H, —CH$_2$O—), 1.50 (m, 1H, CH), 1.45 (t, 4H, —CH$_2$CH$_3$), 0.95 (t, 6H, —CH$_2$CH$_3$). LC-MS: m/z 387 M+H$^+$.

Example 39

2-[5-Chloro-2-(2-Ethyl-Butoxy)-Benzyl]-2H-Indazole-4-Carboxylic Acid, 90

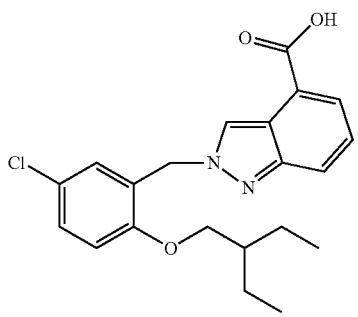 [SMILES: CCC(CC)COc1ccc(Cl)cc1Cn1cc2c(C(=O)O)cccc2n1]

The title compound was prepared following the same method as Example 7.

$^1$H-NMR (CDCl$_3$, 300 MHz) δ 8.50 (s, 1H, ArH), 8.02 (m, 2H, ArH), 7.40 (t, 1H, ArH), 7.25 (m, 1H, ArH), 7.15 (s, 1H, ArH), 6.82 (d, 1H, ArH), 5.65 (s, 2H, ArCH$_2$Het), 3.90 (d, 2H, —CH$_2$O—), 1.70 (m, 1H, CH), 1.45 (t, 4H, —CH$_2$CH$_3$), 0.85 (t, 6H, —CH$_2$CH$_3$).

LC-MS: m/z 387 M+H$^+$.

Example 40

1-[5-Chloro-2-(4-Chloro-Benzyloxy)-Benzyl]-1H-Indazole-4-Carboxylic Acid, 91

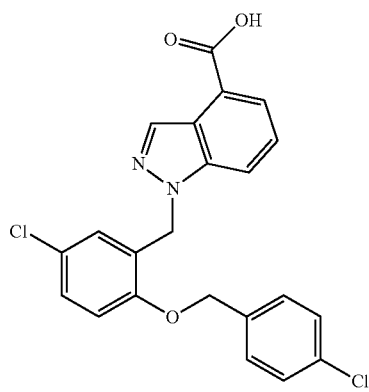 [SMILES: O=C(O)c1cccc2c1cnn2Cc1cc(Cl)ccc1OCc1ccc(Cl)cc1]

The title compound was prepared following the same method as Example 7.

¹H-NMR (CDCl₃, 300 MHz) δ 8.52 (s, 1H, ArH), 8.02 (d, 1H, ArH), 7.55 (d, 1H, ArH), 7.40-7.20 (m, 6H, ArH), 7.00 (s, 1H, ArH), 6.85 (d, 1H, ArH), 5.65 (s, 2H, ArCH₂Het), 5.05 (s, 2H, ArCH₂O—). LC-MS: m/z 427 M+H⁺.

Example 41

2-[5-Chloro-2-(4-Chloro-Benzyloxy)-Benzyl]-2H-Indazole-4-Carboxylic Acid, 92

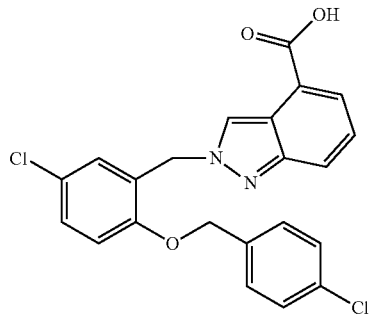 [SMILES: O=C(O)c1cccc2nn(Cc3cc(Cl)ccc3OCc3ccc(Cl)cc3)cc12]

The title compound was prepared following the same method as Example 7.

¹H-NMR (DMSO, 300 MHz) δ 13.00 (s, 1H, COOH), 8.65 (s, 1H, ArH), 7.90 (m, 1H, ArH), 7.80 (d, 1H, ArH), 7.40 (m, 6H, ArH), 7.25 (s, 1H, ArH), 7.10 (d, 1H, ArH), 5.70 (s, 2H, ArCH₂Het), 5.15 (s, 2H, ArCH₂O—). LC-MS: m/z 427 M+H⁺.

Example 42

1-(5-Bromo-2-Isobutoxy-Benzyl)-1H-Indazole-6-Carboxylic Acid, 93

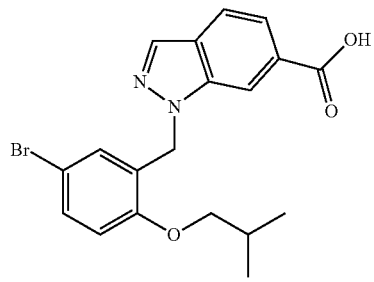 [SMILES: CC(C)COc1ccc(Br)cc1Cn1ncc2ccc(C(=O)O)cc21]

The title compound was prepared following the same method as Example 7.

¹H-NMR (DMSO, 300 MHz) δ 13.00 (s, 1H, COOH), 8.30 (s, 1H, ArH), 8.20 (s, 1H, ArH), 7.85 (d, 1H, ArH), 7.70 (d, 1H, ArH), 7.40 (m, 1H, ArH), 7.15 (s, 1H, ArH), 6.95 (d, 1H, ArH), 5.65 (s, 2H, ArCH₂Het), 3.70 (d, 2H, —CH₂O—), 1.95 (m, 1H, CH), 0.85 (d, 6H, —CH₃). LC-MS: m/z 404 M+H⁺.

Example 43

2-(5-Bromo-2-Isobutoxy-Benzyl)-2H-Indazole-6-Carboxylic Acid, 94

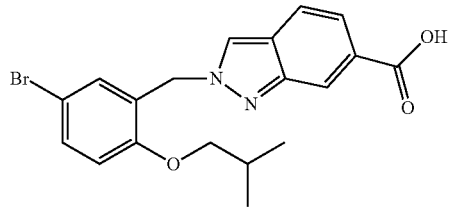 [SMILES: CC(C)COc1ccc(Br)cc1Cn1cc2ccc(C(=O)O)cc2n1]

The title compound was prepared following the same method as Example 7.

¹H-NMR (CDCl₃, 300 MHz) δ 8.60 (s, 1H, ArH), 8.00 (s, 1H, ArH), 7.70 (m, 2H, ArH), 7.40 (m, 1H, ArH), 7.25 (m, 1H, ArH), 6.75 (d, 1H, ArH), 5.65 (s, 2H, ArCH₂Het), 3.75 (d, 2H, —CH₂O—), 2.10 (m, 1H, CH), 1.00 (d, 6H, —CH₃). LC-MS: m/z 404 M+H⁺.

Example 44

1-(5-Bromo-2-Cyclopentylmethoxy-Benzyl)-1H-Indazole-6-Carboxylic Acid, 95

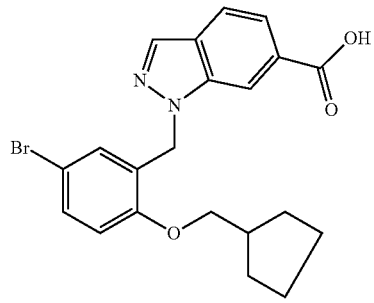 [SMILES: O=C(O)c1ccc2cnn(Cc3cc(Br)ccc3OCC3CCCC3)c2c1]

The title compound was prepared following the same method as Example 7.

¹H-NMR (CDCl₃, 300 MHz) δ 8.30 (s, 1H, ArH), 8.15 (s, 1H, ArH), 7.85 (q, 2H, ArH), 7.30 (m, 1H, ArH), 7.05 (s, 1H, ArH), 6.75 (d, 1H, ArH), 5.65 (s, 2H, ArCH₂Het), 3.87 (d, 2H, —CH₂O—), 2.45 (m, 1H, CH), 1.85 (m, 2H, —CH₂—CH₂—), 1.65 (m, 4H, —CH₂—CH₂—), 1.30 (m, 2H, —CH₂—CH₂—). LC-MS: m/z 430 M+H⁺.

Example 45

2-(5-Bromo-2-Cyclopentylmethoxy-Benzyl)-2H-Indazole-6-Carboxylic Acid, 96

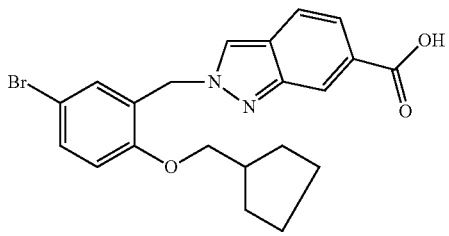 [SMILES: O=C(O)c1ccc2cn(Cc3cc(Br)ccc3OCC3CCCC3)nc2c1]

The title compound was prepared following the same method as Example 7.

¹H-NMR (CDCl₃, 300 MHz) δ 8.65 (s, 1H, ArH), 8.00 (s, 1H, ArH), 7.70 (q, 2H, ArH), 7.37 (m, 1H, ArH), 7.25 (m, 1H, ArH), 6.75 (d, 1H, ArH), 5.65 (s, 2H, ArCH₂Het), 3.85 (d, 2H, —CH₂O—), 2.35 (m, 1H, CH), 1.80 (m, 2H, —CH₂—CH₂—), 1.55 (m, 4H, —CH₂—CH₂—), 1.30 (m, 2H, —CH₂—CH₂—). LC-MS: m/z 430 M+H⁺.

Example 46

1-[5-Chloro-2-(2-Ethyl-Butoxy)-Benzyl]-1H-Indazole-6-Carboxylic Acid, 97

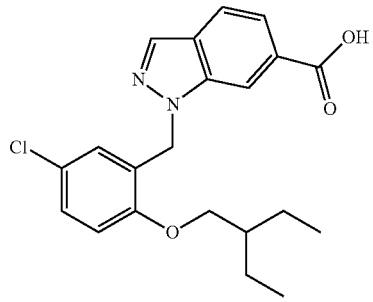 [SMILES: CCC(CC)COc1ccc(Cl)cc1Cn1ncc2ccc(C(=O)O)cc21]

The title compound was prepared following the same method as Example 7.

¹H-NMR (CDCl₃, 300 MHz) δ 8.25 (s, 1H, ArH), 8.15 (s, 1H, ArH), 7.85 (q, 2H, ArH), 7.15 (m, 1H, ArH), 6.80 (m, 2H, ArH), 5.65 (s, 2H, ArCH₂Het), 3.90 (d, 2H, —CH₂O—), 1.75 (m, 1H, CH), 1.45 (q, 4H, —CH₂—CH₃), 0.95 (t, 6H, —CH₂—CH₃). LC-MS: m/z 387 M+H⁺.

Example 47

1-(5-Chloro-3-Fluoro-2-Isobutoxy-Benzyl)-1H-Indazole-5-Carboxylic Acid, 98

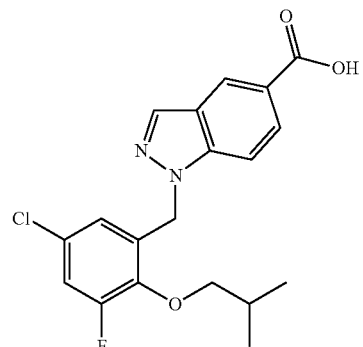

The title compound was prepared following the same method as Example 3 but using (5-chloro-3-fluoro-2-methoxy-phenyl)-methanol as the starting material.

¹H-NMR (CDCl₃, 300 MHz) δ 8.60 (s, 1H, ArH), 8.17 (m, 2H, ArH), 7.62 (d, 1H, ArH), 7.14 (m, 1H, ArH), 6.90 (t, 1H, ArH), 5.74 (s, 2H, ArCH₂Het), 3.76 (d, 2H, —CH₂O—), 2.11 (m, 1H, CH), 1.03 (d, 6H, —CH₃). LC-MS: m/z 377 M+H⁺.

Example 48

1-(2-Isobutoxy-5-Methanesulfonyl-Benzyl)-1H-Indazole-5-Carboxylic Acid, 99

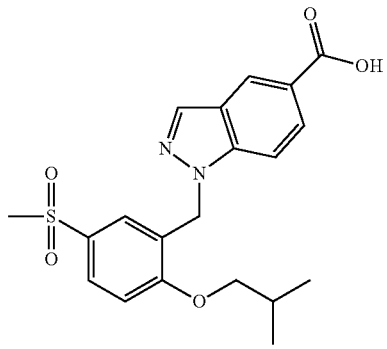 [SMILES: CC(C)COc1ccc(S(C)(=O)=O)cc1Cn1ncc2cc(C(=O)O)ccc21]

The title compound was prepared following the same method as Example 3 but using (5-methylsulphone-2-methoxy-phenyl)-methanol as the starting material.

¹H-NMR (CDCl₃, 300 MHz) δ 8.53 (s, 1H, ArH), 8.14 (s, 1H, ArH), 8.03 (m, 1H, ArH), 7.81 (m, 1H, ArH), 7.45 (m, 1H, ArH), 7.40 (d, 1H, ArH), 6.97 (d, 1H, ArH), 5.61 (s, 2H, ArCH₂Het), 3.81 (d, 2H, —CH₂O—), 2.92 (s, 3H, SO₂CH₃), 2.05 (m, 1H, CH), 0.95 (d, 6H, —CH₃).

LC-MS: m/z 402 M+H⁺.

Example 49

1-(4,5-Dichloro-2-Isobutoxy-Benzyl)-1H-Indazole-5-Carboxylic Acid, 100

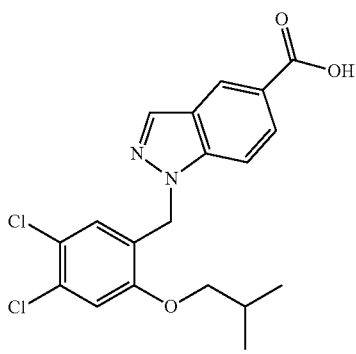 [SMILES: CC(C)COc1cc(Cl)c(Cl)cc1Cn1ncc2cc(C(=O)O)ccc21]

The title compound was prepared following the same method as Example 3 but using (4,5-dichloro-2-methoxyphenyl)-methanol as the starting material.

¹H-NMR (CDCl₃, 300 MHz) δ 8.45 (s, 1H, ArH), 8.05 (m, 1H, ArH), 7.95 (d, 1H, ArH), 7.31 (d, 1H, ArH), 6.83 (d, 2H, ArH), 5.45 (s, 2H, ArCH₂Het), 3.65 (d, 2H, —CH₂O—), 1.98 (m, 1H, CH), 0.89 (d, 6H, —CH₃). LC-MS: m/z 393 M+H⁺.

Example 50

1-(3-Isobutoxy-6-Methyl-Pyridin-2-Ylmethyl)-1H-Indazole-5-Carboxylic Acid, 104

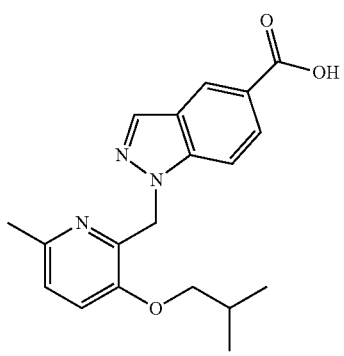 [SMILES: Cc1ccc(OCC(C)C)c(Cn2ncc3cc(C(=O)O)ccc32)n1]

Step 1

(3-Isobutoxy-6-methyl-pyridin-2-yl)-methanol, 101

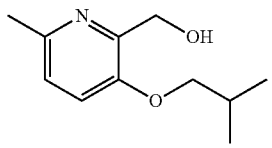

A solution of 3-Hydroxy-2-(hydroxymethyl)-5-methyl-pyridine (1.0 g, 7.19 mmole) in DMF (10 ml) was treated with potassium carbonate (5 g, 35.9 mmole) and 1-iodo-2-methylpropane (1.65 ml, 14.4 mmole). The mixture was stirred at room temperature under a nitrogen atmosphere for 18 h. The mixture was then evaporated to dryness and the residue partitioned between ethyl acetate (50 ml) and water (50 ml). The organic extract was separated then washed with saturated brine then dried over sodium sulphate, filtered and evaporated to dryness. The residue was chromatographed on silica gel eluting with a 1:2 mixture of ethyl acetate/isohexane. This gave the title compound as a pale yellow oil (0.62 g, 45%).

¹H-NMR (CDCl₃, 300 MHz) δ 7.02 (m, 2H, ArH), 4.73 (s, 2H, CH₂OH), 3.73 (d, 2H, —OCH₂—), 2.50 (s, 3H, ArCH₃), 2.10 (m, 1H, CH), 1.03 (d, 6H, 2×CH₃).

Step 2

Methanesulfonic acid 3-isobutoxy-6-methyl-pyridin-2-ylmethyl ester, 102

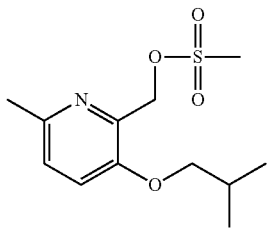 [SMILES: Cc1ccc(OCC(C)C)c(COS(C)(=O)=O)n1]

A solution of (3-Isobutoxy-6-methyl-pyridin-2-yl)-methanol (0.3 g, 1.54 mmole) in dichloromethane (10 ml) was treated with diisopropylethylamine (0.3 ml, 1.69 mmole) and methanesulphonic anhydride (0.3 g, 1.69 mmole) then stirred at ambient temperature under a nitrogen atmosphere for 1.5 h. The mixture was then washed with water (50 ml) and saturated brine (50 ml). The organic layer was dried over sodium sulphate, filtered and evaporated to dryness to give the title compound as a colorless oil.

1H-NMR (CDCl₃, 300 MHz) δ 7.15 (m, 2H, ArH), 5.41 (s, 2H, CH₂O Ms), 3.77 (d, 2H, —OCH₂—), 3.11 (s, 3H, —OSOCH₃), 2.51 (s, 3H, ArCH₃), 2.15 (m, 1H, CH), 1.06 (d, 6H, 2×CH₃).

Step 3

1-(3-Isobutoxy-6-methyl-pyridin-2-ylmethyl)-1H-indazole-5-carboxylic acid methyl ester, 103

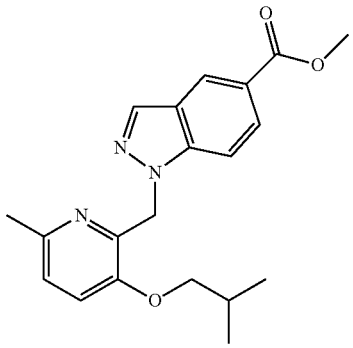

To a solution of Methanesulfonic acid 3-isobutoxy-6-methyl-pyridin-2-ylmethyl ester (1.54 mmole) and 1H-Indazole-5-carboxylic acid methyl ester (0.247 g, 1.4 mmole) in DMF (8 ml) was added cesium carbonate (0.548 g, 1.68 mmole) and the mixture stirred at ambient temperature for 18 h. The mixture was evaporated to dryness and the residue partitioned between water (20 ml) and ethyl acetate (2×20 ml). The combined organics were dried over sodium sulphate, filtered and evaporated to dryness. The residue was chromatographed using silica gel eluting with a 1:2 mixture of ethyl acetate/isohexane to give in the early fractions the title compound (0.240 g, 48%) as a white solid. The corresponding 2-yl-indazole isomer eluted in the later column fractions.

1H-NMR (CDCl₃, 300 MHz) δ 8.49 (s, 1H, ArH), 8.09 (s, 1H, ArH), 8.01 (dd, 1H, ArH), 7.56 (d, 1H, ArH), 7.03 (s, 2H, ArH), 5.73 (s, 2H, CH₂), 3.94 (s, 3H, CH₃), 3.62 (d, 2H, CH₂), 2.49 (s, 3H, CH₃), 1.94 (m, 1H, CH), 0.89 (d, 6H, 2×CH₃). LC-MS: m/z 354 M+H⁺.

Step 4

1-(3-Isobutoxy-6-methyl-pyridin-2-ylmethyl)-1H-indazole-5-carboxylic acid, 104

A solution of 1-(3-Isobutoxy-6-methyl-pyridin-2-ylmethyl)-1H-indazole-5-carboxylic acid methyl ester (0.240 g, 0.68 mmole) in 1,4-dioxane (10 ml) was treated with 2M sodium hydroxide (10 ml) and the mixture stirred at 60° C. for 18 h. The mixture was evaporated to dryness and the residue dissolved in water (20 ml) then acidified to pH1 with 2M hydrochloric acid. The resulting precipitate was extracted into ethyl acetate (2×50 ml). The combined organics were dried over sodium sulphate, filtered and evaporated to dryness. The residue was chromatographed on silica gel eluting a mixture 1:1 of isohexane/ethyl acetate to give the title compound as a white solid (0.2 g, 87%).

1H-NMR (CDCl₃, 300 MHz) δ 8.55 (s, 1H, ArH), 8.13 (s, 1H, ArH), 8.02 (dd, 1H, ArH), 7.59 (d, 1H, ArH), 7.07 (s, 2H, ArH), 5.79 (s, 2H, CH₂), 3.64 (d, 2H, CH₂), 2.49 (s, 3H, CH₃), 1.96 (m, 1H, CH), 0.90 (d, 6H, 2×CH₃). LC-MS m/z 340 M+H⁺

Example 51

1-[5-Bromo-2-(1-Ethyl-Propoxy)-Benzyl]-1H-Indazole-5-Carboxylic Acid, 105

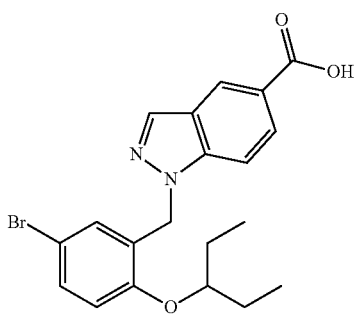 [SMILES: CCC(CC)Oc1ccc(Br)cc1Cn1ncc2cc(C(=O)O)ccc21]

The title compound was prepared following the same method as Example 4.

¹H-NMR (CDCl₃, 300 MHz) δ 8.55 (s, 1H, ArH), 8.20 (s, 1H, ArH), 8.10 (d, 1H, ArH), 7.50 (d, 1H, ArH), 7.30 (m, 1H, ArH), 7.10 (s, 1H, ArH), 6.75 (d, 1H, ArH), 5.55 (s, 2H, ArCH₂Het), 4.15 (m, 1H, —CHO—), 1.60 (q, 4H, CH₂), 0.80 (d, 6H, —CH₃).

LC-MS: m/z 418 M+H⁺.

Example 52

1-[5-Bromo-2-(2,2-Dimethyl-Propoxy)-Benzyl]-1H-Indazole-5-Carboxylic Acid, 106

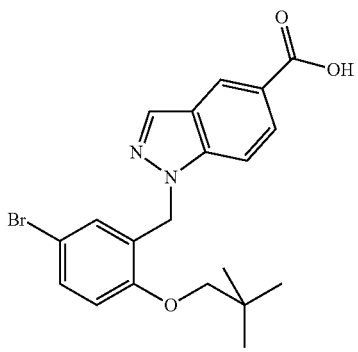 [SMILES: CC(C)(C)COc1ccc(Br)cc1Cn1ncc2cc(C(=O)O)ccc21]

The title compound was prepared following the same method as Example 4.

¹H-NMR (CDCl₃, 300 MHz) δ 8.57 (s, 1H, ArH), 8.20 (s, 1H, ArH), 8.10 (d, 1H, ArH), 7.40 (d, 1H, ArH), 7.33 (m, 1H, ArH), 6.87 (s, 1H, ArH), 6.80 (d, 1H, ArH), 5.65 (s, 2H, ArCH₂Het), 3.68 (s, 2H, CH₂), 1.05 (s, 9H, 3×CH₃). LC-MS: m/z 418 M+H⁺.

Example 53

1-[5-Bromo-2-(2-Hydroxy-2-Methyl-Propoxy)-Benzyl]-1H-Indazole-5-Carboxylic Acid, 108

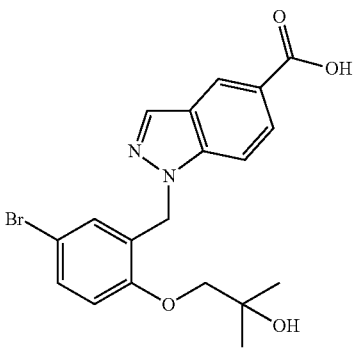

Step 1

1-[5-Bromo-2-(2-hydroxy-2-methyl-propoxy)-benzyl]-1H-indazole-5-carboxylic acid methyl ester, 107

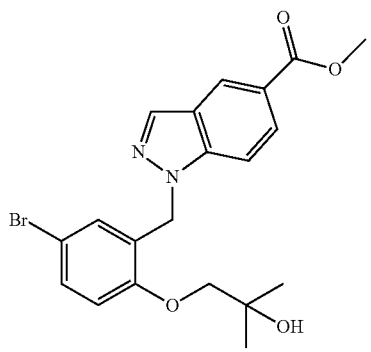 [SMILES: COC(=O)c1ccc2c(cnn2Cc2cc(Br)ccc2OCC(C)(C)O)c1]

A mixture of compound 12 (0.037 g, 0.1 mmole), 1.2-epoxy-2-methylpropane (0.1 mL, 1.1 mmol) and tetrabutylammonium fluoride 1M (0.1 mL, 0.1 mmol) in THF (3 ml) was treated under microwave conditions at 120° C. for 20 min. Then methyl iodide (0.1 mL) and N-methylmorpholine (0.1 mL) were added to the solution and the mixture was treated under microwave conditions at 120° C. for 10 minutes.

The mixture was diluted with methanol and ethyl acetate. Washed with water and Brine. The organic extract was separated then dried over sodium sulphate, filtered and evaporated to dryness. The residue was chromatographed on silica gel eluting with a gradient from 1:4 to 2:3 mixture of ethyl acetate/isohexane. This gave the title compound as a pale yellow oil (0.03 g, 70%).

$^1$H-NMR (CDCl$_3$, 300 MHz) δ 8.55 (s, 1H, ArH), 8.15 (s, 1H, ArH), 8.10 (m, 1H, ArH), 7.55 (d, 1H, ArH), 7.40 (m, 2H, ArH), 6.75 (d, 1H, ArH), 5.55 (s, 2H, ArCH$_2$Het), 3.97 (s, 3H, CH$_3$), 3.80 (s, 2H, —CH$_2$O—), 1.40 (s, 6H, —CH$_3$).

Step 2

1-[5-bromo-2-(2-hydroxy-2-methyl-propoxy)-benzyl]-1h-indazole-5-carboxylic acid, 108

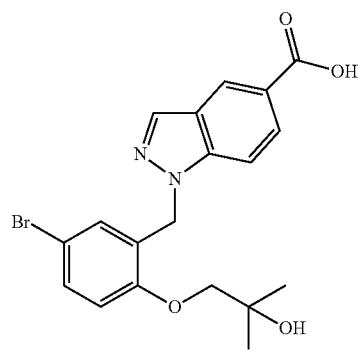 [SMILES: CC(C)(O)COc1ccc(Br)cc1Cn1ncc2cc(C(=O)O)ccc21]

A solution of 1-[5-Bromo-2-(2-hydroxy-2-methyl-propoxy)-benzyl]-1H-indazole-5-carboxylic acid methyl ester (0.03 g, 0.7 mmole) in a mixture of THF (5 ml), methanol (5 mL) and water (1 mL) was treated with lithium hydroxide (0.1 g, 2.4 mmole) then stirred at ambient temperature under a nitrogen atmosphere for 20 h. The mixture was diluted with more water and extracted with isohexane. The aqueous layer was acidified with a 2M HCl solution and extracted with ethyl acetate. The organic layer was washed with saturated brine (50 ml). The organic layer was dried over sodium sulphate, filtered and evaporated to dryness to give the title compound as a colorless oil.

$^1$H-NMR (CDCl$_3$, 300 MHz) δ 8.55 (s, 1H, ArH), 8.15 (s, 1H, ArH), 8.10 (m, 1H, ArH), 7.55 (d, 1H, ArH), 7.40 (m, 2H, ArH), 6.75 (d, 1H, ArH), 5.55 (s, 2H, ArCH$_2$Het), 3.80 (s, 2H, —CH$_2$O—), 1.40 (s, 6H, —CH$_3$). LC-MS: m/z 420 M+H$^+$.

Example 54

1-(5-Hydroxy-2-Isobutoxy-Benzyl)-1H-Indazole-5-Carboxylic Acid, 114

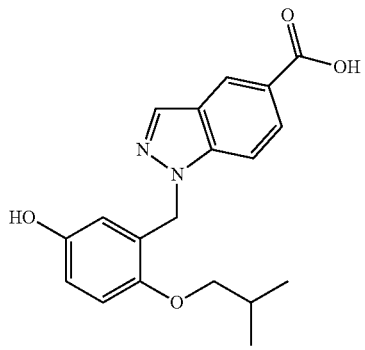 [SMILES: CC(C)COc1ccc(O)cc1Cn1ncc2cc(C(=O)O)ccc21]

Step 1

5-(tert-Butyl-dimethyl-silanyloxy)-2-hydroxy-benzoic acid methyl ester, 109

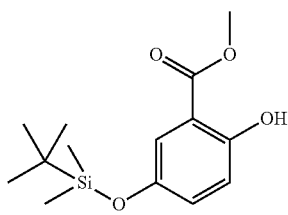 [SMILES: COC(=O)c1cc(O[Si](C)(C)C(C)(C)C)ccc1O]

To a solution of methyl-2,5-dihydroxybenzoate (7.0 g, 41.7 mmole) and imidazole (4.24 g, 62.4 mmole), at 0° C. and under nitrogen, in DCM (300 mL) was added a solution of tert-butyldimethylsilyl chloride (6.6 g, 43.8 mmole) in DCM (60 mL) drop wise over 30 minutes. After 3 h, the ice-bath was removed and the mixture was stirred at room temperature for 16 h. Then the mixture was washed with 2M HCl solution and saturated brine then dried over sodium sulphate, filtered and evaporated to dryness. This gave the title compound as colorless oil (11.1 g, 95%).

1H-NMR (CDCl$_3$, 300 MHz) δ 10.3 (s, 1H, ArOH), 7.25 (m, 1H, ArH), 7.00 (m, 1H, ArH), 6.85 (m, 1H, ArH), 3.95 (s, 3H, —OCH$_3$), 1.00 (s, 9H, SiC(CH$_3$)$_3$), 0.2 (s, 6H, 2×SiCH$_3$).

Step 2

5-(tert-Butyl-dimethyl-silanyloxy)-2-isobutoxy-benzoic acid methyl ester, 110

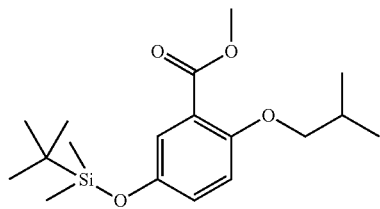 [SMILES: COC(=O)c1cc(O[Si](C)(C)C(C)(C)C)ccc1OCC(C)C]

A solution of 5-(tert-Butyl-dimethyl-silanyloxy)-2-hydroxy-benzoic acid methyl ester (5 g, 17.7 mmole) in anhydrous THF (150 ml) was treated with 2-methyl-1-propanol (1.8 ml, 19.5 mmole), triphenylphosphine (5.1 g, 19.5 mmole) and DIAD (3.8 mL, 19.5 mmole) then stirred at 0° C. for 2 h, at room temperature for 1 h and at reflux for 24 h. The mixture was then evaporated to dryness and the residue was purified by column chromatography using 95:5 mixture of isohexane/ethyl acetate to give the title compound as a colorless oil. (1.8 g, 30%).

1H-NMR (CDCl$_3$, 300 MHz) δ 7.25 (m, 1H, ArH), 7.00 (m, 1H, ArH), 6.85 (m, 1H, ArH), 3.85 (s, 3H, —OCH$_3$), 3.75 (d, 2H, OCH$_2$—), 2.10 (m, 1H, CH), 1.05 (d, 6H, 2×CH$_3$), 1.00 (s, 9H, SiC(CH$_3$)$_3$), 0.2 (s, 6H, 2×SiCH$_3$).

Step 3

[5-(tert-Butyl-dimethyl-silanyloxy)-2-isobutoxyphenyl]-methanol, 111

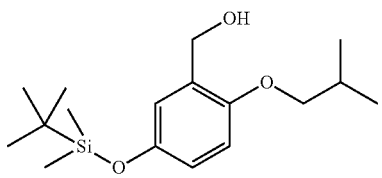 [SMILES: CC(C)COc1ccc(O[Si](C)(C)C(C)(C)C)cc1CO]

To a solution 5-(tert-Butyl-dimethyl-silanyloxy)-2-isobutoxy-benzoic acid methyl ester (1.8 g, 5.32 mmole) in anhydrous toluene (50 ml) was added a 1M solution in toluene of DIBAL (21 mL, 21 mmole) and the mixture stirred under nitrogen atmosphere at ambient temperature for 2 h. Then a 10% Rochelle's salt solution was added and the mixture stirred for 30 min more. 2M HCl solution (20 mL) was added and the mixture was extracted with ethyl acetate. The combined organics were dried over sodium sulphate, filtered and evaporated to dryness. The residue was chromatographed using silica gel eluting with a 1:2 mixture of ethyl acetate/isohexane to give in the early fractions the title compound (0.91 g, 55%) as a colorless oil.

1H-NMR (CDCl$_3$, 300 MHz) δ 6.75 (s, 1H, ArH), 6.55 (s, 2H, ArH), 4.52 (d, 2H, —CH$_2$OH), 3.62 (d, 2H, OCH$_2$—), 2.10 (m, 1H, CH), 1.05 (d, 6H, 2×CH$_3$), 1.00 (s, 9H, SiC(CH$_3$)$_3$), 0.2 (s, 6H, 2×SiCH$_3$). LC-MS: m/z 293 [M+H$_2$O]$^+$.

Step 4

1-[5-(tert-Butyl-dimethyl-silanyloxy)-2-isobutoxybenzyl]-1H-indazole-5-carboxylic acid methyl ester, 112

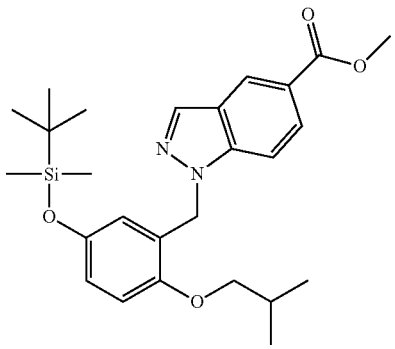

A solution of 1H-indazole-5-carboxylic acid methyl ester, 4, (0.6 g, 3.5 mmole), triphenylphosphine (1.2 g, 4.4 mmole), [5-(tert-Butyl-dimethyl-silanyloxy)-2-isobutoxyphenyl]-methanol (0.9 g, 2.9 mmole) and di-isopropylazodicarboxylate (0.9 mL, 4.4 mmol) in anhydruous THF (50 mL) was heated at reflux for 16 h. Then the volatiles were removed in vacuo and the crude product was purified on silica using a gradient from 95:5 to 90:10 isohexane/ethyl acetate. This gave the title compound as colorless oil (0.3 g, 20%).

1H-NMR (CDCl₃, 300 MHz) δ 8.55 (s, 1H, ArH), 8.15 (s, 1H, ArH), 8.00 (d, 1H, ArH), 7.40 (d, 1H, ArH), 6.70 (m, 2H, ArH), 6.25 (s, 1H, ArH), 5.52 (s, 2H, —CH₂Het), 3.95 (s, 3H, OCH₃), 3.72 (d, 2H, OCH₂—), 2.10 (m, 1H, CH), 1.05 (d, 6H, 2×CH₃), 0.85 (s, 9H, SiC(CH₃)₃), 0.05 (s, 6H, 2×SiCH₃).

Step 5

1-(5-Hydroxy-2-isobutoxy-benzyl)-1H-indazole-5-carboxylic acid methyl ester, 113

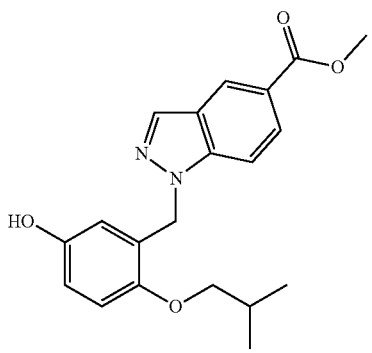 [SMILES: COC(=O)c1ccc2c(cnn2Cc2cc(O)ccc2OCC(C)C)c1]

A solution of 1-[5-(tert-Butyl-dimethyl-silanyloxy)-2-isobutoxy-benzyl]-1H-indazole-5-carboxylic acid methyl ester (0.3 g, 0.64 mmole) in anhydruous THF (10 mL) was treated with a 1M TBAF solution in THF (1 mL, 1 mmole) and the mixture was stirred at room temperature for 1 h. Then the volatiles were removed in vacuo and the crude product was purified on silica using a gradient from 4:1 to 3:1 isohexane/ethyl acetate. This gave the title compound as colorless oil (0.135 g, 60%).

1H-NMR (CDCl₃, 300 MHz) δ 8.50 (s, 1H, ArH), 8.02 (d, 1H, ArH), 7.90 (s, 1H, ArH), 7.40 (d, 1H, ArH), 6.70 (m, 2H, ArH), 6.20 (s, 1H, ArH), 6.10 (s, 1H, ArOH), 5.60 (s, 2H, —CH₂Het), 3.97 (s, 3H, OCH₃), 3.75 (d, 2H, OCH₂—), 2.10 (m, 1H, CH), 1.05 (d, 6H, 2×CH₃).

Step 6

1-(5-Hydroxy-2-isobutoxy-benzyl)-1H-indazole-5-carboxylic acid, 114

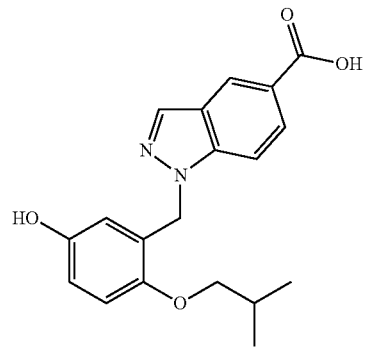 [SMILES: CC(C)COc1ccc(O)cc1Cn1ncc2cc(C(=O)O)ccc21]

A solution of 11-(5-Hydroxy-2-isobutoxy-benzyl)-1H-indazole-5-carboxylic acid methyl ester (0.03 g, 0.08 mmole) in a mixture of THF (2 ml), methanol (1 mL) and water (1 mL) was treated with lithium hydroxide (0.09 g, 2.14 mmole) then stirred under microwave conditions at 120° C. for 5 min. The mixture was diluted with more water and extracted with isohexane. The aqueous layer was acidified with a 2M HCl solution and extracted with ethyl acetate. The organic layer was washed with saturated brine (50 ml). The organic layer was dried over sodium sulphate, filtered and evaporated to dryness to give the crude residue that was purified by column in silica using 1:1 mixture ethyl acetate/isohexane as eluent to give the title compound as a colorless oil. (12.3 mg, 50%).

1H-NMR (MeOD, 300 MHz) δ 8.55 (s, 1H, ArH), 8.20 (s, 1H, ArH), 8.12 (d, 1H, ArH), 7.55 (d, 1H, ArH), 6.80 (m, 1H, ArH), 6.75 (m, 1H, ArH), 6.25 (s, 1H, ArH), 5.60 (s, 2H, —CH₂Het), 3.70 (d, 2H, OCH₂—), 2.10 (m, 1H, CH), 1.00 (d, 6H, 2×CH₃). LC-MS: m/z 341 M+H⁺.

Example 55

1-[5-(2,2-Difluoro-Ethoxy)-2-Isobutoxy-Benzyl]-1H-Indazole-5-Carboxylic Acid, 116

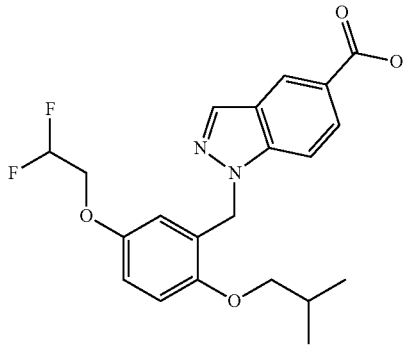 [SMILES: CC(C)COc1ccc(OCC(F)F)cc1Cn1ncc2cc(C(=O)O)ccc21]

Step 1

1-[5-(2,2-Difluoro-ethoxy)-2-isobutoxy-benzyl]-1H-indazole-5-carboxylic acid methyl ester, 115

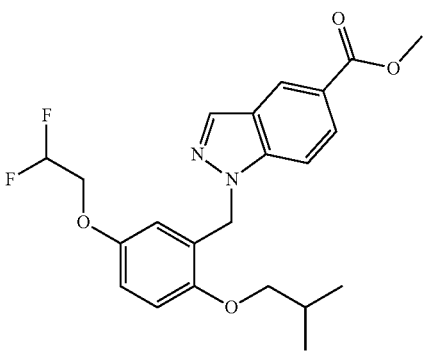 [SMILES: COC(=O)c1ccc2c(cnn2Cc2cc(OCC(F)F)ccc2OCC(C)C)c1]

A solution of compound 104 (0.03 g, 0.08 mmole) in a mixture of anhydrous THF (2 ml) and anhydrous toluene (1 mL) was treated with 2,2-difluoroethanol (0.04 ml, 0.27 mmole), triphenylphosphine (0.07 g, 0.27 mmole) and DTAD (0.055 g, 0.27 mmole) then stirred under microwave conditions at 140° C. for 20 min. The mixture was then evaporated to dryness and the residue was purified by column chromatography using a gradient from 90:10 to 80:20 mixture of isohexane/ethyl acetate to give the title compound as a colorless oil. (0.02 g, 60%).

1H-NMR (CDCl$_3$, 300 MHz) δ 8.55 (s, 1H, ArH), 8.15 (s, 1H, ArH), 8.02 (d, 1H, ArH), 7.45 (d, 1H, ArH), 6.75 (m, 2H, ArH), 6.45 (s, 1H, ArH), 5.97 (tt, 1H, F$_2$CH), 5.65 (s, 2H, —CH$_2$Het), 4.00 (m, 2H, CH$_2$CHF$_2$), 3.95 (s, 3H, OCH$_3$), 3.75 (d, 2H, OCH$_2$—), 2.10 (m, 1H, CH), 1.05 (d, 6H, 2×CH$_3$).

Step 2

1-[5-(2,2-Difluoro-ethoxy)-2-isobutoxy-benzyl]-1H-indazole-5-carboxylic acid, 116

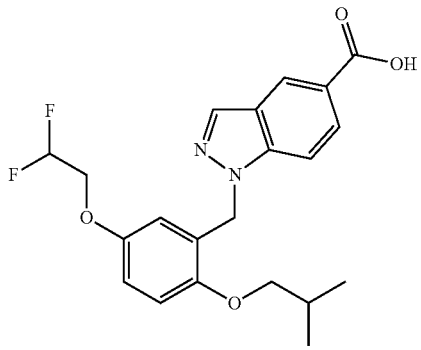 [SMILES: CC(C)COc1ccc(OCC(F)F)cc1Cn1ncc2cc(C(=O)O)ccc21]

A solution of 1-[5-(2,2-Difluoro-ethoxy)-2-isobutoxy-benzyl]-1H-indazole-5-carboxylic acid methyl ester (0.02 g, 0.05 mmole) in a mixture of THF (3 ml), methanol (4 mL) and water (1 mL) was treated with lithium hydroxide (0.1 g, 2.4 mmole) then stirred at room temperature for 16 h. The mixture was diluted with more water and extracted with isohexane. The aqueous layer was acidified with a 2M HCl solution and extracted with ethyl acetate. The organic layer was washed with saturated brine (50 ml). The organic layer was dried over sodium sulphate, filtered and evaporated to dryness to give the title compound as a colorless oil. (19.2 mg, 95%).

1H-NMR (CDCl$_3$, 300 MHz) δ 8.60 (s, 1H, ArH), 8.17 (s, 1H, ArH), 8.05 (d, 1H, ArH), 7.45 (d, 1H, ArH), 6.77 (m, 2H, ArH), 6.50 (s, 1H, ArH), 5.97 (tt, 1H, F$_2$CH), 5.65 (s, 2H, —CH$_2$Het), 4.00 (td, 2H, CH$_2$CHF$_2$), 3.75 (d, 2H, OCH$_2$—), 2.10 (m, 1H, CH), 1.05 (d, 6H, 2×CH$_3$). LC-MS: m/z 405 M+H$^+$

Example 56

1-(5-Difluoromethoxy-2-Isobutoxy-Benzyl)-1H-Indazole-5-Carboxylic Acid, 118

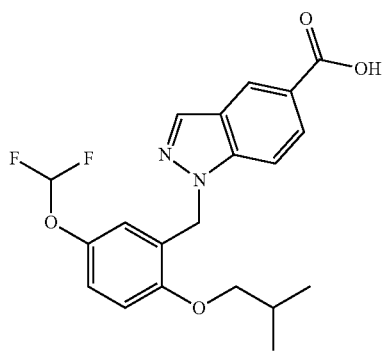 [SMILES: CC(C)COc1ccc(OC(F)F)cc1Cn1ncc2cc(C(=O)O)ccc21]

Step 1

1-(5-Difluoromethoxy-2-isobutoxy-benzyl)-1H-indazole-5-carboxylic acid methyl ester, 117

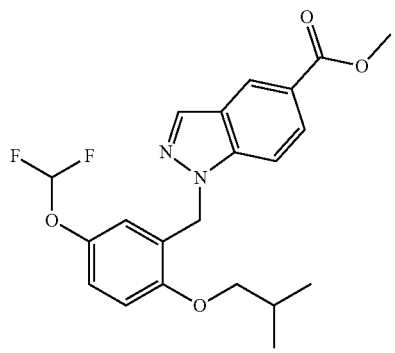 [SMILES: COC(=O)c1ccc2c(cnn2Cc2cc(OC(F)F)ccc2OCC(C)C)c1]

To a solution of compound 104 (0.07 g, 0.2 mmole) in acetonitrile (1.5 ml) was added an aqueous solution of KOH in water (4 mmole in 1.5 mL). Nitrogen was bubbled through the mixture for 5 min. and then cold down to −78° C. under nitrogen atmosphere. Then the mixture was treated with a solution of diethyl(bromodifluoromethyl)phosphonate (0.074 ml, 0.4 mmole) in acetonitrile (0.3 mL), allowed to warm to room temperature slowly (20 min) and stirred for 1.5 h. Then, the same process was repeated again but this time the reaction was stirred overnight.

To the reaction mixture was added ethyl acetate and 2M HCl solution. The organic layer was separated, washed with Brine, dried and then evaporated to dryness. The residue was purified by column chromatography using a gradient from 100:0 to 90:10 mixture of isohexane/ethyl acetate to give the title compound as a colorless oil. (0.014 g, 17%).

1H-NMR (CDCl$_3$, 300 MHz) δ 8.65 (s, 1H, ArH), 8.20 (s, 1H, ArH), 8.08 (d, 1H, ArH), 7.45 (d, 1H, ArH), 7.00 (m, 1H, ArH), 6.85 (d, 1H, ArH), 6.55 (s, 1H, ArH), 6.3 (t, 1H, F$_2$CH), 5.65 (s, 2H, —CH$_2$Het), 3.95 (s, 3H, OCH$_3$), 3.78 (d, 2H, OCH$_2$—), 2.10 (m, 1H, CH), 1.05 (d, 6H, 2×CH$_3$).

Step 2

1-(5-Difluoromethoxy-2-isobutoxy-benzyl)-1H-indazole-5-carboxylic acid, 118

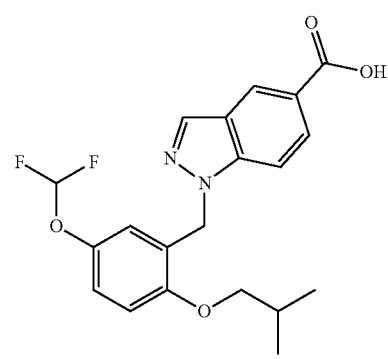 [SMILES: CC(C)COc1ccc(OC(F)F)cc1Cn1ncc2cc(C(=O)O)ccc21]

A solution of 1-(5-Difluoromethoxy-2-isobutoxy-benzyl)-1H-indazole-5-carboxylic acid methyl ester (0.014 g, 0.035 mmole) in a mixture of THF (1 ml), methanol (1 mL) and water (1 mL) was treated with lithium hydroxide (0.05 g, 1.2 mmole) then stirred at room temperature for 16 h. The mixture was diluted with more water and extracted with isohexane. The aqueous layer was acidified with a 2M HCl solution and extracted with ethyl acetate. The organic layer was washed with saturated brine (50 ml). The organic layer was dried over sodium sulphate, filtered and evaporated to dryness to give the title compound as a colorless oil. (8.7 mg, 63%).

1H-NMR (CDCl$_3$, 300 MHz) δ 8.65 (s, 1H, ArH), 8.20 (s, 1H, ArH), 8.08 (d, 1H, ArH), 7.45 (d, 1H, ArH), 7.00 (m, 1H, ArH), 6.85 (d, 1H, ArH), 6.55 (s, 1H, ArH), 6.3 (t, 1H, F$_2$CH), 5.65 (s, 2H, —CH$_2$Het), 3.78 (d, 2H, OCH$_2$—), 2.10 (m, 1H, CH), 1.05 (d, 6H, 2×CH$_3$). LC-MS: m/z 391 M+H$^+$.

Example 57

1-(5-Chloro-2-Isobutoxy-Benzyl)-1H-Pyrazolo[3,4-b]Pyridine-5-Carboxylic Acid, 119

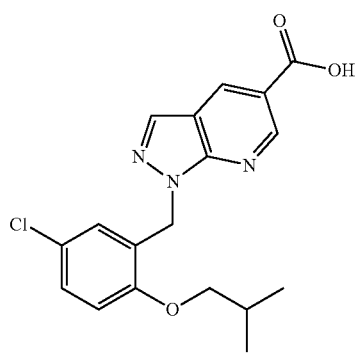 [SMILES: CC(C)COc1ccc(Cl)cc1Cn1ncc2cc(C(=O)O)cnc21]

The title compound was prepared following the same method as Example 30.

$^1$H-NMR (CDCl$_3$, 300 MHz) δ 9.25 (s, 1H, ArH), 8.80 (s, 1H, ArH), 8.20 (s, 1H, ArH), 7.33 (m, 2H, ArH), 6.74 (d, 1H, ArH), 5.65 (s, 2H, ArCH$_2$), 3.75 (d, 2H, OCH$_2$). 2.01 (m, 1H, CH), 0.96 (d, 6H, CH$_3$). LC-MS: m/z 360 M+H$^+$.

Example 58

1-(2-Isobutoxy-5-Trifluoromethoxy-Benzyl)-1H-Pyrazolo[3,4-b]Pyridine-5-Carboxylic Acid, 120

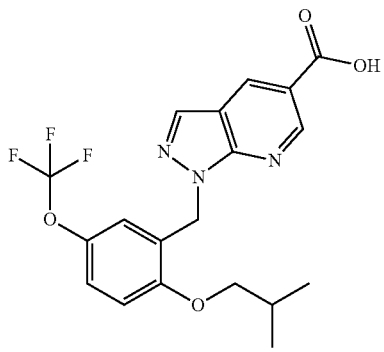 [SMILES: CC(C)COc1ccc(OC(F)(F)F)cc1Cn1ncc2cc(C(=O)O)cnc21]

The title compound was prepared following the same method as Example 30.

$^1$H-NMR (CDCl$_3$, 300 MHz) δ 9.25 (s, 1H, ArH), 8.70 (s, 1H, ArH), 8.00 (s, 1H, ArH), 7.05 (m, 1H, ArH), 6.75 (d, 1H, ArH), 6.65 (s, 1H, ArH), 5.65 (s, 2H, ArCH$_2$), 3.65 (d, 2H, OCH$_2$). 2.01 (m, 1H, CH), 0.96 (d, 6H, CH$_3$). LC-MS: m/z 410 M+H$^+$.

Example 59

1-[5-Bromo-2-(2-Ethyl-Butoxy)-Benzyl]-3-Methyl-1H-Pyrazolo[3,4-b]Pyridine-5-Carboxylic Acid, 121

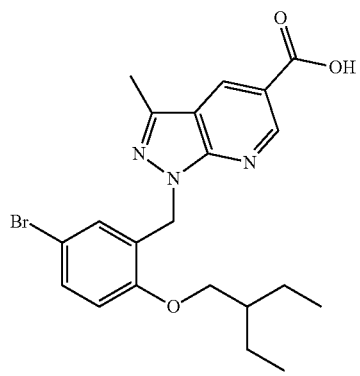

The title compound was prepared following the same method as Example 30.

$^1$H-NMR (CDCl$_3$, 300 MHz) δ 9.22 (s, 1H, ArH), 8.80 (s, 1H, ArH), 7.32 (s, 1H, ArH), 6.85 (m, 1H, ArH), 6.75 (d, 1H, ArH), 5.70 (s, 2H, ArCH$_2$), 3.88 (d, 2H, OCH$_2$). 2.65 (s, 3H, ArCH$_3$), 2.01 (m, 1H, CH), 1.45 (q, 4H, 2×CH$_2$), 0.96 (t, 6H, 2×CH$_3$).

LC-MS: m/z 448 M+H$^+$.

Example 60

1-[5-Chloro-2-(2-Ethyl-Butoxy)-Benzyl]-3-Methyl-1H-Pyrazolo[3,4-b]Pyridine-5-Carboxylic Acid, 122

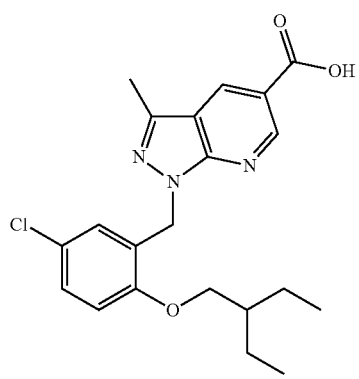 [SMILES: CCC(CC)COc1ccc(Cl)cc1Cn1nc(C)c2cc(C(=O)O)cnc21]

The title compound was prepared following the same method as Example 30.

$^1$H-NMR (CDCl$_3$, 300 MHz) δ 9.22 (s, 1H, ArH), 8.80 (s, 1H, ArH), 7.15 (m, 1H, ArH), 6.80 (d, 1H, ArH), 6.70 (d, 1H, ArH), 5.65 (s, 2H, ArCH$_2$), 3.88 (d, 2H, OCH$_2$). 2.65 (s, 3H, ArCH$_3$), 2.01 (m, 1H, CH), 1.45 (q, 4H, 2×CH$_2$), 0.96 (t, 6H, 2×CH$_3$).

LC-MS: m/z 402 M+H$^+$.

Example 61

1-(5-Chloro-2-Isobutoxy-Benzyl)-3-Methyl-1H-Pyrazolo[3,4-b]Pyridine-5-Carboxylic Acid, 123

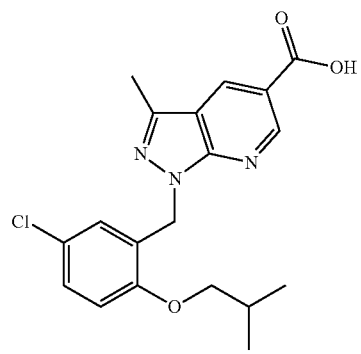 [SMILES: Cc1nn(Cc2cc(Cl)ccc2OCC(C)C)c2ncc(C(=O)O)cc12]

The title compound was prepared following the same method as Example 30.

$^1$H-NMR (CDCl$_3$, 300 MHz) δ 9.25 (s, 1H, ArH), 8.70 (s, 1H, ArH), 7.15 (d, 1H, ArH), 6.75 (d, 1H, ArH), 6.15 (d, 1H, ArH), 5.65 (s, 2H, ArCH$_2$), 3.70 (d, 2H, OCH$_2$). 2.65 (s, 3H, ArCH$_3$), 2.01 (m, 1H, CH), 0.90 (d, 6H, 2×CH$_3$).

LC-MS: m/z 374 M+H$^+$

Example 62

1-[5-Chloro-2-(2-Ethyl-Butoxy)-Benzyl]-1H-Pyrazolo[3,4-c]Pyridine-5-Carboxylic Acid Amide, 129

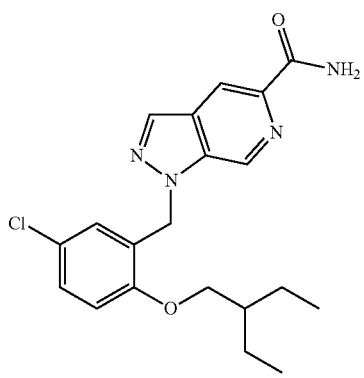 [SMILES: CCC(CC)COc1ccc(Cl)cc1Cn1ncc2cc(C(N)=O)ncc21]

Step 1

1H-Pyrazolo[3,4-c]pyridine-5-carbonitrile, 124

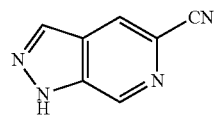

A mixture of 5-Bromo-1,4-pyrazolo[3,4,c]pyridine (0.15 g, 0.76 mmole), Zn(CN)$_2$ (0.092 g, 0.76 mmole) and Pd(PPh$_3$)$_4$ (0.026 g, 0.02 mmole) in DMF (2 ml) heated at 180° C. in a microwave reactor under a N$_2$ atmosphere for 30 min. The mixture was partitioned between water and EtOAc. The organic layer was washed with brine, dried (MgSO$_4$) and evaporated to dryness to give the title compound as a brown solid.

1H-NMR (MeOD, 300 MHz) δ 8.35 (s, 1H, ArH), 7.38 (s, 1H, ArH), 7.28 (s, 1H, ArH).

Step 2

5-chloro-2-(2-ethyl-butoxy)-benzaldehyde, 125

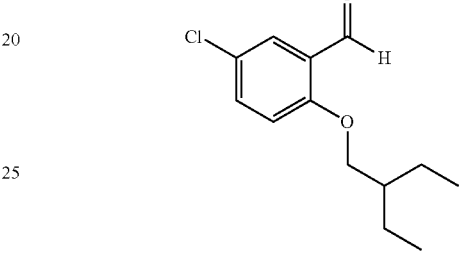

A solution of 5-chloroalicaldehyde (2.0 g, 12.8 mmole) in DMF (50 ml) was treated with potassium carbonate (3 g, 22 mmole) and tetrabutylammonium iodide (0.22 g) and 3-chloromethylpentane (1.65 ml, 12.2 mmole). The mixture was stirred at 110° C. under a nitrogen atmosphere for 18 h. The mixture was then evaporated to dryness and the residue partitioned between ethyl acetate (50 ml) and water (50 ml). The organic extract was separated then washed with saturated brine then dried over sodium sulphate, filtered and evaporated to dryness. The residue was chromatographed on silica gel eluting with a gradient of 5-15% ethyl acetate/isohexane. This gave the title compound as a pale yellow oil (2.97 g, 78%).

$^1$H-NMR (CDCl$_3$, 300 MHz) δ10.49 (s, 1H, CHO), 7.95 (d, 1H, ArH), 7.63 (dd, 1H, ArH), 6.90 (d, 1H, ArH), 4.00 (d, 2H, CH$_2$), 1.80 (m, 1H, CH), 1.55 (s, 4H, 2×CH$_2$—CH$_3$), 1.00 (q, 6H, 2×CH$_2$—CH$_3$).

Step 3

[5-Chloro-2-(2-ethyl-butoxy)-phenyl]methanol, 126

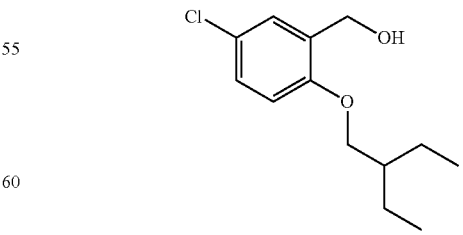

The title compound was prepared following the method in Example 20, Step 2.

$^1$H-NMR (CDCl$_3$, 300 MHz) δ7.45 (d, 1H, ArH), 7.37 (dd, 1H, ArH), 6.80 (d, 1H, ArH), 4.70 (d, 2H, —CH$_2$OH), 3.90 (d, 2H, CH$_2$), 1.80 (m, 1H, CH), 1.55 (s, 4H, 2×CH$_2$—CH$_3$), 1.00 (q, 6H, 2×CH$_2$—CH$_3$).

Step 4

Methanesulfonic acid 5-chloro-2-(2-ethyl-butoxy)-benzyl ester, 127

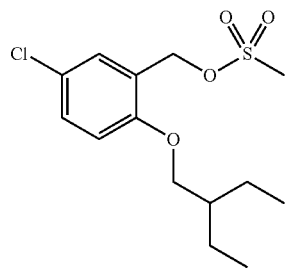 [SMILES: CCC(CC)COc1ccc(Cl)cc1COS(C)(=O)=O]

The title compound was prepared following the method in Example 20, Step 3.

$^1$H-NMR (CDCl$_3$, 300 MHz) δ7.55 (d, 1H, ArH), 7.45 (dd, 1H, ArH), 6.80 (d, 1H, ArH), 5.75 (d, 2H, —CH$_2$OSO$_2$CH$_3$), 3.90 (d, 2H, CH$_2$), 3.00 (s, 3H, CH$_2$OSO$_2$CH$_3$), 1.80 (m, 1H, CH), 1.55 (s, 4H, 2×CH$_2$—CH$_3$), 1.00 (q, 6H, 2×CH$_2$—CH$_3$).

Step 5

1-[5-Chloro-2-(2-ethyl-butoxy)-benzyl]-1H-pyrazolo[3,4-c]pyridine-5-carbonitrile, 128

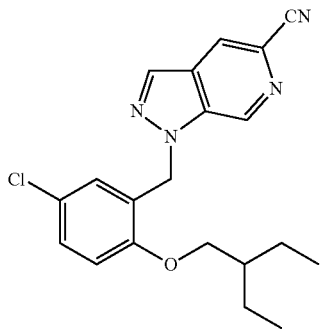 [SMILES: CCC(CC)COc1ccc(Cl)cc1Cn1ncc2cc(C#N)ncc21]

The title compound was prepared following the method in Example 21, Step 4.

$^1$H-NMR (CDCl$_3$, 300 MHz) δ 8.95 (s, 1H, ArH), 8.20 (s, 1H, ArH), 8.10 (s, 1H, ArH), 7.25 (m, 1H, ArH), 7.05 (s, 1H, ArH), 6.85 (s, 1H, ArH), 5.65 (s, 2H, ArCH$_2$), 3.85 (d, 2H, CH$_2$). 1.65 (m, 1H, CH), 1.35 (q, 4H, 2×CH$_2$), 0.85 (t, 6H, 2×CH$_3$).

LC-MS: m/z 369 M+H$^+$

Step 6

1-[5-Chloro-2-(2-ethyl-butoxy)-benzyl]-1H-pyrazolo[3,4-c]pyridine-5-carboxylic acid amide, 129

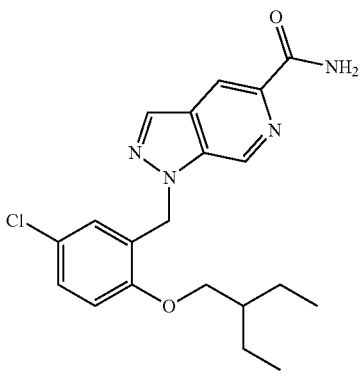 [SMILES: CCC(CC)COc1ccc(Cl)cc1Cn1ncc2cc(C(N)=O)ncc21]

A mixture of 1-[5-Chloro-2-(2-ethyl-butoxy)-benzyl]-1H-pyrazolo[3,4-c]pyridine-5-carbonitrile (0.048 g, 0.13 mmole), 5M aqueous solution of KOH (1 mL), PEG-400 (0.5 mL) and dioxane (0.5 mL) was heated at 180° C. under microwave conditions for 30 min. The mixture was diluted with ethyl acetate (6 mL) and 2M HCl solution (6 mL) and the reaction mixture was extracted. The organic layer was separated, washed with Brine, dried (MgSO$_4$), filtered and the solvent evaporated under vacuum. The residue was purified in silica using 3:2 mixture of isohexane/ethyl acetate to give the title compound as a colorless oil. (0.024 mg, 48%).

$^1$H-NMR (CDCl$_3$, 300 MHz) δ 9.12 (s, 1H, ArH), 8.50 (s, 1H, ArH), 8.07 (s, 1H, ArH), 7.30 (m, 1H, ArH), 7.22 (s, 1H, ArH), 6.85 (d, 1H, ArH), 5.75 (s, 2H, ArCH$_2$), 3.80 (d, 2H, CH$_2$). 1.50 (m, 1H, CH), 1.25 (q, 4H, 2×CH$_2$), 0.80 (t, 6H, 2×CH$_3$).

LC-MS: m/z 387 M+H$^+$

Example 63

1-[5-Chloro-2-(2-Ethyl-Butoxy)-Benzyl]-1H-Pyrazolo[3,4-c]Pyridine-5-Carboxylic Acid, 130

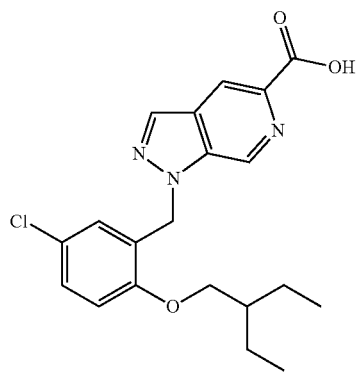 [SMILES: CCC(CC)COc1ccc(Cl)cc1Cn1ncc2cc(C(=O)O)ncc21]

A mixture of 1-[5-chloro-2-(2-ethyl-butoxy)-benzyl]-1h-pyrazolo[3,4-c]pyridine-5-carboxylic acid amide (0.019 g, 0.05 mmole), concentrated solution of HCl (1 mL) and dioxane (0.5 mL) was heated at 150° C. under microwave conditions for 30 min. The mixture was diluted with ethyl acetate (6 mL) and 2M HCl solution (6 mL) and the reaction mixture was extracted. The aqueous phase was basified to PH 5-6 with 2M solution of NaOH and extracted again with ethyl acetate. The combined organic layers were washed with Brine, dried (MgSO$_4$), filtered and the solvent evaporated under vacuum. The residue was purified in a RP-HPLC to give the title compound as a colorless oil. (0.01 mg, 58%).

$^1$H-NMR (MeOD, 300 MHz) δ 9.05 (s, 1H, ArH), 8.52 (s, 1H, ArH), 8.30 (s, 1H, ArH), 7.30 (m, 1H, ArH), 7.25 (s, 1H, ArH), 6.95 (d, 1H, ArH), 5.65 (s, 2H, ArCH$_2$), 3.85 (d, 2H, CH$_2$). 1.52 (m, 1H, CH), 1.35 (q, 4H, 2×CH$_2$), 0.85 (t, 6H, 2×CH$_3$).

LC-MS: m/z 388 M+H$^+$

Example 64

1-(5-Bromo-2-Isobutoxy-Benzyl)-3-Ethyl-1H-Indazole-5-Carboxylic Acid, 134

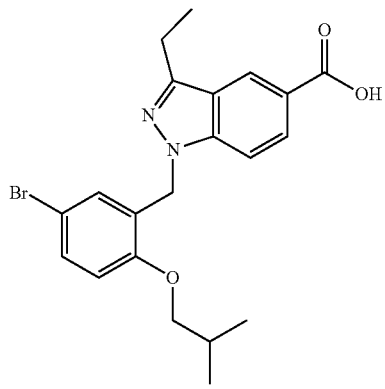 [SMILES: CCc1nn(Cc2cc(Br)ccc2OCC(C)C)c2ccc(C(=O)O)cc12]

Step 1

3-Vinyl-1H-indazole-5-carboxylic acid methyl ester, 131

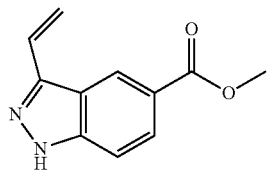

3-Iodo-1H-indazole-5-carboxylic acid methyl ester (0.5 g, 1.65 mmole) in dimethoxyethane (12.5 ml) was placed in a microwave vial and treated with sodium carbonate (0.55 g, 5.1 mmole), tetrakis(triphenylphosphine)palladium(0) (0.09 g, 5 mol %) and vinylboronicanhydride pyridine complex (0.96 g, 4 mmole). The mixture was heated in a microwave at 160° C. (very high absorbance setting) for 1 hour. After cooling the mixture was partitioned between water (50 ml) and ethyl acetate (3×50 ml). The combined organic extracts were then washed with saturated brine (50 ml), separated and dried over sodium sulphate, filtered and evaporated to dryness. The residue was chromatographed on silica eluting with a gradient of 20-60% ethyl acetate/isohexane to give the title compound as a white solid (0.134 g).

1H-NMR (CDCl$_3$, 300 MHz) δ 10.45-11.05 (brs, 1H, NH), 8.71 (s, 1H, ArH), 8.12 (d, 1H, ArH), 7.47 (d, 1H, ArH), 7.12 (dd, 1H, CH), 6.25 (d, 1H, CH), 5.67 (d, 1H, CH), 3.97 (s, 3H, CH$_3$)

Step 2

3-Ethyl-1H-indazole-5-carboxylic acid methyl ester, 132

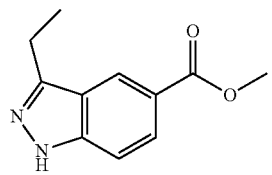

3-Vinyl-1H-indazole-5-carboxylic acid methyl ester (0.134 g, 0.66 mmole) in ethanol (10 ml) was hydrogenated at atmospheric pressure over 10% palladium on charcoal at ambient temperature for 20 hours. The mixture was then filtered through celite washing with ethanol. The combined filtrates were evaporated to dryness to give the title compound as a pale yellow oil (0.118 g).

1H-NMR (CDCl$_3$, 300 MHz) δ 10.71-11.02 (brs, 1H, NH), 8.51 (s, 1H, ArH), 8.05 (d, 1H, ArH), 7.45 (d, 1H, ArH), 3.97 (s, 3H, CH$_3$), 3.03 (q, 2H, CH$_2$), 1.45 (t, 3H, CH$_3$).

Step 3

1-(5-bromo-2-isobutoxy-benzyl)-3-ethyl-1h-indazole-5-carboxylic acid methyl ester, 133

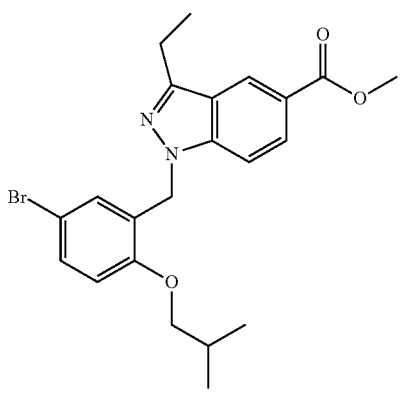 [SMILES: CCc1nn(Cc2cc(Br)ccc2OCC(C)C)c2ccc(C(=O)OC)cc12]

The titled compound was prepared following the method described in Example 21, step 4.

1H-NMR (CDCl$_3$, 300 MHz) δ 8.62 (s, 1H, ArH), 8.09 (dd, 1H, ArH), 7.39 (d, 1H, ArH), 7.34 (dd, 1H, ArH), 6.95 (d, 1H, ArH), 6.77 (d, 1H, ArH), 5.57 (s, 2H, CH$_2$), 3.97 (s, 3H, OCH$_3$), 3.77 (d, 2H, CH$_2$), 3.08 (q, 2H, CH$_2$), 2.07-2.18 (m, 1H, CH), 1.48 (t, 3H, CH$_3$), 1.05 (d, 6H, 2×CH$_3$).

Step 4

1-(5-bromo-2-isobutoxy-benzyl)-3-ethyl-1h-indazole-5-carboxylic acid, 134

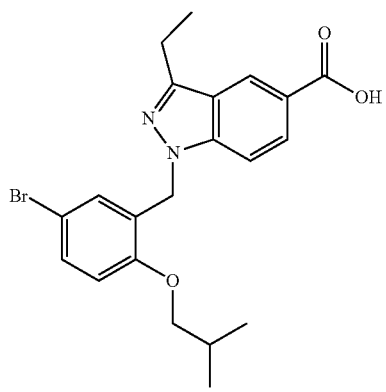 [SMILES: CCc1nn(Cc2cc(Br)ccc2OCC(C)C)c2ccc(C(=O)O)cc12]

The titled compound was prepared following the method described in Example 20, step 5.

1H-NMR (CDCl₃, 300 MHz) δ 8.62 (s, 1H, ArH), 8.09 (dd, 1H, ArH), 7.39 (d, 1H, ArH), 7.34 (dd, 1H, ArH), 6.95 (d, 1H, ArH), 6.77 (d, 1H, ArH), 5.57 (s, 2H, CH₂), 3.77 (d, 2H, CH₂), 3.08 (q, 2H, CH₂), 2.07-2.18 (m, 1H, CH), 1.48 (t, 3H, CH₃), 1.05 (d, 6H, 2×CH₃).

Example 65

1-[5-Bromo-2-(2-Ethyl-Butoxy)-Benzyl]-3-Ethyl-1H-Indazole-5-Carboxylic Acid, 135

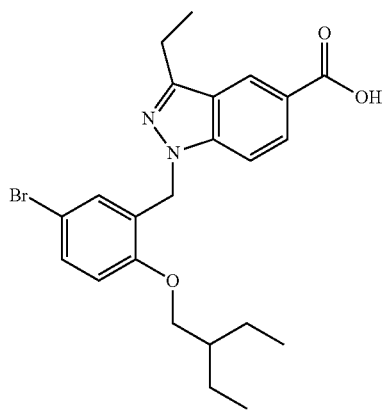 [SMILES: CCc1nn(Cc2cc(Br)ccc2OCC(CC)CC)c2ccc(C(=O)O)cc12]

The title compound was prepared following the same method as Example 64 but using Compound 80 as the starting material.

H-NMR (CDCl₃, 300 MHz) δ 8.61 (s, 1H, ArH), 8.09 (d, 1H, ArH), 7.32-7.39 (m, 2H, 2×ArH), 6.92 (d, 1H, ArH), 6.77 (d, 1H, ArH), 5.58 (s, 2H, CH₂), 3.88 (d, 2H, CH₂), 3.08 (q, 2H, CH₂), 1.65-1.77 (m, 1H, CH), 1.41-1.53 (m, 7H, 2×CH₂+CH₃), 0.95 (t, 6H, 2×CH₃).

Example 66

1-(5-Bromo-2-Isobutoxy-Benzyl)-2-Methyl-1H-Indole-5-Carboxylic Acid, 136

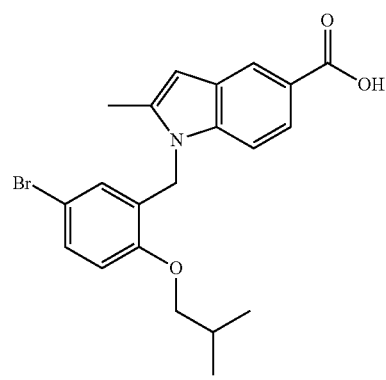 [SMILES: Cc1cc2cc(C(=O)O)ccc2n1Cc1cc(Br)ccc1OCC(C)C]

The title compound was prepared following the same method as Example 21.

1H-NMR (CDCl₃, 300 MHz) δ 8.41 (s, 1H, ArH), 7.92 (s, 1H, ArH), 7.28 (dd, 1H, ArH), 7.21 (d, 1H, ArH), 6.78 (d, 1H, ArH), 6.49 (s, 1H, ArH), 6.41 (d, 1H, ArH), 5.31 (s, 2H, CH₂), 3.81 (d, 2H, CH₂), 2.38 (s, 3H, CH₃), 2.15-2.25 (m, 1H, CH), 1.11 (d, 6H, 2×CH₃).

Example 67

1-(5-Bromo-2-Isobutoxy-Benzyl)-1H-Indole-5-Carboxylic Acid, 137

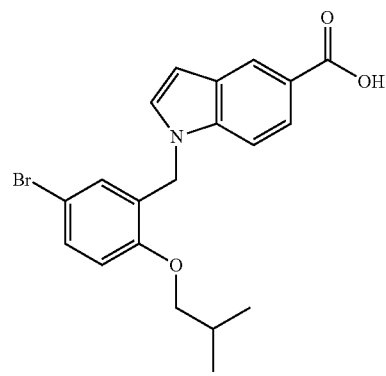 [SMILES: CC(C)COc1ccc(Br)cc1Cn1ccc2cc(C(=O)O)ccc21]

The title compound was prepared following the same method as Example 21.

1H-NMR (CDCl₃, 300 MHz) δ 8.51 (s, 1H, ArH), 7.99 (d, 1H, ArH), 7.35 (d, 1H, ArH), 7.31 (dd, 1H, ArH), 7.21 (d, 1H, ArH), 6.97 (d, 1H, ArH), 6.75 (d, 1H, ArH), 6.65 (d, 1H, ArH), 5.31 (s, 2H, CH₂), 3.77 (d, 2H, CH₂), 2.08-2.31 (m, 1H, CH), 1.04 (d, 6H, 2×CH₃).

Example 68

1-[5-Bromo-2-(2-Ethyl-Butoxy)-Benzyl]-2-Methyl-1H-Indole-5-Carboxylic Acid, 138

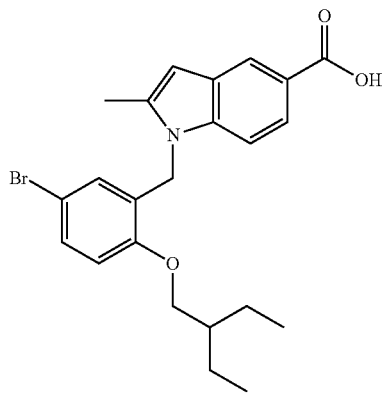 [SMILES: CCC(CC)COc1ccc(Br)cc1Cn1c(C)cc2cc(C(=O)O)ccc21]

The title compound was prepared following the same method as Example 21.

1H-NMR (CDCl₃, 300 MHz) δ 8.45 (s, 1H, ArH), 7.91 (d, 1H, ArH), 7.29 (dd, 1H, ArH), 7.19 (d, 1H, ArH), 6.81 (d, 1H, ArH), 6.47 (s, 1H, ArH), 6.38 (s, 1H, ArH), 5.29 (s, 2H, CH₂), 3.95 (d, 2H, CH₂), 2.38 (s, 3H, CH₃), 1.81-1.92 (m, 1H, CH), 1.48-1.62 (m, 4H, 2×CH₂), 0.97 (t, 6H, 2×CH₃).

Example 69

1-[5-Bromo-2-(2-Ethyl-Butoxy)-Benzyl]-1H-Indole-5-Carboxylic Acid, 139

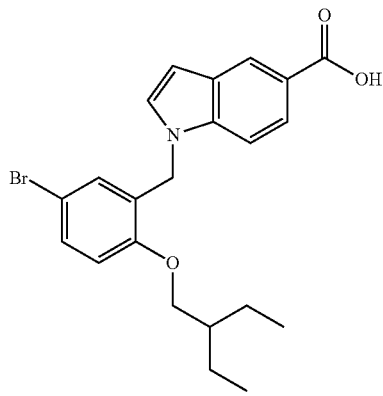 [SMILES: CCC(CC)COc1ccc(Br)cc1Cn1ccc2cc(C(=O)O)ccc21]

The title compound was prepared following the same method as Example 21.

1H-NMR (CDCl₃, 300 MHz) δ 8.52 (s, 1H, ArH), 7.99 (d, 1H, ArH), 7.35 (d, 1H, ArH), 7.31 (d, 1H, ArH), 7.19 (d, 1H, ArH), 6.91 (d, 1H, ArH), 6.82 (d, 1H, ArH), 6.69 (d, 1H, ArH), 5.32 (s, 2H, CH₂), 3.91 (d, 2H, CH₂), 1.62-1.74 (m, 1H, CH), 1.39-1.51 (m, 4H, 2×CH₂), 0.93 (t, 6H, 2×CH₃).

Example 70

1-[5-Bromo-2-(2-Ethyl-Butoxy)-Benzyl]-1H-Indole-6-Carboxylic Acid, 140

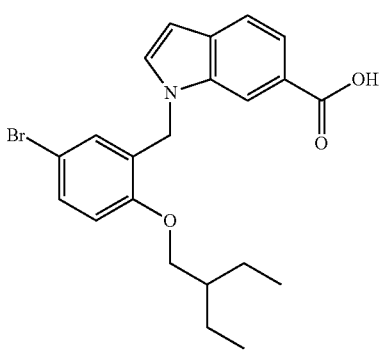 [SMILES: CCC(CC)COc1ccc(Br)cc1Cn1ccc2ccc(C(=O)O)cc21]

The title compound was prepared following the same method as Example 21.

1H-NMR (CDCl₃, 300 MHz) δ 8.22 (s, 1H, ArH), 7.91 (d, 1H, ArH), 7.71 (d, 1H, ArH), 7.35 (dd, 1H, ArH), 7.27 (d, 1H, ArH), 6.85 (d, 1H, ArH), 6.81 (d, 1H, ArH), 6.63 (d, 1H, ArH), 5.37 (s, 2H, CH₂), 3.93 (d, 2H, CH₂), 1.65-1.78 (m, 1H, CH), 1.41-1.52 (m, 4H, 2×CH₂), 0.94 (t, 6H, 2×CH₃)

Example 71

1-(2-Isobutoxy-5-Trifluoromethoxy-Benzyl)-1H-Indole-5-Carboxylic Acid, 141

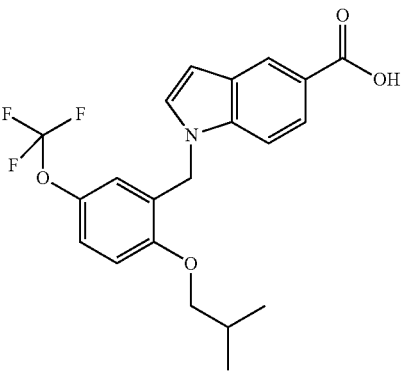 [SMILES: CC(C)COc1ccc(OC(F)(F)F)cc1Cn1ccc2cc(C(=O)O)ccc21]

The title compound was prepared following the same method as Example 21.

1H-NMR (CDCl₃, 300 MHz) δ 8.53 (s, 1H, ArH), 7.97 (d, 1H, ArH), 7.35 (d, 1H, ArH), 7.22 (d, 1H, ArH), 7.13 (dd, 1H, ArH), 6.96 (d, 1H, ArH), 6.68 (d, 1H, ArH), 6.61 (s, 1H, ArH), 5.35 (s, 2H, CH₂), 3.79 (d, 2H, CH₂), 2.07-2.21 (m, 1H, CH), 0.94 (d, 6H, 2×CH₃).

Example 72

1-(5-Bromo-2-Isobutoxy-Benzyl)-1H-Pyrrolo[2,3-b]Pyridine-5-Carboxylic Acid, 142

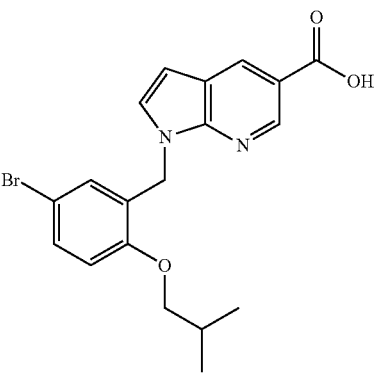 [SMILES: CC(C)COc1ccc(Br)cc1Cn1ccc2cc(C(=O)O)cnc21]

The title compound was prepared following the same method as Example 21.

1H-NMR (CDCl$_3$, 300 MHz) δ 9.13 (s, 1H, ArH), 8.65 (s, 1H, ArH), 7.36 (dd, 1H, ArH), 7.29 (d, 1H, ArH), 7.13 (d, 1H, ArH), 6.75 (d, 1H, ArH), 6.61 (d, 1H, ArH), 5.53 (s, 2H, CH$_2$), 3.75 (d, 2H, CH$_2$), 2.01-2.18 (m, 1H, CH), 1.02 (d, 6H, 2×CH$_3$).

Example 73

1-(5-Bromo-2-Isobutoxy-Benzyl)-1H-Pyrrolo[3,2-b]Pyridine-5-Carboxylic Acid, 143

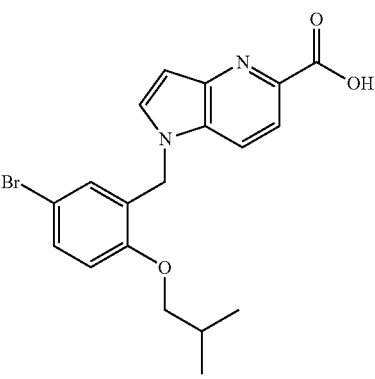 [SMILES: CC(C)COc1ccc(Br)cc1Cn1ccc2nc(C(=O)O)ccc21]

The title compound was prepared following the same method as Example 21.

1H-NMR (CDCl$_3$, 300 MHz) δ 8.09 (d, 1H, ArH), 7.81 (d, 1H, ArH), 7.55 (d, 1H, ArH), 7.39 (dd, 1H, ArH), 6.99 (d, 1H, ArH), 6.81 (s, 1H, ArH), 6.78 (d, 1H, ArH), 5.33 (s, 2H, CH$_2$), 3.74 (d, 2H, CH$_2$), 1.98-2.12 (m, 1H, CH), 0.99 (d, 6H, 2×CH$_3$).

Example 74

1-(2-Isobutoxy-5-Trifluoromethoxy-Benzyl)-1H-Pyrrolo[2,3-b]Pyridine-5-Carboxylic Acid, 144

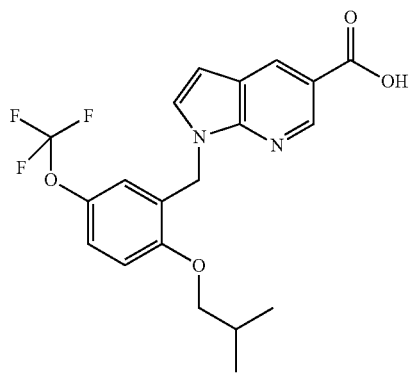 [SMILES: CC(C)COc1ccc(OC(F)(F)F)cc1Cn1ccc2cc(C(=O)O)cnc21]

The title compound was prepared following the same method as Example 21.

1H-NMR (CDCl$_3$, 300 MHz) δ 8.99 (s, 1H, ArH), 8.61 (s, 1H, ArH), 7.23 (d, 1H, ArH), 7.05 (dd, 1H, ArH), 6.81 (d, 1H, ArH), 6.78 (s, 1H, ArH), 6.54 (d, 1H, ArH), 5.47 (s, 2H, CH$_2$), 3.75 (d, 2H, CH$_2$), 1.98-2.12 (m, 1H, CH), 0.97 (d, 6H, 2×CH$_3$).

Example 75

1-(2-Isobutoxy-5-Trifluoromethoxy-Benzyl)-3-Methyl-1H-Indole-5-Carboxylic Acid, 145

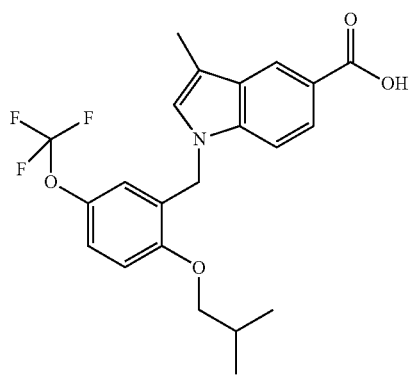 [SMILES: Cc1cn(Cc2cc(OC(F)(F)F)ccc2OCC(C)C)c2ccc(C(=O)O)cc12]

The title compound was prepared following the same method as Example 21.

1H-NMR (CDCl$_3$, 300 MHz) δ 8.48 (s, 1H, ArH), 7.97 (dd, 1H, ArH), 7.31 (d, 1H, ArH), 7.11 (dd, 1H, ArH), 6.95 (s, 1H, ArH), 6.85 (d, 1H, ArH), 6.61 (d, 1H, ArH), 5.28 (s, 2H, CH$_2$), 3.75 (d, 2H, CH$_2$), 2.48 (s, 3H, CH$_3$), 2.06-2.21 (m, 1H, CH), 1.05 (d, 6H, 2×CH$_3$).

Example 76

1-[2-(2-Ethyl-Butoxy)-5-Trifluoromethoxy-Benzyl]-1H-Pyrrolo[2,3-b]Pyridine-5-Carboxylic Acid, 146

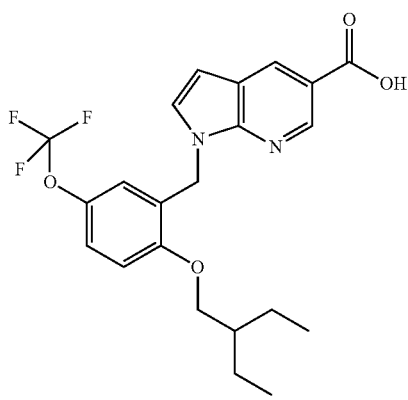 [SMILES: CCC(CC)COc1ccc(OC(F)(F)F)cc1Cn1ccc2cc(C(=O)O)cnc21]

The title compound was prepared following the same method as Example 21.

1H-NMR (CDCl$_3$, 300 MHz) δ 9.11 (d, 1H, ArH), 8.71 (d, 1H, ArH), 7.29 (d, 1H, ArH), 7.11 (dd, 1H, ArH), 6.85-6.91 (m, 2H, 2×ArH), 6.61 (d, 1H, ArH), 5.55 (s, 2H, CH$_2$), 3.92 (d, 2H, CH$_2$), 1.59-1.71 (m, 1H, CH), 1.37-1.48 (m, 4H, 2×CH$_2$), 0.89 (t, 6H, 2×CH$_3$).

Example 77

1-[2-(2-Ethyl-Butoxy)-5-Trifluoromethoxy-Benzyl]-3-Methyl-1H-Indole-5-Carboxylic Acid, 147

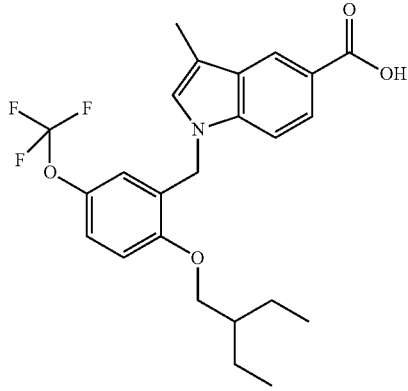 [SMILES: CCC(CC)COc1ccc(OC(F)(F)F)cc1Cn1cc(C)c2cc(C(=O)O)ccc21]

The title compound was prepared following the same method as Example 21.

1H-NMR (CDCl$_3$, 300 MHz) δ 8.45 (s, 1H, ArH), 7.95 (d, 1H, ArH), 7.28 (d, 1H, ArH), 7.11 (dd, 1H, ArH), 6.93 (s, 1H, ArH), 6.88 (d, 1H, ArH), 6.65 (d, 1H, ArH), 5.25 (s, 2H, CH$_2$), 3.93 (d, 2H, CH$_2$), 2.41 (s, 3H, CH$_3$), 1.62-1.75 (m, 1H, CH), 1.41-1.53 (m, 4H, 2×CH$_2$), 0.93 (t, 6H, 2×CH$_3$).

Example 78

1-[5-Bromo-2-(2-Ethyl-Butoxy)-Benzyl]-1H-Benzoimidazole-5-Carboxylic Acid, 148

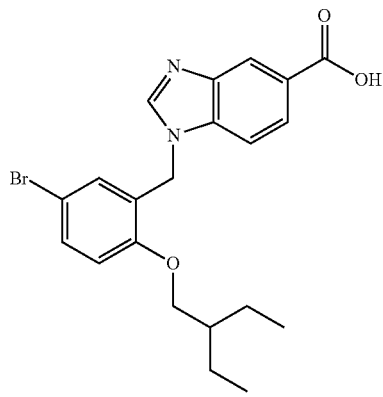 [SMILES: CCC(CC)COc1ccc(Br)cc1Cn1cnc2cc(C(=O)O)ccc21]

The title compound was prepared following the same method as Example 21.

1H-NMR (CDCl$_3$, 300 MHz) δ 8.59 (s, 1H, ArH), 8.07 (dd, 1H, ArH), 8.02 (s, 1H, ArH), 7.39-7.47 (m, 2H, 2×ArH), 7.19 (d, 1H, ArH), 6.82 (d, 1H, ArH), 5.31 (s, 2H, CH$_2$), 3.87 (d, 2H, CH$_2$), 1.59-1.69 (m, 1H, CH), 1.33-1.45 (m, 4H, 2×CH$_2$), 0.88 (t, 6H, 2×CH$_3$).

Example 79

1-(5-Bromo-2-Isobutoxy-Benzyl)-1H-Benzoimidazole-5-Carboxylic Acid, 149

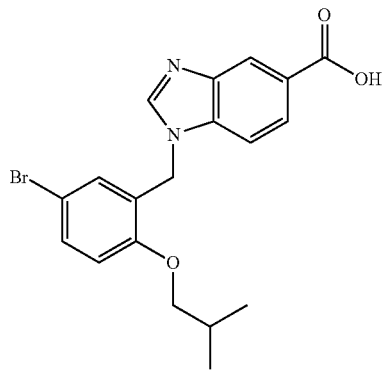 [SMILES: CC(C)COc1ccc(Br)cc1Cn1cnc2cc(C(=O)O)ccc21]

The title compound was prepared following the same method as Example 21.

1H-NMR (CDCl$_3$, 300 MHz) δ 8.51 (s, 1H, ArH), 8.03 (s, 1H, ArH), 8.01 (dd, 1H, ArH), 7.37-7.46 (m, 2H, 2×ArH), 7.19 (d, 1H, ArH), 6.78 (d, 1H, ArH), 5.31 (s, 2H, CH$_2$), 3.71 (d, 2H, CH$_2$), 1.97-2.09 (m, 1H, CH), 0.88 (d, 6H, 2×CH$_3$).

While the Examples, above, demonstrate the preparation of certain indole and indazole compounds, isoindoles, as well as other aza compounds may also be prepared by analogous methods as those shown in the Examples.

The above compounds were tested for PG antagonist activity as follows using human recombinant prostanoid receptor (DP$_1$, EP$_{1-4}$, FP, IP and TP) stable cell lines: In order to measure the response of $G_s$ and $G_i$ coupled prostanoid receptors as a $Ca^{2+}$ signal, chimeric G protein cDNAs were used. Stable cell lines over-expressing human prostanoid $DP_1$, $EP_{1-4}$, FP, IP, and TP receptors were established as follows:

Briefly, human prostanoid $DP_1$, $EP_2$, and $EP_4$ receptor cDNAs were co-transfected with chimeric $G_{qs}$ cDNA containing a haemagglutanin (HA) epitope; human prostanoid $EP_3$ receptors were co-transfected with chimeric $G_{qi}$-HA; human $EP_1$, FP, IP, and TP receptor cDNAs were expressed with no exogenous G-proteins. $G_{qs}$ and $G_{qi}$ chimeric cDNAs (Molecular Devices, Sunnyvale, Calif., U.S.A.), as well as cDNAs of prostanoid receptors, were cloned into a $pCEP_4$ vector with a hygromycin B selection marker. Transfection into HEK-293 EBNA (Epstein-Barr virus nuclear antigen) cells was achieved by the FuGENE 6 transfection Reagent (Roche Applied Science, Indianapolis, Ind., USA). Stable transfectants were selected according to hygromycin resistance. Because $G_{qs}$ and $G_{qi}$ contained an HA epitope, G-protein expression was detected by Western blotting analysis using anti-mouse HA monoclonal antibody and horseradish peroxidase (HRP)-conjugated secondary antibody, while functional expression of prostanoid receptors was detected by FLIPR screening (Matias et al., 2004). These stable cell lines were validated using previously published antagonists at 10 µM against serial dilutions of standard agonists by FLIPR functional assays for $Ca^{2+}$ Signaling (as described below).

$Ca^{2+}$ signaling studies were performed using a FLIPR TETRA system (Molecular Devices, Sunnyvale, Calif., USA) in the 384-format. This is a high-throughput instrument for cell-based assays to monitor $Ca^{2+}$ signaling associated with GPCRs and ion channels. Cells were seeded at a density of $5 \times 10^4$ cells/well in BioCoat poly-D-lysine coated, black wall, clear bottom 384-well plates (BD Biosciences, Franklin lakes, NJ, USA) and allowed to attach overnight in an incubator at 37° C. The cells were then washed twice with HBSS-HEPES buffer (Hanks' balanced salt solution without bicarbonate and phenol red, 20 mM HEPES, pH 7.4) using an ELx405 Select CW Microplate Washer (BioTek, Winooski, Vt., USA). After 60 min of dye-loading in the dark using the $Ca^{2+}$-sensitive dye Fluo-4AM (Invitrogen, Carlsbad, Calif., USA), at a final concentration of $2 \times 10^{-6}$M, the plates were washed 4 times with HBSS-HEPES buffer to remove excess dye and leaving 50 µl of buffer in each well. The plates were then placed in the FLIPR TETRA instrument and allowed to equilibrate at 37° C. Compounds were added in a 25 µl volume to each well to give final concentrations of 0.1 µM, 0.3 µM, 1 µM, 3 µM, 10 µM, and 30 µM; or 0.067 µM, 0.1 µM, 0.2 µM, 0.3 µM, 0.67 µM, and 1 µM for cells over-expressing TP receptors. After 4.5 minutes, a 7-point serial dilution of the standard agonist for the corresponding receptor, in a 25 µl volume was injected at the final concentrations from $10^{-11}$M to $10^{-5}$M in 10-fold serial dilution increments for cells expressing human recombinant $DP_1$, $EP_1$, $EP_2$, $EP_3$, $EP_4$, FP, and IP receptors. The dose range for the standard agonist for human recombinant TP receptors was from $10^{-12}$M to $10^{-6}$M. HBSS-HEPES buffer was used as the negative control for the standard agonists. Cells were excited with LED (light emitting diode) excitation at 470-495 nm and emission was measured through an emission filter at 515-575 nm. Assay plates were read for 3.5 minutes using the $FLIPR^{TETRA}$. The peak increase in fluorescence intensity was recorded for each well. On each plate, negative controls, dose response of positive controls, and co-treatments of antagonist-agonist for each dose were in triplicates. Standard agonists were as follows: DP=BW 245C, $EP_1$-$EP_4$=$PGE_2$, FP=17-phenyl-$PGF_{2\alpha}$, IP=Cicaprost, and TP=U-46619. The peak fluorescence change in each well containing drug was expressed relative to vehicle controls with the standard agonist at $10^{-6}$M (the positive control). To obtain concentration-response curves, compounds were tested in triplicate in each plate over the desired concentration range.

Data Processing

All plates were subjected to appropriate baseline corrections. Maximum fluorescence values were exported. The raw data of n=1 was first processed by Activity Base using nonlinear regression curve fit to calculate the percentage activity of each data point relative to the positive control (=$10^{-6}$M of the standard agonist). Then n=3 of this data were exported to GraphPad Prism 4 to calculate the average $EC_{50}$ of the standard agonist, and the $IC_{50}$ (the concentration of the antagonist required to inhibit half the standard agonist activity) were calculated using nonlinear regression curve fit, with constraints of bottom constant equal to 0 and top constant equal to 100. Calculation of Kb=[Antagonist Concentration]/($IC_{50}/EC_{50}$-1). When no antagonism was detected or when Kb≥10,000 nM, the antagonist is defined as not active (NA).

The results of the above testing are reported in TABLE 1, below.

| Example | FP | DP | $EP_1$ | $EP_2$ | $EP_3$ | $EP_4$ | IP | TP |
|---|---|---|---|---|---|---|---|---|
| 1 | 560 | 2100 | 180 | 8700 | 5200 | 70 | 2200 | 150 |
| 2 | 160 | 1300 | 140 | 2900 | 1100 | 20 | 1100 | 110 |
| 3 | 50 | 1200 | 16 | 3400 | 3000 | 60 | 1200 | 4 |
| 4 | 20 | 700 | 6 | 1800 | 1500 | 25 | 800 | 2 |
| 5 | 340 | 2100 | 130 | NA | NA | 50 | 5200 | 40 |
| 6 | 2400 | 7100 | NA | NA | NA | NA | NA | 150 |
| 7 | 300 | 1900 | 45 | 4400 | NA | 1800 | 1300 | 20 |
| 8 | 200 | 2600 | 220 | 5000 | NA | 1300 | 2800 | 2100 |
| 9 | 20 | 1200 | 90 | 3200 | 4900 | 3000 | 1350 | PAgonist |
| 10 | 30 | 440 | 50 | 500 | 1100 | 20 | 400 | 20 |
| 11 | 120 | 900 | 120 | 2000 | 6500 | 110 | 5500 | 120 |
| 12 | 120 | 1600 | 360 | 7900 | NA | 1150 | 5000 | 44 |
| 13 | 20 | 1200 | 50 | 1900 | 8500 | 2700 | 600 | 900 |
| 14 | 30 | 600 | 20 | 400 | 1500 | 15 | 340 | 600 |
| 15 | 130 | 1800 | 190 | 3300 | 8400 | 200 | 1800 | 20 |
| 16 | 3000 | 1500 | 90 | NA | 4000 | 600 | 6600 | 400 |
| 17 | 2300 | 3500 | 40 | NA | NA | 600 | NA | 3300 |
| 18 | 20 | 1400 | 40 | NA | 4000 | 60 | 6500 | 4 |
| 19 | 16 | 1200 | 12 | 8800 | 3600 | 14 | 4600 | 50 |
| 20 | 13 | 500 | 30 | NA | NA | 30 | 2700 | 50 |
| 21 | 30 | 100 | 14 | 3500 | 2200 | 70 | 900 | 13 |
| 22 | 140 | 1700 | 16 | NA | NA | 350 | 6000 | 5 |
| 23 | 170 | 900 | 30 | 7100 | 1200 | 50 | 500 | 1 |
| 24 | 40 | 160 | 20 | 4500 | 2440 | 150 | 1430 | 80 |
| 25 | 180 | 220 | 27 | 9300 | 4500 | 160 | 1030 | 50 |
| 26 | 500 | 1700 | 80 | NA | 3300 | 70 | 1800 | 18 |
| 27 | 200 | 1600 | 110 | 3640 | 2600 | 53 | 440 | 20 |
| 28 | 70 | 730 | 43 | 9200 | 2220 | 40 | 1530 | 7 |
| 29 | | | | | | | | |
| 30 | 140 | 1700 | 16 | NA | NA | 350 | 6000 | 5 |
| 31 | 170 | 900 | 30 | 7100 | 1200 | 50 | 520 | 1 |
| 32 | 50 | 1700 | 210 | NA | NA | 5000 | 7400 | 50 |
| 33 | 70 | 350 | 70 | 2600 | 1400 | 30 | 400 | 1 |
| 34 | 3200 | 5400 | 70 | NA | NA | NA | NA | 100 |
| 35 | 4300 | 1900 | 4200 | NA | NA | 670 | NA | 1200 |
| 36 | 580 | 1100 | 60 | 2900 | 4000 | 1200 | 200 | 3 |
| 37 | NA | 1300 | 480 | NA | 3400 | 700 | NA | 200 |
| 38 | 1100 | 630 | 70 | 2100 | 1700 | 400 | 60 | 3 |
| 39 | NA | 1000 | 1200 | NA | 5500 | 1600 | 4900 | 110 |
| 40 | 270 | 1000 | 60 | 900 | 12000 | 2500 | PAg | Ag |
| 41 | NA | 4700 | NA | NA | NA | NA | 9800 | 7400 |
| 42 | 900 | 160 | 24 | NA | 1900 | 1800 | 3400 | 20 |
| 43 | 2200 | 2000 | 1200 | NA | 5500 | 1600 | 4900 | 110 |
| 44 | 1400 | PAg | 240 | NA | 1600 | 3200 | PAg | 1 |

-continued

| Example | FP | DP | EP$_1$ | EP$_2$ | EP$_3$ | EP$_4$ | IP | TP |
|---|---|---|---|---|---|---|---|---|
| 45 | 1400 | 2800 | 23 | NA | NA | 2000 | 7000 | 80 |
| 46 | NA | 2500 | 7100 | NA | NA | NA | NA | 150 |
| 47 | 4700 | 700 | 2000 | NA | NA | NA | 4800 | NA |
| 48 | NA | NA | 260 | NA | NA | NA | NA | 500 |
| 49 | 70 | 3500 | 540 | NA | NA | 50 | 3200 | 6 |
| 50 | 4900 | 2400 | 90 | NA | 7100 | 1800 | NA | 5700 |
| 51 | 110 | 600 | 70 | NA | 2600 | 270 | 1100 | 50 |
| 52 | 11 | 2300 | 24 | 3800 | 2100 | 10 | NA | 2 |
| 53 | 230 | NA | 1500 | NA | NA | NA | NA | 1200 |
| 54 | 1100 | 9900 | 1300 | NA | NA | 2700 | NA | 640 |
| 55 | 40 | 1200 | 40 | NA | NA | 2100 | NA | 300 |
| 56 | 24 | 1800 | 24 | NA | 8800 | 150 | 4100 | 5 |
| 57 | 190 | 5500 | 27 | NA | NA | 1300 | NA | 150 |
| 58 | 60 | 1800 | 30 | NA | 9800 | 380 | NA | 70 |
| 59 | 1300 | 520 | 280 | NA | 5400 | 190 | 540 | 320 |
| 60 | 2500 | 580 | 410 | 7500 | 5100 | 150 | 630 | 410 |
| 61 | 1500 | 740 | 180 | NA | NA | 760 | 1750 | 300 |
| 62 | NA | 5800 | NA | NA | NA | NA | NA | NA |
| 63 | 2400 | NA | 1200 | NA | 7400 | 2500 | 5000 | 180 |
| 64 | 190 | 260 | 5 | 3100 | 2900 | 50 | 700 | 8 |
| 65 | PAg | 1500 | 40 | 6500 | 4700 | 55 | 880 | 52 |
| 66 | 23 | NA | 50 | NA | NA | 1400 | 4600 | 320 |
| 67 | 100 | NA | 60 | NA | NA | 340 | NA | 160 |
| 68 | NA | NA | NA | NA | NA | 9700 | 6600 | NA |
| 69 | 800 | 3700 | 250 | NA | 7900 | 130 | 3000 | 550 |
| 70 | NA | 2200 | 200 | NA | NA | 6000 | NA | 320 |
| 71 | 120 | NA | 100 | NA | NA | 280 | NA | 600 |
| 72 | 25 | 1500 | 10 | NA | NA | 220 | 2000 | 3 |
| 73 | 430 | NA | 80 | NA | NA | NA | 9000 | 8 |
| 74 | 660 | 290 | 60 | NA | 2800 | 440 | 1400 | 20 |
| 75 | 330 | 1300 | 20 | 6400 | NA | 280 | 4400 | 300 |
| 76 | 660 | 290 | 60 | NA | 2800 | 440 | 1400 | 20 |
| 77 | 9600 | 3600 | 900 | 9200 | NA | 1500 | NA | 1100 |
| 78 | 800 | 3800 | 145 | NA | NA | 35 | 3000 | 16 |
| 79 | 80 | 2000 | 11 | NA | 8700 | 80 | 7000 | 8 |

As shown in TABLE 1, the preferred compounds of this invention are pan antagonists having activity at the FP, DP$_1$, EP$_1$, EP$_4$ and TP receptors, but are inactive at the IP, EP$_2$ and EP$_3$ receptors. Thus, these compounds have a biological selectivity profile making them useful in treating diseases and conditions which are ameliorated by the IP/EP$_2$ and/or EP$_3$ receptor stimulation, without the symptoms side effects mediated by the FP, DP, EP$_1$, EP$_4$ and TP receptors. Also, based on the data generated for this TABLE 1, it appears that the 5-carboxylic acid compounds are more active at the EP$_1$ and EP$_4$ receptors than the 4 or 6-carboxylic acid compounds. Therefore, the 5-carboxylic acid compounds are preferred.

Thus, the compounds of this invention compound may be administered to treat DP1, FP, EP$_1$, TP and/or EP4 receptor mediated diseases or conditions.

For example, said condition or disease may be related to inflammation, or said, FP, EP$_1$, TP and/or EP$_4$ receptor mediated condition or disease may be selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, endometriosis, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pre-term labor, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

The compounds of the present invention may be administered as a surgical adjunct in ophthalmology for cataract removal and artificial lens insertion, ocular implant procedures, photorefractive radial keratotomy and other ophthalmogical laser procedures or as a surgical adjunct in a procedure involving skin incisions, relief of pain and inflammation and scar formation/keloids post-surgery, for treating sports injuries and general aches and pains in muscles and joints.

Preferably, said DP$_1$, FP, EP$_1$, TP, and/or EP$_4$ receptor mediated condition or disease is an EP$_1$ and/or EP$_4$ receptor mediated condition or disease. Preferably, said DP$_1$, FP, EP$_1$, TP and/or EP$_4$ receptor mediated condition or disease is an allergic condition, e.g. an dermatological allergy, or an ocular allergy, or a respiratory allergy, e.g. nasal congestion, rhinitis, and asthma.

The condition or disease may be related to pain. The condition or disease may be selected from the group consisting of arthritis, migraine, and headache. The condition or disease may be associated with the gastrointestinal tract, wherein said condition or disease may be peptic ulcer, heartburn, reflux esophagitis, erosive esophagitis, non-ulcer dyspepsia, infection by *Helicobacter pylori*, alrynitis, and irritable bowel syndrome.

The condition or disease may be selected from the group consisting of hyperalgesia and allodynia, or said condition or disease may be related to mucus secretion, wherein said mucus secretion is gastrointestinal, or occurs in the nose, sinuses, throat, or lungs.

The condition or disease is related to abdominal cramping, e.g. said condition, menstrual cramping or disease may be irritable bowel syndrome. The condition or disease may be a bleeding disorder, or a sleep disorder, or mastocytosis.

The condition or disease may be associated with elevated body temperature, or ocular hypertension and glaucoma, or ocular hypotension. The condition may relate to surgical procedures to treat pain, inflammation and other unwanted sequelae wherein said surgical procedure includes incision, laser surgery or implantation.

The present invention also relates to a method of treating inflammation resulting from inflammatory diseases characterized by monocytic infiltration caused by the secretion of cytokines and/or chemokines by administration, to a patient in need of said treatment, of a pharmaceutical composition comprising a compound of the present invention The current finding that the compounds of this invention are effective in attenuating the production of TNF family cytokines (TNFα), and the classical interleukin-1 (IL-1) family cytokines is especially important. These cytokines exert a broad spectrum of biological and pathological effects. They play key roles in inflammation and RA pathogenesis by stimulating the release of multiple proinflammatory cytokines, including themselves, through the NFκB signaling pathway. Although alleviating the symptoms of RA in 50-65% of patients, a TNFα antibody is very expensive to use compared to chemically synthesized small molecules, inconvenient to administer usually requiring injections, and has been linked to tuberculosis, lymphoma, and other adverse effects. Unlike a TNFα antibody that totally eliminates all circulating TNFα in the system; the compounds of this invention only attenuate the production of TNFα by inhibiting proinflammatory PG receptors. Therefore, the adverse effects associated with a TNFα antibody in elevating infectious and cancerous tendency is less likely.

Proinflammatory elements TNF, RANTES, and MCP-1 are involved in the cascade of events in the early and late stages of atherosclerosis. Plasma MCP-1 levels have been linked to cardiovascular disease risk factors in clinical studies. Platelet activation leads to the release of MIP-1α, RANTES, and IL-8, which attract leukocytes and further activate other platelets. These evidences provide a direct linkage between homeostasis, infection, and inflammation and the development of atherosclerosis. The compounds of this invention are able to target multiple biomarkers of inflammation, thrombosis, and atherothrombosis simultaneously, which may confer pharmaceutical potential on the compounds of this invention in treating atherosclerosis and atherothrombosis. As a result, the compounds of this invention are unlikely to be associated with cardiovascular liability as in the case of the COXIBs, conversely it may even have a beneficial effect on cardiovascular function.

In summary, because of their ability to suppress the synthesis of some key proinflammatory cytokines/chemokines IL-8, MCP-1, MDC, RANTES, and TNFα, the compounds of the present invention are believed to be, not only at least as effective as COXIBs and NSAIDs in RA treatment, but also are a safer therapy in RA treatment. They are also a potential therapy for cardiovascular diseases.

The compounds of this invention are believed to treat or prevent inflammation at least in part by the decreasing the amount of the secretion of certain cytokines and/or chemokines that result from the exposure of the patient to a stimulant. In particular, the secretion of VEGF, MIP-1β, IL-8, MCP-1, MDC, and RANTES may be reduced in those instances where said secretions are triggered by lipopolysaccharides (LPS) and or TNFα.

Interleukin-8 (IL-8): functions as a potent chemoattractant and activator of neutrophils, IL-8 is produced in response to stimulation with either IL-1 or TNFα. IL-8 not only accounts for a significant proportion of the chemotactic activity for neutrophils in rheumatoid arthritis (RA) synovial fluids, but also is a potent angiogenic factor in the RA synovium. Monocyte chemoattractant protein-1 (MCP-1, or CCL-2): is not only believed to play a role in inflammatory diseases characterized by monocytic infiltration, such as rheumatoid arthritis ("RA"), psoriasis, and atherosclerosis, but is also implicated in other diseases, such as atopic dermatitis, renal disease, pleurisy, allergy and asthma, colitis, endometriosis, polymyositis and dermatomyositis, uveitis, restenosis, brain inflammation and obesity. MCP-1 also controls leukocyte trafficking in vascular cells involved in diabetes and diabetes-induced atherosclerosis. MCP-1 antibodies are potential therapeutic agents for treating MCP-1/CCR2-mediated multiple inflammatory diseases.

Tumor necrosis factor α (TNFα): mainly secreted by macrophages and recognized for its importance in activating the cytokine cascade. TNFα stimulates the production of proinflammatory cytokines/chemokines, collagenases, metalloproteinases, and other inflammatory mediators; activates endothelial cells and neutrophils; promotes T- and B-cell growth, as well as stimulating bone resorption. The TNFα antibody infliximab not only decreases the production of local and systemic proinflammatory cytokines/chemokines, but also reduces serum MMP-3 production, nitric oxide synthase activity, VEGF release, and angiogenesis in inflamed joints.

Macrophage-derived chemokine (MDC) induces chemotaxis for monocyte-derived dendritic cells, activated T cells and natural killer (NK) cells (Ho et al., 2003). Highly expressed by the three major cell types involved in allergic inflammation: eosinophils, basophils, and Th2 lymphocytes (Garcia et al., 2005), as well as highly expressed in atopic dermatitis (Pivarcsi et al., 2005), MDC plays a role in inflammatory diseases such as allergic asthma and atopic dermatitis (Ho et al., 2003). Significantly enhanced in keratinocytes of patients with atopic dermatitis, MDC could be a candidate therapeutic target for inflammatory skin disease such as atopic dermatitis (Qi et al., 2009). MDC is also implicated in disease activity of RA. After combination treatment with the disease-modifying anti-rheumatic drugs leflunomide and methotrexate in RA patients, plasma MCP-1 and MDC concentrations were significantly lower, and so was the recruitment of inflammatory cells into the sites of inflammation (Ho et al., 2003). Moreover, MDC also amplify platelet activation and has been associated with the pathogenesis of atherosclerotic disease including thrombosis (Gleissner et al., 2008).

Regulated on Activation, Normal T Cell Expressed and Secreted (RANTES) is a chemoattractant for blood monocytes, memory T-helper cells and eosinophils, and plays an active role in recruiting leukocytes into inflammatory sites. It also stimulates the release of histamine from basophils, activates eosinophils and causes hypodense eosinophils, which are associated with diseases such as asthma and allergic rhinitis. RANTES receptor CCR5 is also expressed on cells involved in atherosclerosis (e.g. monocytes/macrophages, T lymphocytes, or Th1-type cells), and is specialized in mediating RANTES-triggered atherosclerotic plaque formation (Zernecke et al., 2008). Like MCP-1, stimulation with RANTES enhances production of IL-6 and IL-8 in RA fibroblast-like synovial cells; elevated MMP-3 production by chondrocytes, and inhibited proteoglycan synthesis and enhanced proteoglycan release from the chondrocytes (Iwamoto et al., 2008). Both MCP-1 and RANTES were found to play an important role in allergic lung inflammation, lung leukocyte infiltration, bronchial hyper-responsiveness, and the recruitment of eosinophils in the pathogenesis of asthma (Conti et al., 2001). Similar to MCP-1, RANTES also enhances the inflammatory response within the nervous system, which plays an apparent role in the pathogenesis of multiple sclerosis (Conti et al., 2001) Inhibitors for RANTES may provide clinical benefits in treating inflammation, CNS disorders, parasitic disease, cancer, autoimmune and heart diseases (Castellani et al., 2007). Thus the compounds of the present invention, given locally or systemically, may be useful for treatment or alleviating symptoms of T cell mediated autoimmune disorders such as RA and multiple sclerosis.

While the use of the compounds of this invention are believed to decrease the secretion of the above cytokines, it is also believed that the compounds of this invention are effective to decrease the secretion of ENA-7, PAI-1, CD-10, G-CSF, GM-CSF, IL-1 α and IL-18, as well.

The compounds of this invention may be also tested for efficacy in treating uveitis as described below.

Arachidonate Induced Uveitis

The rational for this protocol is to use arachidonate to directly produce ocular anterior segment uveitis, as opposed to using lipopolysaccharide (LPS) to indirectly release arachidonic acid.

Induction of Uveitis:

Conscious male or female Dutch-belted pigmented rabbits weighing 2.5-3 kg are used for all in vivo slit lamp studies. Four animals are employed per test group. The right eye of each animal receiving 35 µl of topically administered test and the contralateral left eye of each animal receiving 35

µl of topically administered vehicle (t=0 minutes), followed 30 minutes later by treatment with 35 µl of 0.5% sodium arachidonate onto the surface of both eyes (t=30 minutes). Both eyes are examined by slit lamp 60 minutes following sodium arachdionate challenge (t=90 minutes) at 16× magnification under both white light and blue light illumination at an approximate angle of 45° through 1 mm and 5 mm slit widths.

Measurement of Anterior Chamber Leukocyte Infiltration:

Anterior chamber leukocyte infiltration is measured using a numerical scoring system to estimate cell number per field defined by a 5 mm slit width: 0=no cells per field (no response); 1=1-10 cells per field (mild); 2=11-20 cells per field (moderate); 3=26-50 cells per field (severe); 4=>50 cells per filed (florid). Results are reported as the mean score value±S.E.M.

The compounds of this invention may be tested according to the method described in "Characterization of Receptor Subtypes Involved in Prostanoid-Induced Conjunctival Pruritis and Their Role in Mediating Conjunctival Itching", Vol. 279, No. 1, (JPET) 279, 137-142' 1996 for their efficacy in alleviating itch to thereby indicate that the compounds of this invention are useful in treating allergic conjunctivitis. This reference is hereby incorporated by reference.

While the use of the compounds of this invention are believed to decrease the secretion of the above cytokines, it also is believed that the compounds of this invention are effective to decrease the secretion of ENA-7, PAI-1, CD-10, G-CSF, GM-CSF, IL-1α and IL-18, as well.

Finally, said condition that may be treated with the compounds of this invention may be related to pain and inflammation and post-surgical scar and keloid formation.

In view of the various diseases and conditions that may be treated with the compositions of this invention there is provided a pharmaceutical product comprising a compound having the following formula:

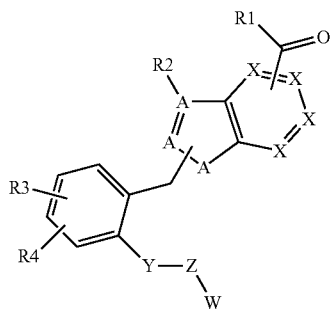

Wherein:
X is N or $CR_7$;
A is N or $CR_7$ with the proviso that at least one A is N and when each A is N, $R_2$ is absent;
Y is $(CH_2)_m$, wherein m is 0 or an integer of from 1 to 3;
Z is selected from the group consisting of O, S, SO, $SO_2$ and $(CH_2)_p$, wherein p is 0 or an integer of from 1 to 3;
W is hydrocarbyl or substituted hydrocarbyl;
$R_1$ is selected from the group consisting of $OR_7$, $NH_2$, $N(R_7)_2$, and $N(R_7)SO_2R_7$;
$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
$R_3$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
$R_4$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
and/or a pharmaceutically acceptable salt or a prodrug thereof.

The compounds of the present invention may be formulated, packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, hyperpyrexia, endometriosis gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pre-term labor pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

Those skilled in the art will readily understand that for administration the compounds disclosed herein can be admixed with pharmaceutically acceptable excipients which, per se, are well known in the art. Specifically, a drug to be administered systemically, it may be formulated as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 which are hereby incorporated by reference to form osmotic therapeutic tablets for control release. Liquid pharmaceutically administrable dosage forms can, for example, comprise a solution or suspension of one or more of the compounds of the present invention and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectable formulations can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds of the present invention administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Similarly, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edentate disodium, although other chelating agents may also be used in place or in conjunction with it.

For topical use, creams, ointments, gels, solutions or suspensions, etc., containing the compound of the present invention are employed. Topical formulations may generally be comprised of a pharmaceutical carrier, cosolvent, emulsifier, penetration enhancer, preservative system, and emollient.

The actual dose of the compounds of the present invention depends on the specific compound, and on the condition to be treated; the selection of the appropriate dose is well within the knowledge of the skilled artisan.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

What is claimed is:

1. A compound selected from the group consisting of:
   1-[5-chloro-2-(2-ethyl-butoxy)-benzyl]-1H-indole-5-carboxylic acid;
   1-[5-chloro-2-(2-ethyl-butoxy)-benzyl]-1H-indazole-5-carboxylic acid;
   1-(2-chloro-5-isobutoxy-benzyl)-1H-indazole-5-carboxylic acid;
   1-(2-bromo-5-isobutoxy-benzyl)-1H-indazole-5-carboxylic acid;
   1-[2-bromo-5-(2-ethyl-butoxy)-benzyl]-1H-indazole-5-carboxylic acid;
   1-[2-chloro-5-(2-ethyl-butoxy)-benzyl]-1H-indazole-6-carboxylic acid;
   1-(5-bromo-2-isobutoxy-benzyl)-1H-indazole-4-carboxylic acid;
   1-(2-benzyloxy-5-chloro-benzyl)-1H-indazole-5-carboxylic acid;
   1-[5-chloro-2-(4-chloro-benzyloxy)-benzyl]-1H-indazole-5-carboxylic acid;
   1-(5-chloro-2-cyclopentylmethoxy-benzyl)-1H-indazole-5-carboxylic acid;
   1-(5-chloro-2-cyclopropylmethoxy-benzyl)-1H-indazole-5-carboxylic acid;
   1-(2-benzyloxy-5-bromo-benzyl)-1H-indazole-5-carboxylic acid;
   1-[5-bromo-2-(4-chloro-benzyloxy)-bnzyl]-1H-indazole-5-carboxylic acid;
   1-(5-bromo-2-cyclopentylmethoxy-benzyl)-1H-indazole-5-carboxylic acid;
   1-(5-bromo-2-cyclopropylmethoxy-benzyl)-1H-indazole-5-carboxylic acid;
   1-(2-(trifluoromethyl)-5-isobutoxy-benzyl)-1H-indazole-5-carboxylic acid;
   1-(5-bromo-2-cyclopropyl-2-methylmethoxy-benzyl)-1H-indazole-5-carboxylic acid;
   1-(2-isobutoxy-5-trifluoromethoxy-benzyl)-1H-indazole-5-carboxylic acid;
   1-(5-bromo-2-isobutoxy-benzyl)-3-methyl-1H-indazole-5-carboxylic acid;
   1-(2-isobutoxy-5-trifluoromethoxy-benzyl)-3-methyl-1h-indazole-5-carboxylic acid;
   1-[5-chloro-2-(2-ethyl-butoxy)-benzyl]-3-methyl-1H-indazole-5-carboxylic acid;
   1-(5-chloro-2-isobutoxy-benzyl)-3-methyl-1H-indazole-5-carboxylic acid;
   1-(2-isobutoxy-5-trifluoromethyl-benzyl)-3-methyl-1H-indazole-5-carboxylic acid;
   1-[2-(2-ethyl-butoxy)-5-trifluoromethyl-benzyl]-3-methyl-1H-indazole-5-carboxylic acid;
   1-[5-bromo-2-(2-ethyl-butoxy)-benzyl]-3-methyl-1H-indazole-5-carboxylic acid;

1-[5-bromo-2-(1-methyl-cyclopropylmethoxy)-benzyl]-3-methyl-1H-indazole-5-carboxylic acid;
1-[5-chloro-2-(1-methyl-cyclopropylmethoxy)-benzyl]-3-methyl-1H-indazole-5-carboxylic acid;
1-[2-(4-chloro-benzyloxy)-5-trifluoromethyl-benzyl]-1H-indazole-5-carboxylic acid;
1-(2-cyclopentylmethoxy-5-trifluoromethyl-benzyl)-1H-indazole-5-carboxylic acid;
1-(5-chloro-2-cyclopropylmethoxy-benzyl)-1H-indazole-4-carboxylic acid;
1-(5-chloro-2-isobutoxy-benzyl)-1H-indazole-4-carboxylic acid;
1-[5-chloro-2-(2-ethyl-butoxy)-benzyl]-1H-indazole-4-carboxylic acid;
1-[5-chloro-2-(4-chloro-benzyloxy)-benzyl]-1H-indazole-4-carboxylic acid;
1-(5-bromo-2-isobutoxy-benzyl)-1H-indazole-6-carboxylic acid;
1-(5-bromo-2-cyclopentylmethoxy-benzyl)-1H-indazole-6-carboxylic acid;
1-[5-chloro-2-(2-ethyl-butoxy)-benzyl]-1H-indazole-6-carboxylic acid;
1-(5-chloro-3-fluoro-2-isobutoxy-benzyl)-1H-indazole-5-carboxylic acid;
1-(4,5-dichloro-2-isobutoxy-benzyl)-1H-indazole-5-carboxylic acid;
1-[5-bromo-2-(1-ethyl-propoxy)-benzyl]-1H-indazole-5-carboxylic acid;
1-[5-bromo-2-(2,2-dimethyl-propoxy)-benzyl]-1H-indazole-5-carboxylic acid;
1-[5-bromo-2-(2-hydroxy-2-methyl-propoxy)-benzyl]-1H-indazole-5-carboxylic acid;
1-(5-hydroxy-2-isobutoxy-benzyl)-1H-indazole-5-carboxylic acid;
1-[5-(2,2-difluoro-ethoxy)-2-isobutoxy-benzyl]-1H-indazole-5-carboxylic acid;
1-(5-difluoromethoxy-2-isobutoxy-benzyl)-1H-indazole-5-carboxylic acid;
1-(5-bromo-2-isobutoxy-benzyl)-3-ethyl-1H-indazole-5-carboxylic acid;
1-[5-bromo-2-(2-ethyl-butoxy)-benzyl]-3-ethyl-1H-indazole-5-carboxylic acid;
1-(5-bromo-2-isobutoxy-benzyl)-2-methyl-1H-indole-5-carboxylic acid;
1-(5-bromo-2-isobutoxy-benzyl)-1H-indole-5-carboxylic acid;
1-[5-bromo-2-(2-ethyl-butoxy)-benzyl]-2-methyl-1H-indole-5-carboxylic acid;
1-[5-bromo-2-(2-ethyl-butoxy)-benzyl]-1H-indole-5-carboxylic acid;
1-[5-bromo-2-(2-ethyl-butoxy)-benzyl]-1H-indole-6-carboxylic acid;
1-(2-isobutoxy-5-trifluoromethoxy-benzyl)-1H-indole-5-carboxylic acid;
1-(2-isobutoxy-5-trifluoromethoxy-benzyl)-3-methyl-1H-indole-5-carboxylic acid; and
1-[2-(2-ethyl-butoxy)-5-trifluoromethoxy-benzyl]-3-methyl-1H-indole-5-carboxylic acid;

or a pharmaceutically acceptable salt thereof.

* * * * *

UNITED STATES PATENT AND TRADEMARK OFFICE
CERTIFICATE OF CORRECTION

PATENT NO. : 9,567,328 B2
APPLICATION NO. : 13/720520
DATED : February 14, 2017
INVENTOR(S) : William R. Carling et al.

Page 1 of 3

It is certified that error appears in the above-identified patent and that said Letters Patent is hereby corrected as shown below:

On the Title Page

In Column 2, in "Primary Examiner", Line 1, delete "David K O Dell" and insert -- David K O'Dell --, therefor.

In item (57), in Column 2, in "Abstract", Line 7, delete "Wherein" and insert -- wherein --, therefor.

In item (57), in Column 2, in "Abstract", Line 7, delete "$R_4$ A," and insert -- $R_4$, A, --, therefor.

In the Specification

In Column 6, Line 50, delete "ophthamological" and insert -- ophthalmological --, therefor.

In Column 7, Line 15, delete "alrynitis," and insert -- laryngitis, --, therefor.

In Column 7, Line 51, after "labor" insert -- . --.

In Column 8, Line 31, after "thereof" insert -- . --.

In Column 13, Line 66, delete "CHLORO-" and insert -- Chloro- --, therefor.

In Column 15, Line 36, delete "-His" and insert -- -H is --, therefor.

In Column 16, Line 39, after "$M+H^+$" insert -- . --.

In Column 21, Line 2, delete "(0.1g g" and insert -- (0.1 g --, therefor.

In Column 22, Lines 27-28, delete "methanol," and insert -- methanol. --, therefor.

In Column 57, Line 67, after "$M+H^+$" insert -- . --.

Signed and Sealed this
Tenth Day of April, 2018

Andrei Iancu
*Director of the United States Patent and Trademark Office*

In Column 58, Line 28, after "M+H⁺" insert -- . --.

In Column 59, Line 1, delete "5-bromosalicaldehyde" and insert -- 5-bromosalicylaldehyde --, therefor.

In Column 59, Line 17, after "CH₃)" insert -- . --.

In Column 60, Line 3, after "CH₃)" insert -- . --.

In Column 60, Line 35, after "M+H⁺" insert -- . --.

In Column 71, Line 67, after "M+H⁺" insert -- . --.

In Column 76, Line 62, delete "anhydruous" and insert -- anhydrous --, therefor.

In Column 77, Line 32, delete "anhydruous" and insert -- anhydrous --, therefor.

In Column 79, Line 47, after "M+H⁺" insert -- . --.

In Column 83, Line 30, after "M+H⁺" insert -- . --.

In Column 84, Line 30, delete "5-chloroalicaldehyde" and insert -- 5-chlorosalicylaldehyde --, therefor.

In Column 85, Line 67, after "M+H⁺" insert -- . --.

In Column 86, Line 41, after "M+H⁺" insert -- . --.

In Column 87, Line 16, after "M+H⁺" insert -- . --.

In Column 88, Line 6, after "CH₃)" insert -- . --.

In Column 92, Line 32, after "CH₃)" insert -- . --.

In Column 97, Line 8, delete "haemagglutanin" and insert -- haemagglutinin --, therefor.

In Column 100, Lines 9-10, delete "ophthalmogical" and insert -- ophthalmological --, therefor.

In Column 100, Line 28, delete "alrynitis," and insert -- laryngitis, --, therefor.

In Column 100, Line 50, after "invention" insert -- . --.

In Column 101, Line 34, delete "and or" and insert -- and/or --, therefor.

In Column 102, Line 42, delete "2001)" and insert -- 2001). --, therefor.

CERTIFICATE OF CORRECTION (continued)
U.S. Pat. No. 9,567,328 B2

In Column 102, Line 54, delete "IL-1 ά" and insert -- IL-1ά --, therefor.

In Column 103, Lines 19-20, delete "Pruritis" and insert -- Pruritus --, therefor.

In Column 103, Line 29, delete "-1άand" and insert -- 1ά and --, therefor.

In the Claims

In Column 106, Line 42, in Claim 1, delete "bnzyl]-" and insert -- benzyl]- --, therefor.

In Column 107, Line 15, in Claim 1, delete "benzyloxy)- benzyl]" and insert -- benzyloxy)-benzyl]- --, therefor.